United States Patent
Freeman et al.

(10) Patent No.: US 11,963,924 B2
(45) Date of Patent: Apr. 23, 2024

(54) TOOLS FOR CASE REVIEW PERFORMANCE ANALYSIS AND TRENDING OF TREATMENT METRICS

(71) Applicant: ZOLL Medical Corporation, Chelmsford, MA (US)

(72) Inventors: Gary A Freeman, Waltham, MA (US); Catherine A Hodge, Brighton, CO (US); Jill Elaine Maxwell, Lafayette, CO (US); Scott J Robertson, Denver, CO (US); Annemarie E Silver, Bedford, MA (US); Matthew R Vawter, Boulder, CO (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 315 days.

(21) Appl. No.: 17/319,204

(22) Filed: May 13, 2021

(65) Prior Publication Data

US 2021/0308006 A1    Oct. 7, 2021

Related U.S. Application Data

(63) Continuation of application No. 15/835,503, filed on Dec. 8, 2017, now Pat. No. 11,033,455.
(Continued)

(51) Int. Cl.
*G16H 15/00* (2018.01)
*A61B 5/00* (2006.01)
(Continued)

(52) U.S. Cl.
CPC ......... *A61H 31/005* (2013.01); *A61B 5/0006* (2013.01); *A61B 5/316* (2021.01);
(Continued)

(58) Field of Classification Search
CPC ....... A61B 5/0006; A61B 5/349; G16H 40/20
See application file for complete search history.

(56) References Cited

U.S. PATENT DOCUMENTS 6,321,113 B1    11/2001  Parker et al.
6,351,671 B1    2/2002   Myklebust et al.
(Continued)

OTHER PUBLICATIONS

J. M. Ruiz et al., "Relationship between EtCO2 and quality-parameters during cardiopulmonary resuscitation," 2016 Computing in Cardiology Conference (CinC), Vancouver, BC, Canada, 2016, pp. 957-960. (Year: 2016).*
(Continued)

*Primary Examiner* — Evangeline Barr
(74) *Attorney, Agent, or Firm* — Finch & Maloney PLLC

(57) ABSTRACT

An example of a system for post-case analysis of cardiopulmonary resuscitation (CPR) performance trends includes a ventilation metrics device with sensors configured to generate signals indicative of ventilation treatment data during a medical treatment of a patient, and a patient monitor/defibrillator configured to receive the signals, calculate the ventilation treatment data based on the received signals, and transmit the ventilation treatment data, and a remote computing device configured to communicatively couple with the treatment monitoring system and with an output display device, the computing device including at least one memory and at least one processor communicatively coupled to the memory, the at least one processor configured to receive treatment data from the treatment monitoring system, the treatment data including the ventilation treatment data, and provide case review information at a case review dashboard at the output device, the case review information including time trend plots of the ventilation treatment data.

24 Claims, 20 Drawing Sheets

Related U.S. Application Data

(60) Provisional application No. 62/432,383, filed on Dec. 9, 2016.

(51) Int. Cl.

| | | |
|---|---|---|
| *A61B 5/316* | (2021.01) | |
| *A61B 5/339* | (2021.01) | |
| *A61B 5/349* | (2021.01) | |
| *A61H 31/00* | (2006.01) | |
| *G16H 10/60* | (2018.01) | |
| *G16H 40/20* | (2018.01) | |

(52) U.S. Cl.
CPC .............. *A61B 5/339* (2021.01); *A61B 5/349* (2021.01); *A61H 31/007* (2013.01); *G16H 10/60* (2018.01); *G16H 15/00* (2018.01); *G16H 40/20* (2018.01); *A61H 2201/10* (2013.01); *A61H 2201/5012* (2013.01); *A61H 2201/5043* (2013.01); *A61H 2201/5061* (2013.01); *A61H 2230/04* (2013.01)

(56) References Cited

U.S. PATENT DOCUMENTS

| | | | |
|---|---|---|---|
| 6,675,044 B2 | 1/2004 | Chen | |
| 6,990,371 B2 | 1/2006 | Powers et al. | |
| 7,286,997 B2 | 10/2007 | Spector et al. | |
| 8,566,738 B2 | 10/2013 | Van Vlimmeren | |
| 8,712,798 B2 | 4/2014 | Gotman et al. | |
| 8,878,677 B2 | 11/2014 | Nielsen et al. | |
| 9,223,933 B2 | 12/2015 | Edwards et al. | |
| 9,233,255 B2 | 1/2016 | Powers | |
| 9,387,147 B2 | 7/2016 | Elghazzawi et al. | |
| 9,538,933 B2 | 1/2017 | Helfenbein et al. | |
| 10,262,758 B2 | 4/2019 | Mears et al. | |
| 10,963,821 B2 | 3/2021 | Barnes et al. | |
| 2003/0083581 A1 | 5/2003 | Taha et al. | |
| 2006/0173500 A1* | 8/2006 | Walker | A61B 5/0809 607/5 |
| 2006/0173501 A1* | 8/2006 | Stickney | A61H 31/005 607/5 |
| 2007/0010764 A1 | 1/2007 | Palazzolo et al. | |
| 2008/0052124 A1 | 2/2008 | Goodman et al. | |
| 2008/0097785 A1 | 4/2008 | Ali | |
| 2008/0235057 A1 | 9/2008 | Weidenhaupt et al. | |
| 2011/0295078 A1* | 12/2011 | Reid | G06Q 10/10 600/300 |
| 2012/0010543 A1 | 1/2012 | Johnson et al. | |
| 2012/0022606 A1 | 1/2012 | Walker et al. | |
| 2012/0239435 A1 | 9/2012 | Ennett et al. | |
| 2013/0282405 A1 | 10/2013 | Van Zon et al. | |
| 2013/0310718 A1* | 11/2013 | Jensen | A61H 31/005 601/41 |
| 2014/0323928 A1 | 10/2014 | Johnson | |
| 2014/0365175 A1* | 12/2014 | Packer | A61B 5/0006 702/182 |
| 2016/0030758 A1 | 2/2016 | Guiney et al. | |
| 2016/0171167 A9 | 6/2016 | Merry | |
| 2016/0180044 A1 | 6/2016 | Delisle et al. | |
| 2016/0232295 A1 | 8/2016 | Serlie | |
| 2016/0246943 A1 | 8/2016 | Lake et al. | |
| 2016/0287170 A1* | 10/2016 | Ronen | A61B 5/7235 |
| 2016/0317385 A1* | 11/2016 | Salcido | A61H 31/006 |
| 2017/0119621 A1 | 5/2017 | Walker et al. | |

OTHER PUBLICATIONS

Spanos, Costas J. et al., "Real-Time Statistical Process Control Using Tool Data," IEEE Transactions on Semiconductor Manufacturing, vol. 5, No. 4, Nov. 1992.

Steinarsson, Sveinn, "Downsampling Time Series for Visual Representation", Faculty of Industrial Engineering, Mechanical Engineering and Computer Science University of Iceland, Jun. 2013, 87 pages.

\* cited by examiner

Patient ID / MRN: Patient 0190    Case start: 11/8/2016 13:51:31
Device/Unit ID: MEDIC 55          Duration: 00:02:43

Detail | CPR Performance Summary | Zoom | Exports

1800

Download case

Download a case in .zol file format.

[Download case]

CPR Data

Interval:
[60 seconds ▸]    Export CPR data points in CSV format.

Start time:
[Power on time ▸]

Included Compressions:
[Only compressions in drawn CPR periods ▸]

[Request CPR data report]

Case summary report

[Request Case summary report]    Export full disclosure report in PDF format.

FIG. 18

TOOLS FOR CASE REVIEW PERFORMANCE ANALYSIS AND TRENDING OF TREATMENT METRICS

CROSS-REFERENCE TO RELATED APPLICATIONS

This application is a continuation under 35 U.S.C. § 120 of U.S. patent application Ser. No. 15/835,503, filed on Dec. 8, 2017, which claims the benefit under 35 U.S.C. § 119(e) of U.S. Provisional Application No. 62/432,383 filed Dec. 9, 2016. All subject matter set forth in each of the above referenced applications are hereby incorporated by reference in its entirety into the present application as if fully set forth herein.

BACKGROUND

Quality assurance and/or quality inspection personnel, or supervisory personnel, typically review data collected during a patient treatment, for example an emergency medical encounter, in order to evaluate the quality of treatment provided. When cardiopulmonary resuscitation (CPR) is performed, this may include reviewing data about how the CPR was performed.

SUMMARY

An example of a system for post-case analysis of cardiopulmonary resuscitation (CPR) performance trends includes one or more processors configured to communicatively couple to one or more CPR metrics devices and to an output device and a memory including processor-executable instructions configured to cause the one or more processors to receive, from the one or more CPR metrics devices, treatment data including CPR performance data collected by the one or more CPR metrics devices during medical treatment of one or more individuals, determine, from the CPR performance data, two or more CPR performance metrics including a motion-based chest release parameter and at least one of chest compression depth and chest compression rate, and control the output device to concurrently display time trends of the two or more CPR performance metrics, wherein the time trends indicate values of the two or more CPR performance metrics over two or more equal time intervals during the medical treatment of the one or more individuals.

Implementations of such a system may include one or more of the following features. The medical treatment may include a case and the instructions may be further configured to cause the one or more processors to store the treatment data in the memory with one or more case identifiers, receive a post-case request, for the treatment data, that may include the one or more case identifiers, retrieve the treatment data corresponding to the one or more case identifiers, and provide the treatment data to the output device corresponding to the one or more case identifiers to the output device. The instructions may be configured to provide the treatment data to the output device via a network. The instructions may be further configured to cause the one or more processors to receive a request, for the treatment data, that may include one or more filters, retrieve the treatment data according to the one or more filters, and control the output device to provide the retrieved treatment data. The one or more filters may include a patient age group filter indicative of a selected patient age group. The selected patient age group may be one of adult, pediatric, and infant. The one or more filters may include a caregiver filter indicative of one or more individual caregivers or one or more groups of caregivers. The one or more filters may include a time interval selection filter. The instructions may be further configured to aggregate the treatment data according to the time interval selection filter. The time interval selection filter may select a time interval of daily, weekly, monthly, quarterly, or yearly. The instructions may be further configured to cause the one or more processors to communicatively couple to a medical device including electrocardiogram (ECG) sensors, receive a complete time series of ECG data, store the complete time series of ECG data in a lossless format in the memory, provide downsampled ECG data to the output device via a network, and control the output device to display the downsampled ECG data. The displayed downsampled ECG data may retain visual features of the received complete time series of ECG data. The complete time series of ECG data may include all data points provided by a digital conversion of an analog ECG signal from the medical device. The downsampled ECG data may include a portion of the data points provided by the digital conversion of the analog ECG signal from the medical device. The visual features may include QRS complexes in the ECG data. The treatment data may include ECG data and the instructions may be configured to control the output device to display event information concurrently and synchronized in time with the ECG data. The instructions may be configured to cause the one or more processors to control the output device to display the event information as an overlay on the displayed downsampled ECG data. The instructions may be configured to cause the one or more processors to control the output device to display the event information as icons on the displayed downsampled ECG data. The motion-based chest release parameter may be a release velocity. The two or more CPR performance metrics may include an average value of the motion-based chest release parameter and at least one of an average chest compression rate and an average chest compression depth. The two or more CPR performance metrics may include one or more of a ventilation rate, compressions within a target rate range, compressions within a target depth range, a compression fraction, ventilation rate, a pre-shock pause length, and a post-shock pause length. The two or more CPR performance metrics may include one or more of an average ventilation rate, an average compression fraction, an average pre-shock length, and an average post-shock pause length. The treatment data may be associated with one or more tags, and the instructions may be configured to cause the one or more processors to receive an indication of a tag selection and to control the output device to concurrently display time trends for the treatment data for which the one or more tags correspond to the tag selection. The one or more CPR metrics devices may include one or more chest compression sensors. The one or more chest compression sensors may include at least one of a motion sensor, a force sensor, and a proximity sensor. Each of the concurrently displayed time trends may include a visual indication of a target range for a respective CPR performance metric. The values of the two or more CPR performance metrics may be displayed as data points. Each displayed data point may include a visual indication of whether the displayed data point falls within the target range for the respective CPR performance metric. The target range for the respective CPR performance metric may be a user-configurable target range. The target range for the respective CPR performance metric may be a target range for the motion-based chest release parameter. At least one of the concurrently displayed time trends may include the target range for the motion-based chest release parameter. The medical treatment may include a case that may include one or more events. Each of the one or more events may include one of a pause in chest compressions, administration of chest compressions, and a defibrillation shock. The instructions may be configured to cause the one or more processors to automatically identify the one or more events from the CPR performance data. The instructions may be configured to cause the one or more processors to control the output device to display an event summary for the case, the event summary indicating the one or more events. The instructions may be configured to cause the one or more processors to control the output device to display the event summary over the two or more equal time intervals. The one or more processors may be configured to receive the treatment data from one or more ventilation metrics devices. The treatment data may include at least ventilation rate data and end-tidal carbon dioxide data observed by the one or more ventilation metrics devices during artificial ventilation of the one or more individuals. The instructions may be configured to cause the one or more processors to control the output device to concurrently display at least the ventilation rate data and the end-tidal carbon dioxide data along a common time axis that spans a time interval during which the one or more ventilation metrics devices collected the treatment data. The treatment data may include CPR performance data collected by the one or more CPR metrics devices during performance of two or more chest compressions on an individual. The instructions may be configured to cause the one or more processors to control the output device to display a plot of the two or more chest compressions along a time axis. The plot may indicate specific performance data for each of the two or more chest compressions. The instructions may be configured to cause the one or more processors to generate one or more first process-behavior charts for one or more treatment parameters. The one or more treatment parameters may include one or more CPR performance parameters. Data points for the one or more treatment parameters may be aggregated over a time period. The time period may include one of minutes, hours, days, weeks, months, and years. The one or more treatment parameters may be associated with treatment provided by a group of caregivers. The instructions may be configured to cause the one or more processors to generate an indication of an out-of-control first treatment process based on the one or more first process-behavior charts. The indication of the out-of-control first treatment process may include one or more of an alarm and a user notification. The instructions may be configured to cause the one or more processors to perform a multivariate statistical analysis to determine a cause for the out-of-control first treatment process. The instructions may be configured to cause the one or more processors to generate and evaluate one or more second process-behavior charts to determine if a second treatment process may be out-of-control or in control. The second treatment process may include a treatment process change relative to the first treatment process based on the cause for the out-of-control first treatment process. The instructions may be configured to cause the one or more processors to statistically analyze data in the one or more first process-behavior charts to determine a predicted change in a patient outcome based on a patient outcome variable. The patient outcome variable may include one or more of patient survival, patient return of spontaneous circulation (ROSC), EtCO2, volumetric CO2, brain oxygenation, tissue oxygenation, blood flow during chest compression, time to ROSC and percent of patients achieving ROSC. The instructions may be configured to cause the one or more processors to perform a change point analysis based on the predicted change in the patient outcome. The instructions may be configured to cause the one or more processors to determine an effect of a process change on one or more of patient outcomes and caregiver performance based on the change point analysis. The instructions may be configured to cause the one or more processors to adjust one or more of a parameter target range and upper and lower control limits for the one or more first process-behavior charts based on an analysis of the one or more first process-behavior charts.

An example of a system for post-case analysis of cardiopulmonary resuscitation (CPR) performance trends includes one or more processors configured to communicatively couple to one or more CPR metrics devices, to a medical device, and to an output device, and a memory including processor-executable instructions configured to cause the one or more processors to receive, from the one or more CPR metrics devices, treatment data including CPR performance data collected by the one or more CPR metrics devices during medical treatment of one or more individuals, automatically identify one or more events from the CPR performance data, receive, from the medical device, ECG data, time synchronize the one or more events with the ECG data, and control the output device to concurrently display the ECG data and the time synchronized one or more events.

Implementations of such a system may include one or more of the following features. Each of the one or more events may include one of a pause in chest compressions, administration of chest compressions, and a defibrillation shock. The instructions may be configured to cause the one or more processors to receive a complete time series of the ECG data, store the complete time series of the ECG data in the memory, provide downsampled ECG data to the output device via a network, and control the output device to display the downsampled ECG data, wherein the displayed downsampled ECG data retains visual features of the received complete time series of ECG data. The instructions may be configured to cause the one or more processors to store the complete time series of the ECG data in a lossless format in the memory. The complete time series of ECG data may include all data points provided by a digital conversion of an analog ECG signal from the medical device. The downsampled ECG data may include a portion of the data points provided by the digital conversion of the analog ECG signal from the medical device. The visual features may include QRS complexes in the ECG data. The instructions may be further configured to cause the one or more processors to receive a request, for the treatment data, that includes one or more filters, retrieve the treatment data according to the one or more filters, and control the output device to provide the retrieved treatment data. The one or more filters may include a patient age group filter indicative of a selected patient age group. The one or more filters may include a caregiver filter indicative of one or more individual caregivers or one or more groups of caregivers. The one or more filters may include a time interval selection filter. The instructions may be further configured to aggregate the treatment data according to the time interval selection filter. The instructions may be configured to cause the one or more processors to generate one or more process-behavior charts for the treatment data retrieved based on the one or more filters. The one or more filters may include a caregiver filter and the retrieved treatment data may correspond to one or more groups of caregivers. The instructions may be configured to cause the one or more processors to statistically analyze data in the one or more process-behavior charts to determine a predicted change in a patient outcome based on a patient outcome variable. The patient outcome variable may include one or more of patient survival, patient return of spontaneous circulation (ROSC), EtCO2, volumetric CO2, brain oxygenation, tissue oxygenation, blood flow during chest compression, time to ROSC, and percent of patients achieving ROSC. The instructions may be configured to cause the one or more processors to perform a change point analysis based on the predicted change in the patient outcome. The instructions may be configured to cause the one or more processors to determine an effect of a treatment process change on one or more of patient outcomes and caregiver performance based on the change point analysis. The treatment process change may include a change in a target range for one or more CPR performance parameters. The one or more CPR performance parameters may include a chest release parameter. The chest release parameter may be a motion-based chest release parameter determined based on a signal indicative of motion of the chest wall. The one or more CPR performance parameters may include one or more of compression depth and compression rate. The one or more filters may include a patient age filter and the retrieved treatment data corresponds to one or more patient age groups. The instructions may be configured to cause the one or more processors to statistically analyze data in the one or more process-behavior charts, determine a predicted change in a patient outcome based on a patient outcome variable for at least one of the one or more patient age groups, perform a change point analysis based on the predicted change in the patient outcome, and determine an effect of a process change on the patient outcome and caregiver performance based on the change point analysis, wherein the process change includes a change in a CPR performance parameter target range for the at least one of the one or more patient age groups. The patient outcome variable may include one or more of patient survival, patient return of spontaneous circulation (ROSC), EtCO2, volumetric CO2, brain oxygenation, tissue oxygenation, blood flow during chest compression, time to ROSC and percent of patients achieving ROSC.

An example of a computer implemented method of post-case analysis of cardiopulmonary resuscitation (CPR) performance trends includes receiving, from one or more CPR metrics devices, treatment data including CPR performance data collected by the one or more CPR metrics devices during medical treatment of one or more individuals, determining, from the CPR performance data, two or more CPR performance metrics including a motion-based chest release parameter and at least one of chest compression depth and chest compression rate, and controlling the output device to concurrently display time trends of the two or more CPR performance metrics, wherein the time trends indicate values of the two or more CPR performance metrics over two or more equal time intervals during the medical treatment of the one or more individuals.

Implementations of such a method may include one or more of the following features. The medical treatment may include a case and the method may include storing the treatment data in the memory with one or more case identifiers, receiving a post-case request, for the treatment data, that may include the one or more case identifiers, retrieving the treatment data corresponding to the one or more case identifiers, and providing the treatment data to the output device corresponding to the one or more case identifiers to the output device. The method may include providing the treatment data to the output device via a network. The method may include receiving a request, for the treatment data, that may include one or more filters, retrieving the treatment data according to the one or more filters, and controlling the output device to provide the retrieved treatment data. The one or more filters may include a patient age group filter indicative of a selected patient age group. The selected patient age group may be one of adult, pediatric, and infant. The one or more filters may include a caregiver filter indicative of one or more individual caregivers or one or more groups of caregivers. The one or more filters may include a time interval selection filter. The method may include aggregating the treatment data according to the time interval selection filter. The time interval selection filter may select a time interval of daily, weekly, monthly, quarterly, or yearly. The method may include communicatively coupling to a medical device including electrocardiogram (ECG) sensors, receiving a complete time series of ECG data, storing the complete time series of ECG data in a lossless format in the memory, providing downsampled ECG data to the output device via a network, and controlling the output device to display the downsampled ECG data. The displayed downsampled ECG data may retain visual features of the received complete time series of ECG data. The complete time series of ECG data may include all data points provided by a digital conversion of an analog ECG signal from the medical device. The downsampled ECG data may include a portion of the data points provided by the digital conversion of the analog ECG signal from the medical device. The visual features may include QRS complexes in the ECG data. The treatment data may include ECG data and the method may include controlling the output device to display event information concurrently and synchronized in time with the ECG data. The method may include controlling the output device to display the event information as an overlay on the displayed downsampled ECG data. The method may include controlling the output device to display the event information as icons on the displayed downsampled ECG data. The motion-based chest release parameter may be a release velocity. The two or more CPR performance metrics may include an average value of the motion-based chest release parameter and at least one of an average chest compression rate and an average chest compression depth. The two or more CPR performance metrics may include one or more of a ventilation rate, compressions within a target rate range, compressions within a target depth range, a compression fraction, ventilation rate, a pre-shock pause length, and a post-shock pause length. The two or more CPR performance metrics may include one or more of an average ventilation rate, an average compression fraction, an average pre-shock length, and an average post-shock pause length. The treatment data may be associated with one or more tags, and the method may include receiving an indication of a tag selection and controlling the output device to concurrently display time trends for the treatment data for which the one or more tags correspond to the tag selection. The one or more CPR metrics devices may include one or more chest compression sensors. The one or more chest compression sensors may include at least one of a motion sensor, a force sensor, and a proximity sensor. Each of the concurrently displayed time trends may include a visual indication of a target range for a respective CPR performance metric. The values of the two or more CPR performance metrics may be displayed as data points. Each displayed data point may include a visual indication of whether the displayed data point falls within the target range for the respective CPR performance metric. The target range for the respective CPR performance metric may be a user-configurable target range. The target range for the respective CPR performance metric may be a target range for the motion-based chest release parameter. At least one of the concurrently displayed time trends may include the target range for the motion-based chest release parameter. The medical treatment may include a case that may include one or more events. Each of the one or more events may include one of a pause in chest compressions, administration of chest compressions, and a defibrillation shock. The method may include automatically identifying the one or more events from the CPR performance data. The method may include controlling the output device to display an event summary for the case, the event summary indicating the one or more events. The method may include controlling the output device to display the event summary over the two or more equal time intervals. The method may include receiving the treatment data from one or more ventilation metrics devices. The treatment data may include at least ventilation rate data and end-tidal carbon dioxide data observed by the one or more ventilation metrics devices during artificial ventilation of the one or more individuals. The method may include controlling the output device to concurrently display at least the ventilation rate data and the end-tidal carbon dioxide data along a common time axis that spans a time interval during which the one or more ventilation metrics devices collected the treatment data. The treatment data may include CPR performance data collected by the one or more CPR metrics devices during performance of two or more chest compressions on an individual. The method may include controlling the output device to display a plot of the two or more chest compressions along a time axis. The plot may indicate specific performance data for each of the two or more chest compressions. The method may include generating one or more first process-behavior charts for one or more treatment parameters. The one or more treatment parameters may include one or more CPR performance parameters. Data points for the one or more treatment parameters may be aggregated over a time period. The time period may include one of minutes, hours, days, weeks, months, and years. The one or more treatment parameters may be associated with treatment provided by a group of caregivers. The method may include generating an indication of an out-of-control first treatment process based on the one or more first process-behavior charts. The indication of the out-of-control first treatment process may include one or more of an alarm and a user notification. The method may include performing a multivariate statistical analysis to determine a cause for the out-of-control first treatment process. The method may include generating and evaluating one or more second process-behavior charts to determine if a second treatment process may be out-of-control or in control. The second treatment process may include a treatment process change relative to the first treatment process based on the cause for the out-of-control first treatment process. The method may include statistically analyzing data in the one or more first process-behavior charts to determine a predicted change in a patient outcome based on a patient outcome variable. The patient outcome variable may include one or more of patient survival, patient return of spontaneous circulation (ROSC), EtCO2, volumetric CO2, brain oxygenation, tissue oxygenation, blood flow during chest compression, time to ROSC and percent of patients achieving ROSC. The method may include performing a change point analysis based on the predicted change in the patient outcome. The method may include determining an effect of a process change on one or more of patient outcomes and caregiver performance based on the change point analysis. The method may include adjusting one or more of a parameter target range and upper and lower control limits for the one or more first process-behavior charts based on an analysis of the one or more first process-behavior charts.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIG. 18 illustrates an export user interface page, according to embodiments of the present disclosure.

Figure 1:
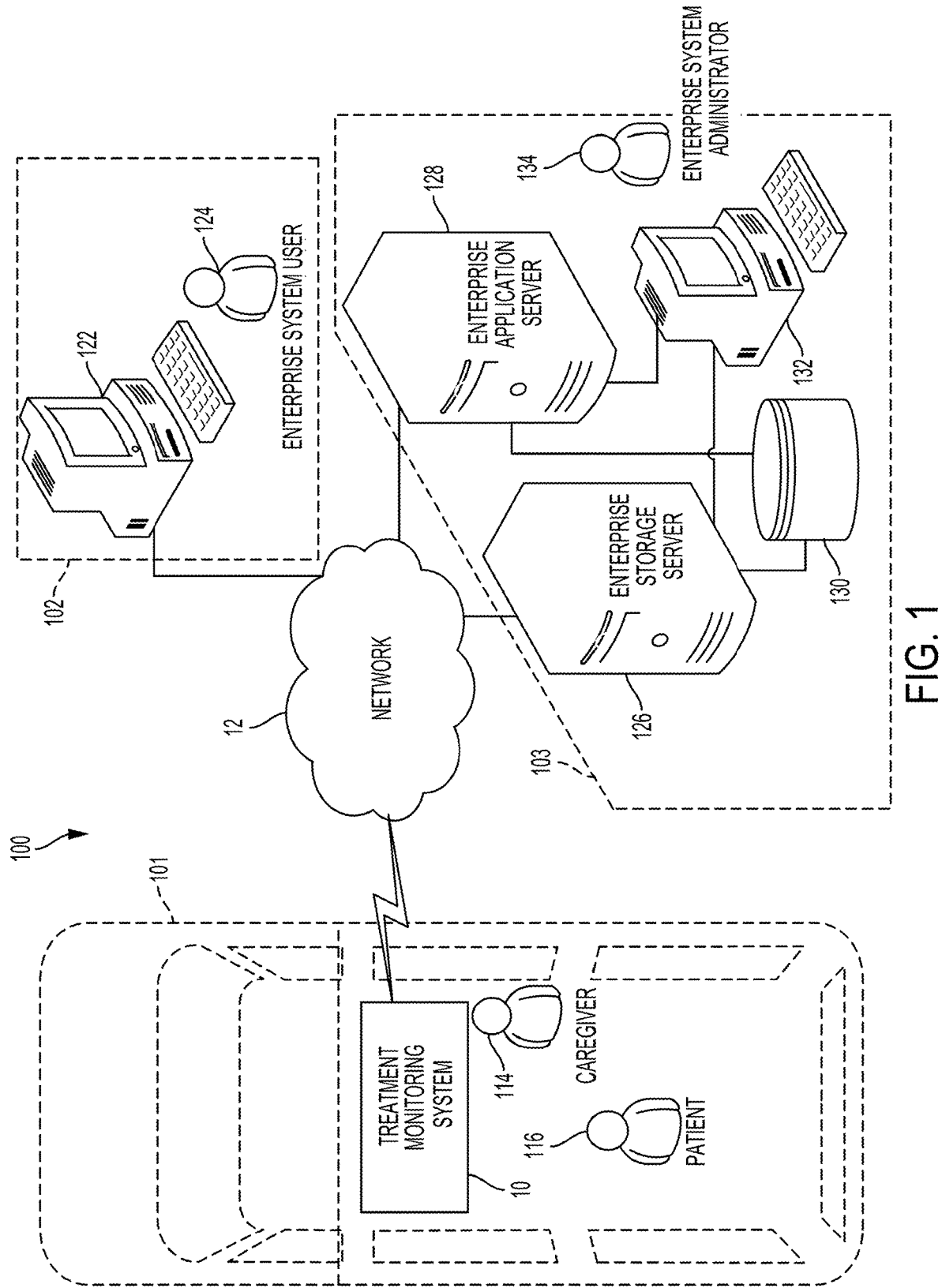
FIG. 1 illustrates a medical data management system that permits post-case review and trending analysis, according to embodiments of the present disclosure.

While embodiments of the disclosure are amenable to various modifications and alternative forms, specific embodiments have been shown by way of example in the drawings and are described in detail below. The intention, however, is not to limit the disclosure to the particular embodiments described and modifications, equivalents, and alternatives fall within the scope of the disclosure as discussed herein.

DETAILED DESCRIPTION

In providing services, such as medical services, which can include emergency medical services, it is desirable for various individuals to be able to review treatment data a time after the performance of these services. The treatment data reviewed was collected during the performance of these services. This type of data review is considered post-case review as it occurs after the conclusion of a patient treatment case. In an implementation, the tools described herein may be used for post-event review, e.g., at a time after the conclusion of an event which may or may not be after the conclusion of the case. Post-case review may enable a determination of the quality of the services being provided, and/or a determination of other performance-related measures or statistics about the provision of the service. For example, a patient may receive treatment for a cardiac arrest on Nov. 8, 2016 over a three-minute time duration starting at approximately 13:51 (i.e., 1:51 p.m.) and ending at 13:54 (i.e., 1:54 p.m.). A treatment monitoring system 10 (as discussed in further detail below) may collect the treatment data over this three-minute time duration of the case. At a later date and time, for example on Nov. 10, 2016 at 8:00 (i.e., 8:00 a.m.), a post-case review may be performed using the treatment data collected during the case.

A case refers to, for example, a series of treatment events administered to a patient on a particular date and over a particular time duration. For example, a patient may experience cardiac arrest or another medical condition. In response, resuscitative care may be administered to the patient. The resuscitative care, for example, CPR, may include the series treatment events (e.g., assessing a patient's condition, applying electrodes to a patient, chest compressions, ventilation, defibrillation shock, drug delivery, transport to a hospital, etc.). Further, during the resuscitative care, the patient may exhibit various responses including, for example, return of spontaneous circulation (ROSC). Additionally, physiological parameters for the patient may be determined continuously or at various times during the resuscitative care. These physiological parameters may include pulse rate, electrocardiogram (ECG), blood oxygen levels, etc. The case may include all of these events, commencing with onset of resuscitative care and ending with the termination of the resuscitative care. For example, if the patient goes into ROSC or is delivered to the hospital, these events may terminate the case. Treatment data may be collected and recorded by a treatment monitoring system 10, as discussed in detail below, over the course of the case.

Once the case is terminated, the treatment data collected during the case may be reviewed and analyzed to evaluate, for example, the efficacy of the treatments provided and the quality of the procedures used to deliver these treatments. Thus, this review and analysis may constitute post-case review. For example, such data analysis may provide an evaluation of the skills and training for personnel performing resuscitative care services. Post-case review of treatment data may also be used to determine the medical efficacy of various treatment techniques and protocols such as cardiopulmonary resuscitation (CPR) and other resuscitation techniques and protocols. However, the post-case review tools described herein are not limited to medical efficacy evaluations as these tools offer the advantage of providing quantitative evaluations of caregivers. Indeed, concurrently reviewing, during the post-case review, data for particular services and/or data for particular parameters of these services may, for example, enable a holistic evaluation of the effects of skills and training, and changes in skills and training, on the medical efficacy of the various treatment techniques and protocol along with inter-related effects of these parameters and services. The particular services may include, for example, chest compressions, ventilation, and defibrillation. The skills and training evaluated may include skill and training for delivering these and other resuscitative and medical services. The particular parameters for these services may include, for example, chest compression depth, chest compression rate, ventilation rate, end-tidal carbon dioxide data, shock timing, shock energy, etc. The post-case review tools may enable an observance and evaluation of trends in the data as they include methods for reviewing changes in the data, and/or various performance metrics, over multiple sets of performances and/or services and/or time intervals. Such data analysis may assist in determining whether the performance of the services meets certain goals and/or criteria with regard to protocols, training, and medical efficacy. Additionally, such data analysis may enable improvements of performance of the services and/or identification of parameters that may affect quality of the performance of the services. Further, these performance metrics may be evaluated for various groups of patients and/or caregivers to compare and evaluate efficacy for particular patient populations and for various caregiver organizations.

Referring to FIG. 1, an example is shown of a medical data management system 100 that permits post-case review and trending analysis, according to embodiments of the present disclosure. The system 100 enables advanced data management, integration and presentation of medical data, including emergency medical services (EMS) data, collected by multiple devices.

The system 100 may include a treatment environment 101, a user environment 102, and an enterprise environment 103. Each of these environments may include computing devices that are communicatively coupled to one another via network 12, for example a computer network (e.g., the Internet), according to embodiments of the present disclosure. Devices within the various environments 101, 102, 103 may be communicably coupled via a network 12, such as, for example, the Internet. As used herein, the phrase "communicatively coupled" refers to any coupling whereby information may be passed. Thus, for example, communicatively coupled includes electrically coupled by, for example, a wire; optically coupled by, for example, an optical cable; and/or wirelessly coupled by, for example, a radio frequency or other transmission media. "Communicatively coupled" also includes, for example, indirect coupling, such as through a network, or direct coupling.

For example, the treatment environment 101 may include one or more computing devices that may include patient treatment devices as discussed below with regard to FIG. 2. The user environment 102 may include one or more computing devices 122 and the enterprise environment 103 may include one or more computing devices 132. The computing device(s) 122 may include an output device, for example, a display. The computing device(s) 122 may further include one or more of a network access device, an enterprise user workstation, and an enterprise user terminal. The computing device(s) 132 may include one or more of an output device, a network access device, an enterprise administrator workstation, and an enterprise administrator terminal.

In the treatment environment 101, a caregiver 114 treats a patient 116. The treatment environment 101 may include a network of data entry devices as well as diagnostic and therapeutic devices established at time of treatment of a patient. In some embodiments, the treatment environment 101 may be a mobile treatment environment, for example a vehicle like an ambulance. In other embodiments, the treatment environment 101 may be a scene of an emergency, which may include an outdoor location and an indoor location, a hospital, a doctor's office, a clinic, and/or another medical care facility. Various systems may be used to gather information about the patient 116 and/or the caregiver 114 during an emergency medical services case (for example, a patient treatment resulting in an ambulance ride to an advanced care facility).

In an implementation, the system 100 may include a plurality of treatment environments. Each treatment environment 101 of the plurality of treatment environments may provide treatment data to the network 12 for access by the user environment 102 and the enterprise environment 103. Each treatment environment of the plurality of treatment environments and/or a group of treatment environments (e.g., a subset of the plurality of treatment environments) may correspond to a caregiver organization (e.g., a hospital, a department within a hospital, an EMS group, a fire department, etc.).

Figure 2:
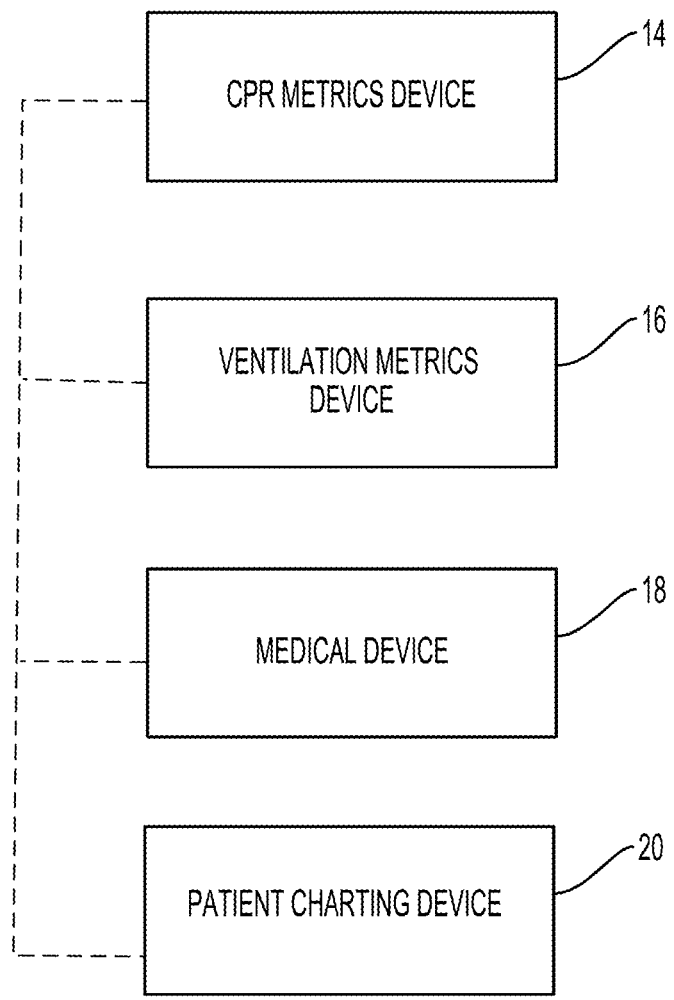
FIG. 2 illustrates an example of a treatment monitoring system, according to embodiments of the present disclosure.

Referring to FIG. 2, a schematic diagram of an example of a treatment monitoring system is shown. As illustrated in FIG. 2, the treatment monitoring system 10 may include and/or be communicatively coupled to one or more devices that gather treatment performance metrics (i.e., treatment data) to help assess the quality of a caregiver's performance in treating the patient 116. The treatment monitoring system 10 may also be a patient treatment device, or another kind of device that includes patient monitoring and/or patient treatment capabilities. The treatment monitoring system 10 may include, for example, one or more CPR metrics device(s) 14, one or more ventilation metrics device(s) 16, and/or one or more medical device(s) 18. One or more of the CPR metrics device(s) 14, the ventilation metrics device(s) 16, and the medical device(s) 18 may be communicatively, mechanically, and/or electrically coupled to one another via one or more wired and/or wireless connections. Based on the disclosure provided herein, one of ordinary skill in the art will recognize that fewer or additional devices may be included as part of, or as functionally part of, the treatment monitoring system 10.

The CPR metrics device(s) 14 may collect CPR treatment data, which may include CPR performance data. The CPR metrics device 14 may be configured to be coupled to the patient 116 and/or physically placed on, near, and/or adjacent to the patient 116 in order to monitor various physical parameters associated with the delivery of CPR to the patient 116 by the caregiver 114. The CPR metrics device 14 may be configured to detect the presence of and/or the timing of and/or the depth/displacement of and/or the velocity of and/or the acceleration of and/or the force of chest compressions delivered to the patient 116. For example, the CPR metrics device 14 may monitor and record the time(s) that CPR began, the time(s) that CPR ended, pauses or gaps in CPR administration, the occurrence of each chest compression, the depth of each chest compression, and the release velocity of each chest compression, and the time(s) when a shock is administered to the patient for cardioversion, according to embodiments of the present disclosure. CPR metrics device 14 may monitor additional and/or fewer such parameters.

For example, the CPR metrics device may monitor one or more chest release parameters, such as release velocity (which may be the velocity of the chest wall during the period when the CPR provider, e.g., a person providing manual chest compressions or a device providing automated chest compressions, is releasing the chest to allow it to expand), the proximity, force and/or contact of the CPR provider's hands with the chest during the upward expansion of the chest after a compression, etc. The release velocity may be an upward velocity that increases during the upward acceleration of the chest (i.e., positive acceleration) as the chest returns to its original position prior to being displaced by the chest compression. Chest release parameters, such as average release velocity, an average instantaneous release velocity, and/or a peak release velocity may be evaluated and compared to a threshold to determine the adequacy of chest release with regard to hemodynamics. An evaluation of chest release parameters may be valuable in improving the efficacy of CPR, as substantial release of the chest promotes beneficial refilling of the heart with blood.

The CPR metrics device 14 may be a chest compression monitor and may be a standalone device, such as, for example, a puck, a watch, a smartphone, etc. that may be configured to be communicatively and/or electronically coupled to a defibrillator, an electrode assembly, and/or a computing device. Alternatively, the CPR metrics device 14 may be incorporated into an electrode assembly. For example, the electrode assembly may include a sternal electrode, an apex electrode, and bridge connecting these electrodes. The CPR metrics device 14 may be disposed in the bridge. The CPR metrics device 14 may be adapted to be held in an approximately fixed relation to the chest, specifically the anterior surface of the thorax over the sternum, so that during CPR compressions the movement of the chest compression monitor and sensors of the monitor closely correspond to downward and upward motion of the chest wall of the patient. The CPR metrics device 14 may include a housing and a motion sensor assembly and/or a force sensor assembly disposed within the housing.

The motion sensor assembly may be an accelerometer assembly, such as, for example, a multi-axis accelerometer assembly, with two or three distinct accelerometers arranged orthogonally to each other, capable of detecting acceleration on two or three orthogonal axes. These axes may be aligned in the CPR metrics device 14 to coincide with a compression axis for the chest of the patient (e.g., typically, the vertical axis which corresponds to the anterior/posterior axis of the patient when supine) and one or two axes orthogonal to the compression axis (typically two horizontal axes). The accelerometer assembly may also include separate accelerometers, with two or three accelerometers rotatably mounted to the housing. With this arrangement, the accelerometer signals may be indicative of chest compression depth. The accelerometers may produce an acceleration signal corresponding to acceleration of the chest wall achieved during CPR compressions, and a control system may receive and process this signal to determine CPR metrics including compression depth, compression rate, compression velocity, and/or release velocity. As other examples, the motion sensor may include velocity sensors which directly measure velocity and/or distance sensors (e.g., proximity sensors) which track the displacement of the compression module. Proximity sensors may include ultrasonic distance sensors, optical distance sensors, magnetic motion sensors, RFID sensors, and/or emitter/detector arrangements. As another example, velocity may be measured directly using an imposed magnetic field and inductive sensors by placing a magnet on one side of the thorax (on or under the back of the patient) and an inductive coil on the opposite surface of the thorax (on the chest wall, or anterior surface of the chest) to detect voltage based on induction of current in the coil, which varies with the speed of coil through the magnetic field. A rheostat and mechanical linkage fixed to the CPR metrics device 14 may measure chest displacement during CPR. As a further example, the motion sensor may utilize infrared optical illumination and detection of the reflected infrared light from the patient. This system can be used as a distance sensor in the system described above, from which velocity of the chest wall movement can be determined. Although a single sensor and/or a single type of sensor may be sufficient to provide the necessary information to determine CPR metrics, velocity and chest displacement, multiple sensors and sensor types can be used in various combinations. For example, a velocity sensor may be used to directly measure velocity, and a displacement sensor operable independently from the velocity sensor may be used to directly measure displacement, such that the control system can determine velocity from the velocity sensor and determine displacement from the displacement sensor.

In some examples, the depth of CPR chest compressions, the rate of CPR chest compressions, and/or the chest release parameter may be determined based on information collected from one or more accelerometers included in the one or more CPR metrics devices 14. The one or more accelerometers may generate an acceleration signal in response to motion of the CPR metrics device(s) 14 in conjunction with chest compressions. This acceleration signal may be received by one or more of the medical device 18 and/or another computing component of the treatment monitoring system 10. Further, this acceleration signal may be sent to the enterprise application system 128. One or more of the medical device 18, another computing component of the treatment monitoring system 10 and the enterprise application server 128 may determine motion-based parameters based on the acceleration signal. The motion-based parameters are based on a signal, such as the acceleration signal, that is indicative of chest wall motion. For example, the motion-based parameters may include a motion-based chest release parameter. The acceleration signal from the CPR metrics device 14 provides an acceleration waveform indicative of acceleration of the chest wall. This acceleration waveform may be integrated to determine a velocity waveform and may be doubly integrated to determine a displacement waveform. One or more chest release parameters may be determined based on one or more of the acceleration waveform, the velocity waveform, and the displacement waveform. As another example, the chest release parameter may be determined from a velocity sensor and/or from a displacement sensor.

As an additional example, the chest release parameter may be determined based on information collected from a proximity sensor such as, for example, a light sensor or a capacitive touch sensor. For example, the CPR metrics device 14 may include the light sensor or the capacitive touch sensor and an accelerometer may be affixed to a victim's chest at a location corresponding to the location of the rescuer's hands when delivering manual chest compressions prior to the administration of CPR.

The light sensor measures light impinging on the sensor and provides the information to a computing device. The computing device may be configured to processes the information to determine whether the rescuer's hands are in contact with the light sensor. For example, if the accelerometer is affixed to the victim's chest or on top of the CPR sensor at a location corresponding to the location of the rescuer's hands when delivering manual chest compressions, the presence or absence of light detection by the light sensor may be used to determine whether the rescuer is fully releasing the chest of the victim during the administration of chest compressions. Examples of light sensors include photocells or photo-resistors that change resistance when light shines on it, charged coupled devices (CCD) that transport electrically charged signals, photomultipliers that detect light and multiply it, and the like.

For example, when a rescuer's hands are raised away from the victim's chest and are not in contact with the victim's chest (e.g., when the rescuer releases from a compression), the light sensor is uncovered. Thus, when the rescuer's hands are raised away from the victim's chest light can reach the light sensor. When the light sensor is covered, light may not be able to reach the light sensor. Thus, the presence and absence of light measured by the light sensor may indicate whether the rescuer is fully releasing his/her hands from the victim's chest. For example, the detection of light may indicate that the rescuer has released his/her hands from the victim's chest. Conversely, the lack of light detection may indicate that the rescuer is maintaining physical contact with the victim's chest after the administration of compression.

In some examples, the information from the light sensor may be compared to CPR compression rate information from the accelerometer to determine whether the user is releasing the victim's chest fully. More particularly, if the rescuer is releasing the victim's chest fully, light may be observed by the light sensor for every compression. Thus, the defibrillation device may determine a frequency at which a threshold amount of light is detected by the light sensor and compare the determined frequency with a compression rate obtained from the accelerometer. If the determined frequency from the light sensor is the same (or within an acceptable range from) the compression rate obtained from the accelerometer, the defibrillation device may determine that the rescuer is appropriately releasing the victim's chest. On the other hand, if the frequency from the light sensor is less than the compression rate, the defibrillation device may determine that the rescuer is not appropriately releasing the victim's chest.

For the capacitive touch sensor, when the human hand(s) approaches or touches the capacitive sensor, the capacitive sensor may detect this movement or touch of the hand based on a measured change in capacitance. The level of capacitance may indicate whether or not the rescuer hand is touching the capacitor sensor.

When the rescuer's hands are raised away from the victim's chest and are not in contact with the victim's chest (e.g., when the rescuer releases from a compression), the capacitive touch sensor may be uncovered. Thus, when the rescuer's hands are raised away from the victim's chest, the capacitance measured by the capacitive touch sensor is based on the dielectric of air. However, when the rescuer's hands are in contact with the victim's chest (e.g., when the rescuer is providing a compression) the capacitive touch sensor may be covered and contact may be made between the rescuer's hands and the sensor. When the human hands approach or touch the capacitive touch sensor, the sensor may detect this movement or touch of the hand and measure a change in capacitance. Thus, the measured capacitance level may be used by the processor or device to determine whether or not the rescuer hand is touching the capacitor sensor and may be used to determine whether or not the rescuer is fully releasing his/her hands from the victim's chest. When capacitance remains at a level indicating that the rescuer's hands are likely in contact with the capacitive touch sensor, the rescuer may not be fully releasing his/her hands between compressions.

In some examples, the information from the capacitive touch sensor can be compared to CPR compression rate information from the accelerometer to determine whether the user is releasing the victim's chest fully. More particularly, if the rescuer is releasing the victim's chest fully, a change in capacitance may be observed by the capacitive touch sensor for every compression. Thus, the defibrillation device may determine a frequency at which a threshold change in capacitance is detected by the capacitive touch sensor and compare the determined frequency with a compression rate obtained from the accelerometer. If the determined frequency from the capacitive touch sensor is the same (or within an acceptable range from) the compression rate obtained from the accelerometer, the defibrillation device may determine that the rescuer is appropriately releasing the victim's chest. On the other hand, if the frequency from the capacitive touch sensor is less than the compression rate, the defibrillation device may determine that the rescuer is not appropriately releasing the victim's chest.

The ventilation metrics device 16 may monitor and/or record ventilation treatment data for ventilation treatment of a patient. The ventilation treatment data may include one or more of ventilation rate data and end-tidal carbon dioxide data. For example, the ventilation metrics device may monitor and/or record the time(s) when ventilation begins, the time(s) when ventilation ends, the occurrence of each inhale and/or exhale cycle, patient breathing, the timing of ventilation activity, various pressures during the inhale/exhale cycle, and volumes and volume flow rates.

The ventilation metrics device 16 may include one or more devices configured to monitor, detect, treat, and/or derive or calculate respiration rate, blood oxygen level, end-tidal carbon dioxide level, and/or pulmonary function. For example, the ventilation metrics device 16 may be, for example, but not limited to, a pulse oximeter, a blood oxygen monitor, an air flow sensor, a spirometer, a lung function monitor, and/or a capnography and/or capnometry device.

The medical device(s) 18 may be, for example, a patient monitor, a defibrillator, or a combination thereof. The medical device(s) 18 may collect medical treatment data based on the type of medical device. For example, the medical device 18 may be a defibrillator, for example, an external defibrillator (e.g., a ZOLL® X Series® device, a ZOLL® R Series® device, a ZOLL® Propaq® M device, a ZOLL® Propaq® MD device, a ZOLL® M Series® device, or a ZOLL® M Series® CCT device), a wearable medical device (e.g., a ZOLL® LifeVest® device), or an automated external defibrillator (AED) (e.g., a ZOLL® AED Plus® device, a ZOLL® AED Pro® device, or a ZOLL® AED 3® device). The defibrillator may be configured to deliver a therapeutic shock to a patient's cardiac system, according to embodiments of the present disclosure. The defibrillator may include electrodes and/or sensors configured for attachment to the patient to monitor heart rate and/or to generate electrocardiographs ("ECG's"). The medical treatment data may include the ECG data, impedance data, defibrillation data, and/or other data received, collected, and/or determined by the defibrillator. In an implementation, the electrodes and/or sensors may include the CPR metrics device 14. The medical device 18 may further monitor, detect, treat, and/or derive or calculate treatment data such as, but not limited to, blood pressure, temperature, blood glucose level, weight, and/or other patient condition information (e.g., physiological information). The medical device 18 may be configured to physically and/or communicatively couple with the patient 116 to gather the clinical and/or physiological information from the patient. In various implementations, the medical device 18 may be a patient monitor/defibrillator. The patient monitor/defibrillator may include features additional to what is needed for mere operation as a defibrillator. These additional features may enable the patient monitor/defibrillator to monitor and collect at least a portion of the physiological information for the patient.

Other systems and/or devices may be present in the treatment environment 101 or capable of gathering data from the treatment environment 101. For example, the treatment environment 101 may include a patient charting device 20. The patient charting device 20 may be a computing device used by the caregiver 114 to generate records and/or notes about the patient's condition and/or treatments applied to the patient. The patient charting device 20 may be a tablet, a wristband, a smart-phone, a laptop, etc. The patient charting device 20 may include a touch screen or voice recognition data entry. For example, the patient charting device 20 may be used to note a dosage of medicine given to the patient 116 at a particular time. The patient charting device 20 may include a clock, which may be synchronized with an external time source such as a network or a satellite to prevent the caregiver 114 from having to manually enter a time of treatment or observation (or having to attempt to estimate the time of treatment for charting purposes long after the treatment was administered). The patient charting device 20 may also be used to record biographic and/or demographic and/or historical information about a patient, for example the patient's name, identification number, height, weight, and/or medical history, etc.

As further examples, the treatment environment 101 may include a navigation device, a satellite positioning system device, a driver safety monitoring system, an inventory control system, a blood alcohol monitor, a breathalyzer instrument, and/or an EMS crew scheduling system.

The user environment 102 may include the one or more computing devices 122 communicatively coupled to the network 12, in a manner that permits an enterprise system user 124 to access data from one or more computers or servers (e.g., the servers 126, 128) via the network 12. The one or more computing devices 122 may include, for example, but not limited to, a personal computer, a workstation, a laptop, a tablet, a smartphone, a monitor, a user workstation, a user terminal, etc.

The enterprise environment 103 includes the one or more servers (e.g., storage servers 126 and/or application servers 128). The one or more servers include and/or are communicatively coupled with one or more databases 130. The administrative environment may further include one or more computing devices 132 capable of accessing and/or administering the servers 126, 128 as well as resources on the network 12, according to embodiments of the present disclosure. For example, the computing devices 132 may include an administrator workstation.

The devices within each of the treatment environment 101, the user environment 102, and the enterprise environment 103 are communicatively coupled to one another via the network 12; these connections may be direct or indirect, as well as wireless, wired, and/or optical, for example. In addition, although wires are shown to communicatively couple devices within each environment, such couplings may include additional and/or alternative forms of communicative coupling.

As used herein, the phrase "communicatively coupled" is used in its broadest sense to refer to a coupling through which information may be passed. Thus, for example, communicatively coupled includes electrically coupled by, for example, a wire, optically coupled by, for example, an optical cable, and/or wirelessly coupled by, for example, a radio frequency signal transmission media. "Communicatively coupled" also includes, for example, indirect coupling, such as through a network or a series of devices and/or communication protocols, or direct coupling. For example, "communicatively coupled" may include a wireless coupling via cellular communication and/or Wi-Fi and/or Bluetooth®. The network 12 may also take the form of an ad hoc, self-configuring, self-healing network.

The user environment 102, also referred to as an enterprise environment, may include an enterprise storage server 126. Although FIG. 1 depicts one treatment environment 101, more than one treatment environment 101 may be communicatively coupled with the enterprise environment 103 and/or the enterprise storage server 126. The enterprise storage server 126 may store received information (e.g., information transmitted by and received from the treatment monitoring system 10) in the database 130. Further, the stored information may include an authenticated time stamp and/or an identifier associating the information with a treatment environment 101 (e.g., a particular EMS device, EMS vehicle, EMS facility, medical practitioner, medical facility, etc.). In this way, data from multiple treatment environments 101 may be accessed by the enterprise system user 124. Such data may include clinical and nonclinical information. The enterprise storage server 126 may securely store the information received from one or more treatment monitoring systems 10 to permit later use of the information. For example, the treatment monitoring system 10 may receive patient-identifying information such as name, address, and/or social security number (e.g., via the patient charting device 20). The treatment monitoring system 10 may convey some or all of the patient-identifying information to enterprise storage server 126. The enterprise storage server 126 is configured to query the database 130 for records, which include previously stored records, involving the same patient 116. As such, information sorted by patient and/or historical information may also be accessed by the enterprise system user 124. The enterprise system user 124 may request treatment information (e.g., treatment data, reports, summaries, and/or calculated parameters determined from the treatment data), based on one or more case identifiers stored with the treatment data. The case identifiers may include, for example, one or more of the authenticated time stamp, the identifier associating the information with the treatment environment 101, the patient-identifying information, and caregiver identifying information. The request may be a post-case request made after the conclusion of the case. In an implementation, the request may occur during the case and/or may be a post-event request during the case. In response to the request, the enterprise server 128 may provide the treatment information corresponding to the case identifiers for display and analysis via a case review dashboard 400.

The enterprise storage server 126 may be configured to receive information from the treatment monitoring system 10 for each event, encounter, and/or service during a case and store all or a portion of the data, for example in a database 130. The data may be stored in a single memory or across multiple memories and the data may be stored in various formats and/or correlations. The enterprise application server 128 may be configured to access the data stored on the enterprise storage server 126 and/or the database 130, and may be configured to perform analysis, for example statistical analysis on the data. The enterprise application server 128 may also assemble some or all of the analysis and/or the data into a web page, portal, dashboard, and/or report, and communicate it to the computing device 122 via the network 12, for example by serving the data as a web page for receipt and display by a web browser on the computing device 122, according to embodiments of the present disclosure. An enterprise system administrator 134 may adjust the programming and/or behavior of the enterprise storage server 126 and/or the enterprise application server 128 via administrator workstation 132, according to embodiments of the present disclosure. Although the term "environments" is used herein to describe various system architectures, one of ordinary skill in the art will understand, based on the present disclosure, that the environments 101, 102, and/or 103 are not intended to be geographically limiting. For example, the enterprise application server 128 may reside in a different geographic location from the enterprise storage server, according to embodiments of the present disclosure. The same possibility exists for any of the systems and/or devices described herein, or portions thereof, whose function is not tied to its location.

Figure 3:
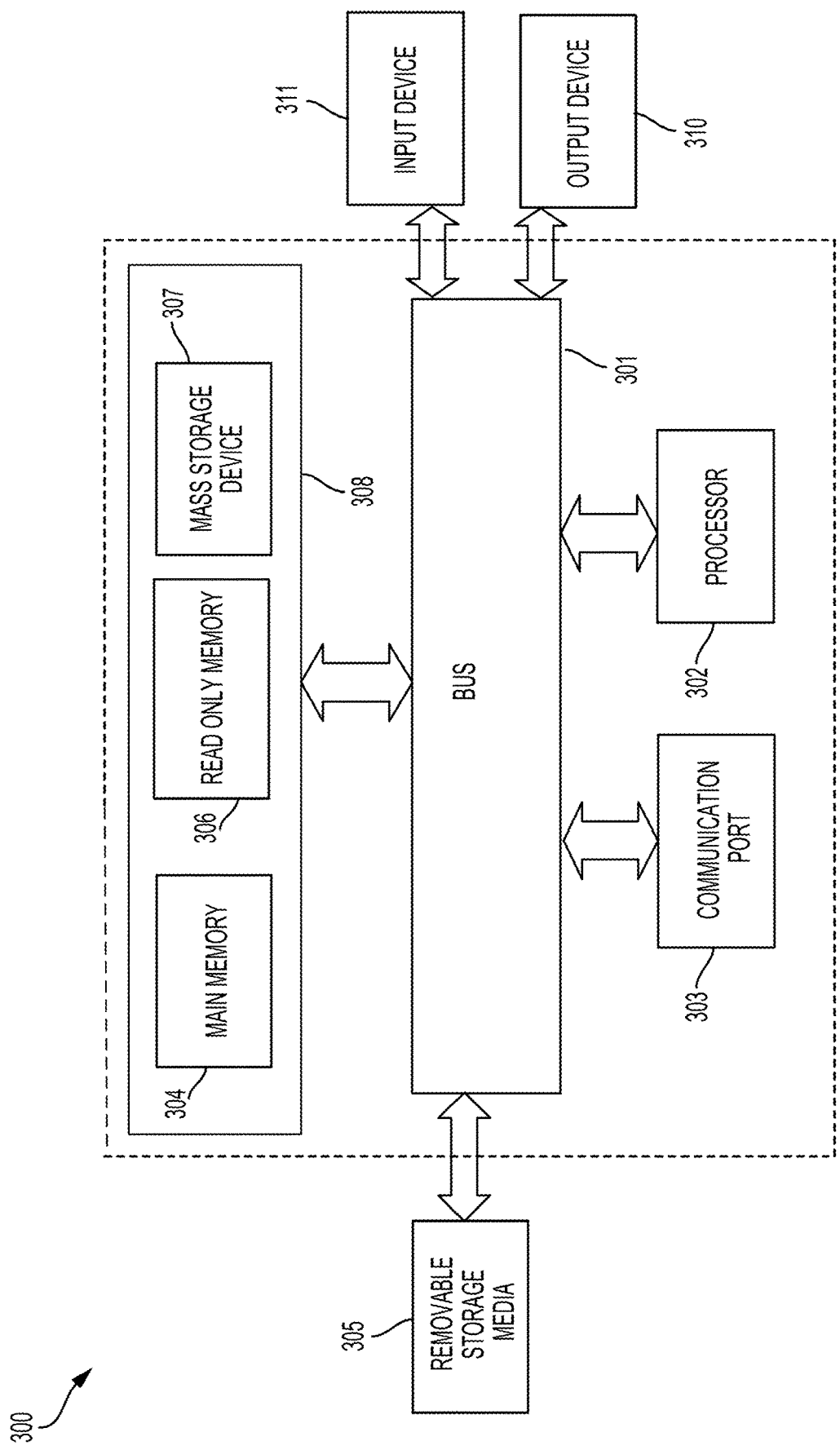
FIG. 3 illustrates a computer system, according to embodiments of the present disclosure.

Referring to FIG. 3, an example of a computer system 300 configured to implement embodiments of the present disclosure is shown. One or more of the treatment monitoring system 10, the computing device 122, the enterprise application server 128, the enterprise storage server 126, and the computing device 132 may include at least a portion of the computer system 300. According to the present example, the computer system includes a bus 301, one or more processors 302, at least one communication port 303, and a memory 308. Processor(s) 302 may be for example, but not limited to, an Intel® Itanium® or Itanium 2® processor(s), or AMD® Opteron® or Athlon MP® processor(s), or Motorola® lines of processors. Communication port(s) 303 may be, for example, but not limited to, an RS-232 port for use with a modem based dialup connection, a 10/100 Ethernet port, a Bluetooth® or WiFi interface, or a Gigabit port using copper or fiber, for example. Communication port(s) 303 may include a network access device compatible with a network, such a Local Area Network (LAN), Wide Area Network (WAN), or other network to which the computer system 300 connects. The memory 308 may include one or more of a main memory 304, a read only memory 306, and a mass storage 307. The memory 308 may also include and/or be coupled to a removable storage media 305. Main memory 304 may be Random Access Memory (RAM), or other dynamic storage device(s). Read only memory 306 may be one or more static storage device(s) (such as, for example but not limited to, Programmable Read Only Memory (PROM) chips), for storing static information such as processor-executable instructions for the at least one processor 302, for example. Mass storage 307 may be used to store information and processor-executable instructions. For example, hard disks such as the Adaptec® family of SCSI drives, an optical disc, an array of disks such as RAID (e.g. the Adaptec family of RAID drives), or other mass storage devices may be used, for example. Bus 301 communicatively couples processor(s) 302 with the other memory, storage and communication blocks. Bus 301 may be a PCI/PCI-X or SCSI based system bus depending on the storage devices used, for example. Removable storage media 305 may include one or more of external hard-drives, floppy drives, flash drives, zip drives, compact disc-read only memory (CD-ROM), compact disc-re-writable (CD-RW), and digital video disk-read only memory (DVD-ROM), for example. The computer system 300 may further include an input device 311 and an output device 310. The input device 311 may include one or more of a keyboard, a microphone, and a mouse, joystick, trackball, or other pointing device. The processor 302 may control the input device 311 to capture user input. The output device 310 may be a one or more of a display, a speaker, and a haptic device. The display may provide a graphical user interface (GUI). The display may be, for example, but not limited to, a liquid crystal display (LCD) and/or a light emitting diode (LED) display. The processor 302 may control, respectively, the output device 310 to provide one or more of visible information, audible information, haptic information, numerical information, textual information, and graphical information. In an implementation the input device 311 and the output device 310 may be combined as an input/output device capable of capturing user input. For example, the input/output device may be a touchscreen.

In an implementation, the processor 302 may generate information for display by a remote output device 310. For example, a processor 302 located at a server may generate display information and provide the display information to a remote computing device. The display information may be configured such that a processor 302 located at the server can control an output device located at the remote computing device to display the display information generated by the server.

The components described above are meant to exemplify some types of possibilities. In no way should the aforementioned examples limit the scope of the disclosure, as they are only exemplary embodiments of computer system 300 and related components.

According to some embodiments of the present disclosure, the enterprise application server 128 includes one or more algorithms, and/or one or more analysis tools, for processing and/or displaying and/or aggregating the data received from the treatment monitoring system 10 to permit the enterprise system user 124 to evaluate, based on a summary or report or page or dashboard from the enterprise application server 128 to the computing device 122, the performance of the services in the treatment environment 101. For example, the reports or pages illustrated and described below with respect to FIGS. 4-13 may display information generated by the enterprise application server 128 and provided to the computing device 122 and/or the computing device 132. The computing device 122 and/or 132 may display the display information received from the enterprise application server 128. According to some embodiments of the present disclosure, the functions of any processor described herein may be performed across multiple processors and/or by multiple devices; hence, the enterprise application server 128 may actually be a combination of servers, and/or its functions may be distributed across two or more servers, for example across the enterprise application server 128 and the enterprise storage server 126.

Figure 4:
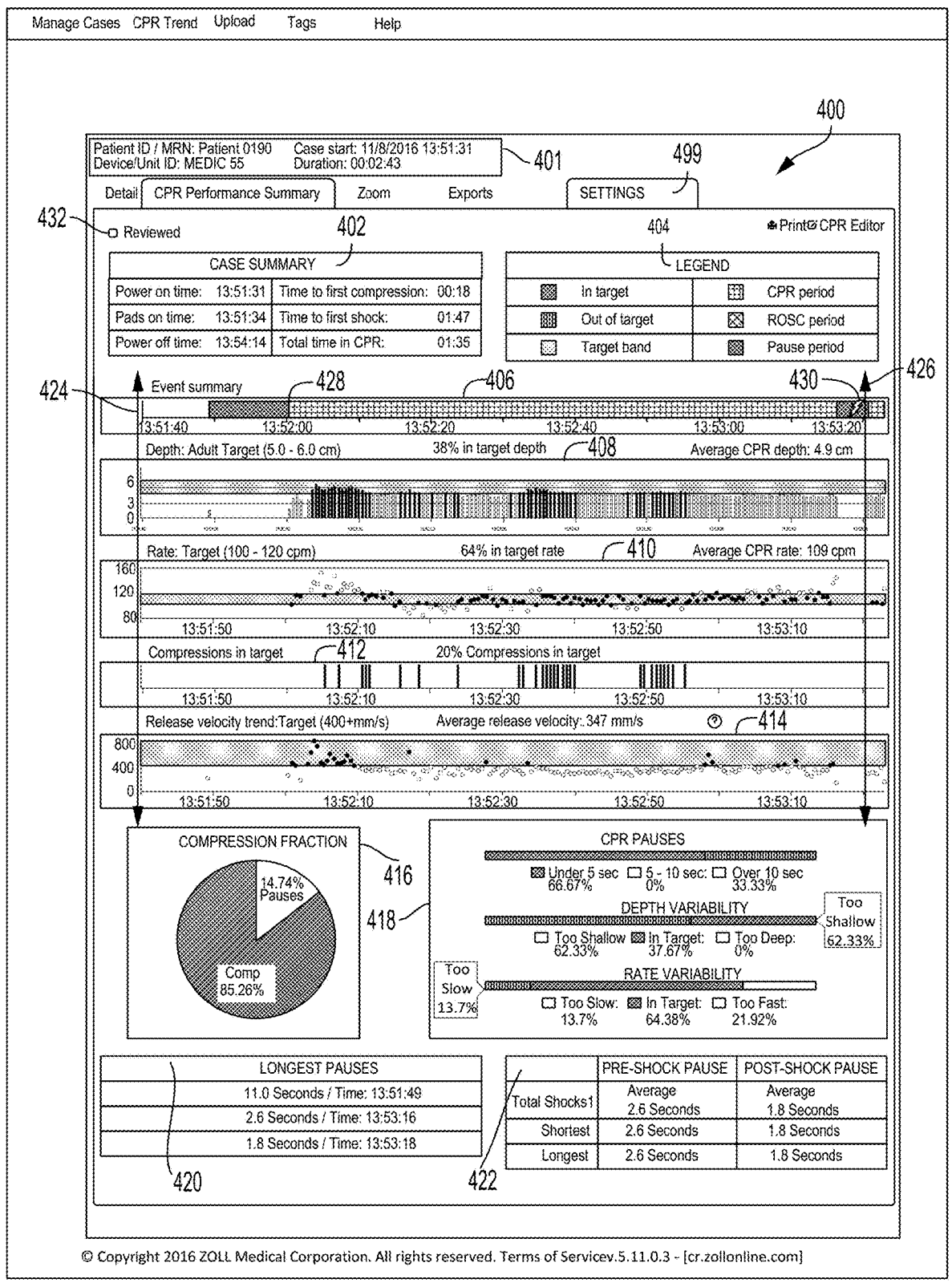
FIG. 4 illustrates a case review dashboard according to embodiments of the present disclosure.

Referring to FIG. 4 an example of a case review dashboard 400, according to embodiments of the present disclosure, is shown. Portions of the dashboard 400 are reproduced in enlarged format in FIGS. 5-7. According to some embodiments of the present disclosure, one or more of the metrics and/or statistics presented in the dashboard report of FIG. 4, for example, may be calculated and/or stored in advance of the display of the dashboard report at the computing device 122. Additionally, or alternatively, one or more metrics and/or statistics presented in the report of FIG. 4 may be calculated and/or generated at the time when the enterprise system user 124 requests the case report via the computing device 122. For example, the memory 308 of the enterprise server 128 may include processor-executable instructions configured to cause the one or more processors 302 of the enterprise server 128 to generate the dashboard 400 and provide the dashboard 400 as display information to one or more of the computing devices 122 and/or 132. Further the processor-executable instructions are configured to cause the one or more processors 302 to perform data handling procedures provided with, by, and for the dashboard 400 (e.g., downsampling, process control and improvement, capture of user input to the dashboard 400, storage and/or receipt of data from the treatment monitoring system 10, control of an output device to provide the dashboard 400, time synchronization of data, determination of performance metrics, statistical analyses of data, automatic determination of time periods within a case, and/or other data handling, processing, presentation, and/or analysis procedures described herein). The enterprise server 128 may receive treatment data from one or more treatment environments and may generate the dashboard 400 based on the received treatment data. The treatment data may represent treatment performance of an individual caregiver, a group of caregivers (e.g., a caregiver organization), and/or multiple groups of caregivers (i.e., multiple caregiver organizations).

The top of the dashboard 400 includes a dashboard summary 401, which may include a patient identification or other medical record number, an identification of one or more of one or more devices, one or more caregivers, and a caregiver organization used during the case, the date and time when the case began, and the duration of the case, according to embodiments of the present disclosure. The dashboard 400 may also include a case summary 402, which may list or summarize a power on time, a pads on time (time at which electrode pads were applied to the patient's chest), power off time, time to first chest compression, time to first defibrillator shock, and total time in CPR, according to embodiments of the present disclosure. According to some embodiments of the present disclosure, the event summary 406 provides a high-level overview of the case, conveying to the user the events that were occurring over the course of the case. The events may include CPR activities. The dashboard 400 may also include a "reviewed" checkbox 432—this checkbox permits the user to select the checkbox to indicate that the particular event was manually reviewed; this permits the record to be sorted based on the checkbox, as described below with respect to the trend report of FIG. 8. The dashboard 400 may further include an event summary 406, a chest compression depth summary 408, a chest compression rate summary 410, a compressions-in-target summary 412, and/or a release velocity trend summary 414, according to embodiments of the present disclosure. The dashboard 400 may also include a legend 404 that identifies the meaning of colors and/or symbols used in the dashboard 400, according to embodiments of the present disclosure. The various cross-hatch patterns in FIG. 4, and similarly in FIGS. 5-7, 10-13, 15-17, used to render these figures in black and white correspond to various colors on a color display. Therefore, a particular pattern is referred to herein as "color" since the color display can render the pattern as a color. The legend 404 may associate particular colors with particular quality indicators for rescue parameters and/or with particular time periods.

Figure 5:
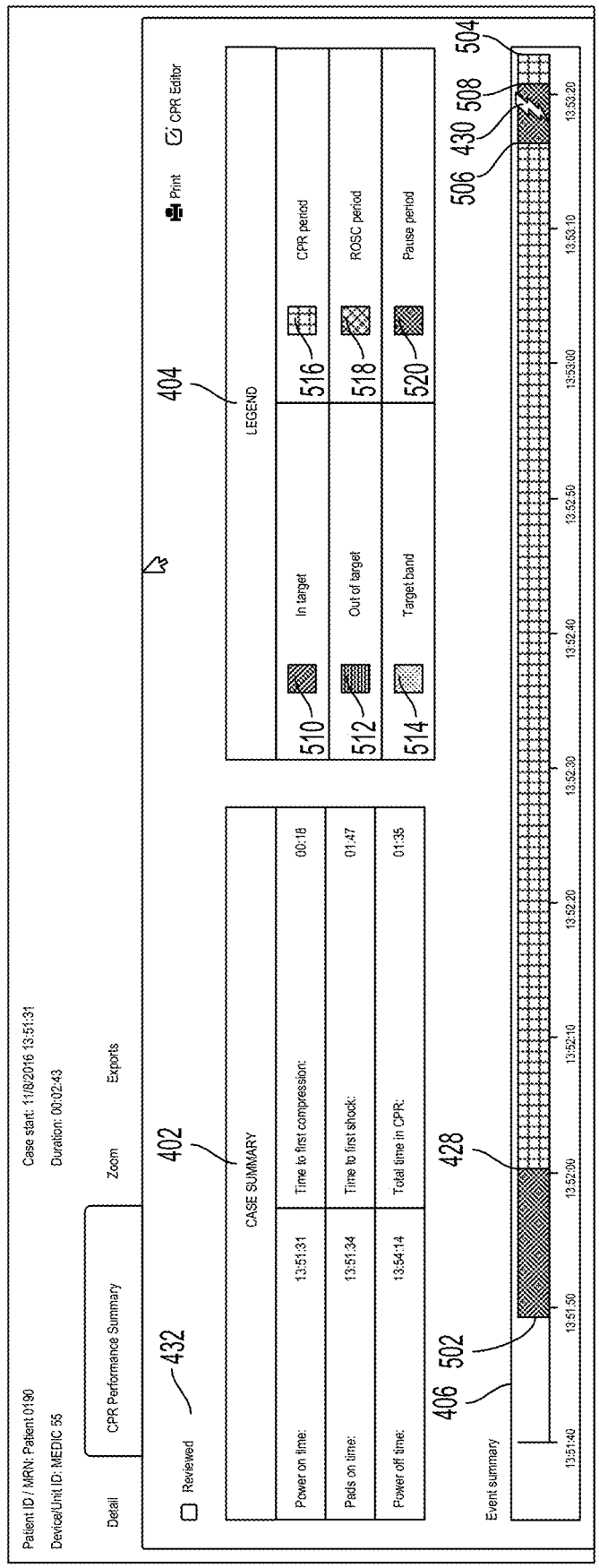
FIG. 5 illustrates an enlarged portion of the case review dashboard of FIG. 4, according to embodiments of the present disclosure.

Referring for example to FIG. 5 with further reference to FIG. 4, the colors 510 and 512 may indicate that rescue parameter data, such as, for example, a measured chest compression depth or measured chest compression rate, is within a target range or outside of a target range. The color 514 may indicate a target range for a rescue parameter.

In an implementation, the target range for the rescue parameter may be a predetermined range provided by the dashboard 400 (i.e., provided by the processor-executable instructions that generate the dashboard 400). For example, as discussed in detail below, the dashboard 400 may provide a target range for one or more of chest compression depth, chest compression rate, and release velocity. The predetermined range may be based on resuscitation guidelines and/or protocols from, for example, the American Heart Association (AHA) or another resuscitative care authority for a particular jurisdiction, country, or organization. Additionally, or alternatively, the predetermined range may be a range recommended by and/or determined by a provider, manufacturer, or distributor of the dashboard 400. For example, the range for a particular parameter may be based on results of clinical studies, resuscitation provider experience or expertise, physician recommendations, etc. In an example, the predetermined range may be a fixed range that is non-adjustable by the user of the dashboard 400. In a further example, the predetermined range may be a default range and may be a user adjustable range. In an implementation, when a customer account is established in order to access the dashboard 400, the provider of the dashboard 400 may set the fixed range and/or the default range corresponding to the customer's country, jurisdiction and/or organization or based on a customer requested default. For example, for a customer in the United States of America, the provider of the dashboard 400 may set the fixed range and/or the default range for the rescue parameter according to a current AHA guideline. However, as the fixed range and/or the default range is adjustable by the provider, the provider may adjust and/or update the fixed range and/or the default range to accommodate new and/or updated guidelines from the resuscitative care authority. For a user adjustable range, the provider of the dashboard 400 may provide a default range, as discussed above, and the user may adjust this range. In this way, the dashboard 400 may be customized to the needs of a particular user. For example, the user may set ranges during set-up of the customer account for dashboard access. As another example, the dashboard 400 may provide a settings tab 499. The user may select the settings tab to access adjustable customer settings for the dashboard 400. In an implementation, the fixed range and/or the default range may be a range corresponding to a first patient population and the provider and/or the user may adjust this range to customize the dashboard 400 to a second patient population. The patient population may correspond to patient age, patient physiological condition, etc. For example, the fixed range and/or the default range may correspond to adult resuscitation guidelines. For a particular customer(s), the provider of the dashboard 400 may change the fixed range and/or the default range to correspond to pediatric or infant resuscitation guidelines. As another example, the provider may set a default range for adult guidelines and the user may adjust the range to correspond to pediatric guidelines or vice versa.

Figure 6:
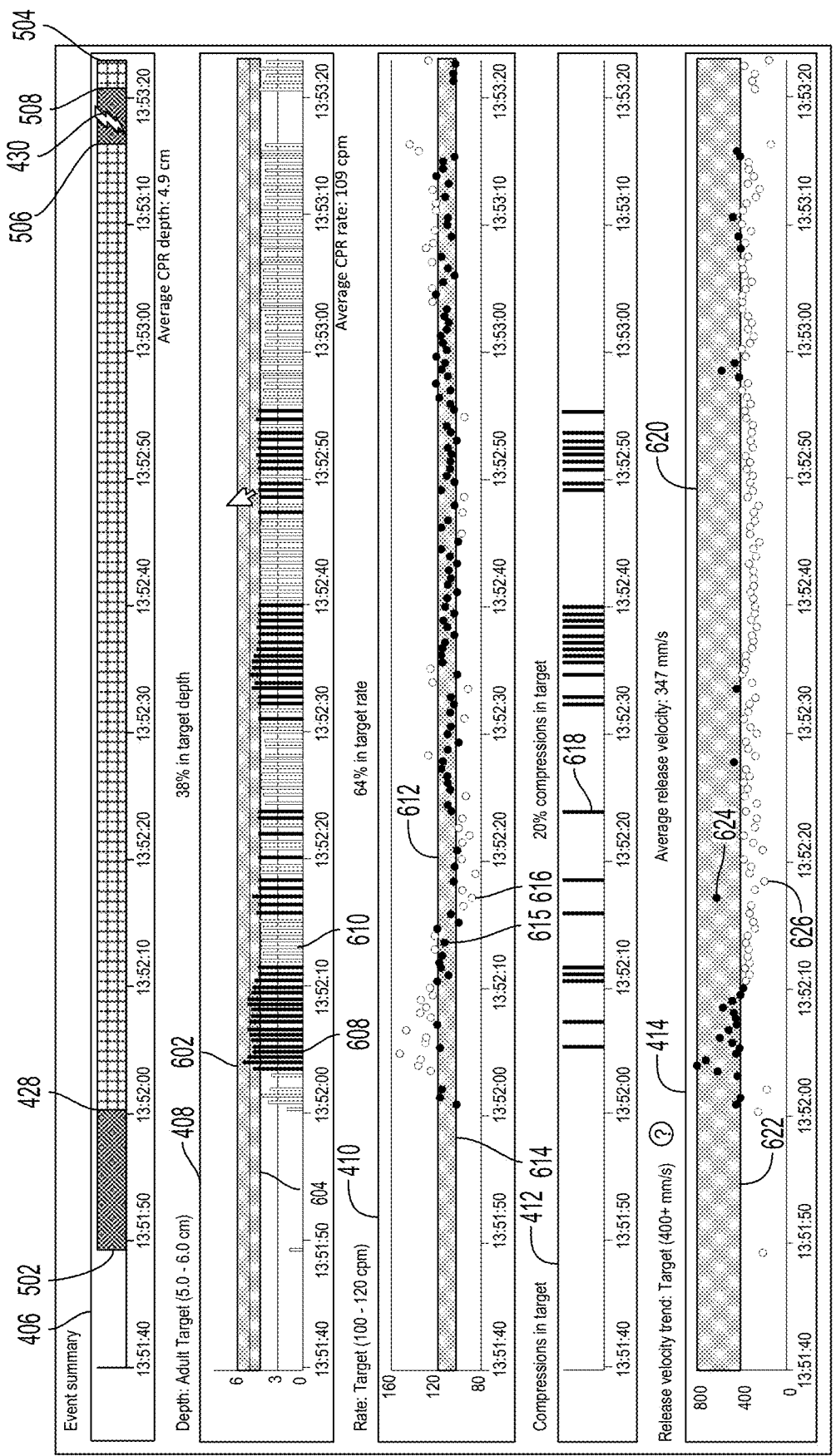
FIG. 6 illustrates an enlarged portion of the case review dashboard of FIG. 4, according to embodiments of the present disclosure.

Referring to FIGS. 4 and 6, an example of a chest compression depth summary 408 may be in the form of a plot of each chest compression, with the horizontal axis (as shown) being time, and the vertical axis being depth (e.g. in centimeters, as shown), according to some embodiments of the present disclosure. Along the vertical axis, the plot may indicate a top limit 602 for a chest compression depth and a bottom limit 604 for the chest compression depth. Between the limits 602, 604 may be color 514 from the legend 404 (as shown in FIG. 5) indicating the "target band." The target band between the bottom limit 604 and the top limit 602 is the target depth range for chest compressions. A series of chest compressions constitutes an example of an event during the case. Each chest compression during the event is indicated by a bar on the plot; the chest compressions that were deep enough to fall within the target depth range may be indicated in one color or pattern (e.g. chest compression 608 indicated in color 510 from legend 404 as shown in FIG. 5), and the chest compressions that were not deep enough (or were too deep) to fall within the target depth range may be indicated in another color or pattern (e.g. chest compression 610 indicated in color 512 from the legend 404 as shown in FIG. 5). The chest compression depth summary 408 may include a text indication of the target depth range, for example "Adult Target (5.0-6.0 cm)" as well as a textual summary of the plot, for example "38% in target depth" indicating the percentage of chest compressions for the event that fell within the target depth range, and "Average CPR depth: 4.9 cm" indicating an average CPR depth for the chest compressions for the event. In this example, the target range corresponds to an AHA guideline range for the compression depth. As discussed above, the target range shown on the dashboard 400 may be a fixed range (i.e., non-adjustable by the user of the dashboard) or may be a user-adjustable range. For example, 5.0-6.0 cm may be a default range from the provider of the dashboard 400 and the user may adjust this range to other upper and lower limits. The target range shown may be the default range or may be the user-selected range. As the 5.0-6.0 cm range is indicated as an adult target range for compression depth, in an implementation, the user of the dashboard and/or the provider of the dashboard may change this range to correspond to a range appropriate for pediatric or infant patients. According to some embodiments of the present disclosure, the chest compressions are displayed as extending downward (from top to bottom) from a zero axis to the particular reading value, instead of extending upwardly (bottom to top) from a zero axis to the particular reading value as shown in the chest compression depth summary 408, and may be shown in a number of other orientations and/or representations on any of the graphs, plots, or summaries shown and described herein. The targets and target ranges shown in the figures and discussed herein are examples only and not limiting of the disclosure. Other values for these targets and ranges are possible and within the scope of the disclosure.

The chest compression rate summary 410 may be in the form of a plot of each chest compression, with the horizontal axis (as shown) being time, and the vertical axis being chest compression rate (e.g. in compressions per minute, as shown), according to some embodiments of the present disclosure. The plot may indicate a target rate range between a top limit 612 for the chest compression rate and a bottom limit 614 for the chest compression rate along the vertical axis. This target band between the limits 612, 614 may be the color 514 from the legend 404. Each chest compression during the event is indicated by a circle or dot on the plot; the chest compression rate during each chest compression may be plotted as an average chest compression rate computed over a period of time before and/or after the chest compression, according to some embodiments of the present disclosure. The chest compressions that were performed at a rate within the target rate range may be indicated in one color or pattern (e.g. chest compression 615 indicated in color 510 from legend 404), and the chest compressions that were performed at a rate that was either higher than or lower than the target rate range may be indicated in another color or pattern (e.g. chest compression 616 indicated in color 512 from legend 404). The chest compression rate summary 410 may include a text indication of the target rate range, for example "Target (100-120 cpm)" as well as a textual summary of the plot, for example "64% in target rate range" indicating the percentage of chest compressions for the event that fell within the target rate range, and "Average CPR rate 109 cpm" indicating an average chest compression rate for the event.

Embodiments of dashboard may include, in addition to chest compression depth and rate summaries, additional CPR parameter summaries, for example a summary of a parameter related to chest release. The parameter related to chest release may be a parameter determined per compression based on data collected from the CPR metrics device 14. As one example, as in FIG. 6, release velocity measured during the administration of chest compression may be included in a separate plot. As another example, the dashboard 400 may be configured to display the parameter related to chest release for a particular compression as part of a hover tool. For example, a user of the dashboard 400 may hover the cursor over a compression bar on, for example, the compression depth plot 408. In response to this hover operation, the dashboard 400 may display a window (e.g., the window 1999 in FIG. 19) indicative of the parameter related to chest release, for example, the release velocity. As further examples, the parameter related to chest release may be displayed as an average value over a case and may include other statistical measures. This parameter may be displayed as text and/or as a graphic icon.

A release velocity trend summary 414 may be in the form of a plot of each chest compression, with the horizontal axis (as shown) being time, and the vertical axis being chest compression release velocity (e.g. in millimeters per second, as shown), according to some embodiments of the present disclosure. The plot may indicate a target release velocity range between a top limit 620 for the release velocity and a bottom limit 622 for the release velocity along the vertical axis. This target band between the limits 620, 622 may be color 514 from the legend 404. Each chest compression during the event is indicated by a circle or dot on the plot, according to some embodiments of the present disclosure. The chest compressions that were performed with a release velocity within the target release velocity range may be indicated in one color or pattern (e.g. chest compression 624 indicated in color 510 from legend 404), and the chest compressions that were performed with a release velocity that was either higher than or lower than the target release velocity range may be indicated in another color or pattern (e.g. chest compression 626 indicated in color 512 from legend 404). The release velocity trend summary 414 may include a text indication of the target range, for example "Target (400+ mm/s)" as well as a textual summary of the plot, for example "Average release velocity: 347 mm/s" indicating an average chest compression release velocity for the event.

In the above example of release velocity, the target range of "400+ mm/s" indicates a minimum release velocity. In other words, the target release velocity is greater than or equal to 400 mm/s. The upper limit shown in FIG. 4 for target release velocity may correspond to a historically observed target range boundary. For example, release velocities may be measured for a group of practitioners over a time period and the highest observed release velocity may be selected as the upper limit in FIG. 4. As another example, the provider of the dashboard 400 may set the upper limit as a multiple of the lower limit that is large enough to cover an expected range during performance of CPR by care providers. This procedure may be applied to any resuscitation parameter for which current clinical knowledge indicates a minimum recommended value or a maximum recommended value for the parameter but does not indicate a target range.

As an example, a target release velocity may be determined based on an analysis of historical clinical data. For example, one or more data sets may include release velocity during CPR along with the clinical outcome of the administered CPR (e.g., ROSC, patient survival, etc.). This data may be statistically analyzed using the dashboard 400 and/or in an analysis separate from the dashboard 400. In an example, a logistic regression may be performed in order to determine a regression equation that estimates a probability of a positive medical outcome for the patient as a function of release velocity. From this equation, a target for the release velocity (e.g., a target release velocity, a target range for the release velocity, a target minimum release velocity, and/or a target maximum release velocity) may be determined. The dashboard 400 may include this determined target as a default value.

The compressions-in-target summary 412 may be in the form of a plot of chest compressions that fall within both the depth targets and the rate targets, according to embodiments of the present disclosure. For example, chest compression 618 is within both the depth target in the chest compression depth summary 408 and the rate target within the chest compression rate summary 410, and is therefore included in the compressions in target summary 412. The chest compression 618 may be indicated in the color 510 from legend 404 indicating that it is within both targets. The compressions-in-target summary 412 may also include a textual summary of the plot, for example "20% compressions in target" indicating the percentage of the chest compressions that fell within both the depth target and the rate target, according to some embodiments of the present disclosure.

Referring again to FIG. 5, the colors 516, 518, and 520 in the legend 404 may indicate time periods during a case, such as, for example, CPR period(s), ROSC period(s), and pause period(s). For example, the "pause period" corresponds to one or more time periods during a case during which chest compressions are not performed and the "CPR period" corresponds to a time period during which chest compressions are performed.

In order to indicate these time periods, the processor-executable instructions that generate the dashboard 400 (e.g., instructions implemented by the enterprise server 128) may include instructions that implement an algorithm to automatically identify the CPR periods and the pause periods. This may provide the advantage of enabling analysis and CPR metrics feedback prior to a reviewer of a case manually identifying these periods.

An example of this algorithm may implement the following procedures. The algorithm may identify a series of chest compressions corresponding to a "CPR period" based on signals from the CPR metrics device 14. The algorithm may distinguish between signals correspond to CPR chest compressions, as opposed to spurious signals that do not correspond to CPR chest compressions. For example, a spurious signal may correspond to movement of the CPR metrics device 14 while a care provider is putting the CPR metrics device 14 in place on a patient. The spurious signal may resemble a signal generated during a chest compression but in fact may be due to a singular transient movement of the CPR metrics device 14 rather than an intentionally performed CPR chest compression. The algorithm may prevent the signal generated from this singular transient movement from being incorrectly identified as a signal corresponding to a first chest compression in a series of CPR chest compressions.

The series of CPR chest compressions may be identified as a group of a minimum number of compressions occurring at a minimum rate and corresponding to a minimum depth. More than one compression is needed in order to establish a rate. For example, the minimum number of compressions may be three, the minimum rate may be 60 compressions per minute and the minimum compression depth may be 0.75 inches (1.9 cm). In other words, the series may be identified for an occurrence of at least three compressions with a compression rate of greater than or equal to 60 cpm and a compression depth of greater than or equal to 0.75 inches (1.9 cm). Thus the CPR period may include at least three compressions (e.g., the number of compressions in the automatically identified CPR period is greater than or equal to three). The values of three compressions, 60 cpm, and 0.75 inches (1.9 cm) are examples only and not limiting of the disclosure. Once a series of CPR chest compressions is identified, the algorithm may determine a start time and a stop time for the CPR period within the case. The start time may be a time that is a set time interval before the time of the first compression of the series. For example, the start of the CPR period may be at a time that is 1 millisecond prior to the time of the first compression of the identified series. The first compression in the identified series is the first of aa set of at least three compressions at a particular rate and depth. The stop time of the CPR period may be a time that is a set time interval after the time of the last compression of the series. The last compression is the last of a set of at least three compressions at a particular rate and depth. For example, the stop time of the CPR period may be at a time that is 1 millisecond after the time of the last compression.

As a further example of the algorithm procedures, the algorithm may identify the pause periods. The pause period may be identified based on an absence of identified CPR chest compressions for a particular minimum time period. The particular minimum time period may be a fixed value set by the dashboard 400. Alternatively, the dashboard 400 may provide a default value for this time period and the default value may be user-configurable. The dashboard 400 may provide editing tools for adjustment of this time period and other user configurable settings. These editing tools may be accessed via the settings tab 499 and/or may be made available by user editable display fields on the dashboard 400. For example, a user may click on a field shown on the dashboard (e.g., the target depth, the target rate, chest compression pauses, etc.) and the dashboard 400 may provide editing options in a window, for example, an overlay window. For example, the user may input values for target ranges for treatment parameters (e.g., user configurable target ranges) based on process control and improvement analyses described below with regard to FIGS. 14A-14D. In an example implementation, the particular minimum time period may be two seconds. In this example, if a time interval between identified CPR chest compressions is greater than or equal to two seconds, then this time interval is determined to be a pause period. The identified chest compressions are those compressions in the series of compressions determined to be CPR chest compressions as described above.

For example, the event summary 406 includes a timeline of a case for which CPR is being summarized and indicates events that occurred at various points in time along the timeline of the case. The beginning of the timeline at 502 (from 502 to 428) is the color 520 for a pause period event, indicating that chest compressions were not being performed in that period. From time 428 to time 506, the timeline in the event summary 406 is the color 516 corresponding to the CPR period in the legend 404, indicating that chest compressions were being performed during that time window (i.e., indicating a CPR chest compression event). Between times 506 and 508, another pause period event (e.g., as shown with the color 520) is indicated, along with a shock signal 430. The shock signal 430 indicates that a defibrillator shock event occurred at the corresponding time on the timeline. In this example, the shock signal 430 overlaps the pause period event between times 506 and 508 indicating that the defibrillations shock was applied to the patient during the pause period (i.e., chest compressions were paused or stopped in order to accommodate the shock event). The timeline ends at time 504.

According to some embodiments of the present disclosure, the dashboard 400 may display CPR performance simulation metrics. The CPR performance simulation metrics are determined from CPR performance simulation data collected when the treatment monitoring system 10 is used with a mannequin and/or in a practice, training, or other CPR performance simulation (i.e., performance of CPR techniques on an object or on a subject that is not a victim of an adverse medical condition). In such cases, the data collected may be tagged with one or more tags that indicate that the data was collected as part of training or simulation. The CPR performance simulation data may include diastolic simulation data and systolic simulation data. The diastolic simulation data refers to, for example, data collected during, about, or pertaining to the release portion of the chest compression cycle and may include release velocity and/or other chest release parameters. The systolic simulation data refers to, for example, data collected during, about, or pertaining to the compression portion of the chest compression cycle. For example, systolic simulation data may include chest compression depth, and diastolic simulation data may include chest compression release velocity, according to embodiments of the present disclosure. As such, in an example, the release velocity trend summary 414 may include diastolic simulation data and the depth and rate trend summaries 408, 410, and 412 may include systolic simulation data.

The CPR performance simulation data may also include other data available from the treatment monitoring system during a simulation of treatment. For example, the CPR performance simulation data may include ventilation simulation data, medical device simulation data, and/or patient charting device simulation data. These simulation data may include data collected during simulation of treatment practices. This data may be collected based on techniques performed by humans learning and/or practicing treatment practices and/or based on data generated by a computing device and/or a simulated and/or computer-operated medical treatment tool and/or sensor.

The chest compression depth, rate, and release information may be monitored by one or more CPR metrics devices 14 during the event. Additional data may be monitored, plotted, and/or summarized in the dashboard 400. The dashboard 400 may be configured to concurrently display multiple time-based plots of CPR metrics and/or additional data. The concurrent display refers to a display for which there exists at least a period of time during which two or more graphical representations of the CPR metrics and/or the additional data are displayed together. The two or more graphical representations may be side-by-side, superimposed, or one above the other (e.g., as shown in the example of FIG. 4). Further, the concurrent graphical representations may include shading and/or icons for first information that indicates a time synchronization of the first information with the concurrently displayed second information. For example, a shaded area representing chest compression delivery may be overlaid on an ECG waveform such that the overlay indicates the time during the ECG waveform at which the chest compressions occurred. These multiple time-based plots of CPR metrics may be aligned along at least a common and/or shared time axis, e.g., a single time scale used twin the display of multiple parameters to facilitate comparison of time trends for the multiple parameters. The common time axis may be used in the display of data for two or more equal time intervals (e.g., each interval represented by a tick mark) over a particular and equal time duration. For example, in FIG. 4, the data is displayed over an approximately two-minute time duration (e.g., 13:51:40 to 13:53:20) at 10 second time intervals for the event summary, the compression depth, the compression rate, the compressions in target, and the release velocity. In the example of FIG. 4, the event summary 406, the chest compression depth summary 408, chest compression rate summary 410, compressions-in-target summary 412, and release velocity trend summary 414 are all aligned along the common timeline (e.g. the vertical arrow 424 intersects each plot at approximately 13:51:40 during the event, and vertical arrow 426 intersects each plot at approximately 13:53:20 during the event).

The concurrent display along with the common timeline may enable the user of the dashboard to readily make visual comparisons among the various summaries so as to observe how information in one summary may correlate with information in another summary. While each of the summaries 406, 408, 410, 412 in the dashboard 400 is shown extending between a common start time and a common end time, event-based summaries could have different beginning and end times yet still be displayed aligned with the common timeline, for example aligned along the vertical arrow 424 and/or 426, or another common reference point. And while the summaries 406, 408, 410, 412 are shown in vertical alignment, the summaries could alternatively be shown in horizontal alignment along a common timeline; alternatively, the timeline could be neither horizontal nor vertical.

Additional summary data could also be presented in the dashboard 400 report. For example, in one embodiment, the dashboard displays physiological data from a monitor that monitored the patient during the particular case being shown in the dashboard 400. Such a monitor may be a hospital-based patient monitor, according to some embodiments, and the physiological data may include invasive pressure data and carbon dioxide data from a hospital monitor, compiled along with data from a patient monitor and/or defibrillator.

According to some embodiments of the present disclosure, the data for the dashboard 400 may be received from a software application and database or other device that received patient monitor and/or defibrillator data from the medical device 18, for example wirelessly, and collects it and/or aggregates it before it is made available to the server 126 or 128 for use in generating the dashboard 400. For pediatric intensive care unit cases, at times clinicians titrate CPR quality to achieve target pressure or end-tidal carbon dioxide levels. In some embodiments, the aforementioned types of data are synchronized with the CPR data from a CPR metrics device 14 and the ECG data from a patient monitor and/or defibrillator for easy analysis.

Figure 7:
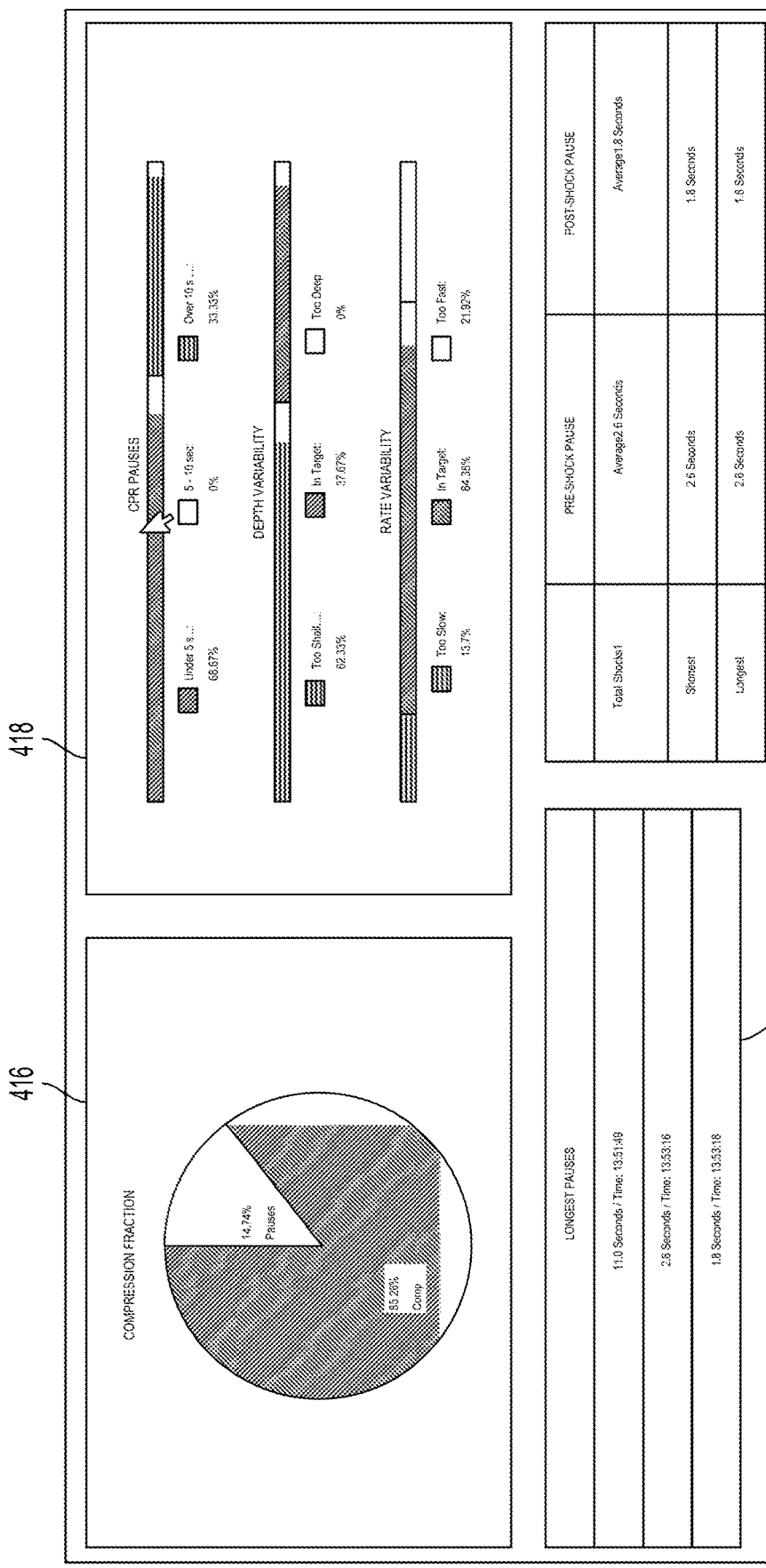
FIG. 7 illustrates an enlarged portion of the case review dashboard of FIG. 4, according to embodiments of the present disclosure.

As indicated in FIG. 7, the dashboard 400 may include additional summaries and/or statistics, such as a compression fraction summary 416 indicating a percentage of time when compressions were being applied over the case versus a percentage of time when the caregiver 114 was pausing. In an implementation, the compression fraction summary 416 may be represented as a pie chart. The compression fraction summary 416 shows the percentage of time in which chest compressions are done by rescuers during resuscitation from, for example, a cardiac arrest. Chest compressions may be interrupted or delayed by things such as rescue breaths, pulse checks and heart rhythm analysis. Fewer pauses in chest compressions may, in some cases, increase the chances of surviving a cardiac arrest. One section (e.g. the blue section) of the pie chart represents the percentage of time that CPR compressions were being performed, and the other section (e.g. the gray section) of the pie chart indicates the percentage of time that CPR compressions were not being performed.

A CPR pause length summary chart 418 indicates, for example, relative length of chest compression pauses in color code (e.g. under 5 seconds, 5-10 seconds, and over 10 seconds), depth variability in color code (e.g. too shallow, in target, and too deep), and rate variability in color code (e.g. too slow, in target, and too fast). Long pauses in chest compressions may lead to poorer outcomes for patients in cardiac arrest. The CPR pause length summary chart 418 shows information about pauses and how long they were. The depth variability chart shows in percentages how well the care givers did performing chest compressions related to the depth they achieved. The rate variability summary shows in percentages how well the caregivers did performing chest compressions at the target rate. The longest pauses summary 420 may indicate the length of the longest pauses and the time(s) during the event when they occurred. A pre-shock/post-shock summary 422 may indicate the total number of shocks, as well as the average, shortest, and longest pause both pre-shock and post-shock, according to embodiments of the present disclosure. In other words, the longest pauses summary 420 shows the three longest pauses that were detected during the case. It shows how long the pause was and at what time during the event it occurred. According to some embodiments of the present disclosure, clicking on or otherwise selecting the display of one or more pauses navigates the user to display a portion of the case that contains the long pause; similar navigation options are also possible for selecting pre- or post-shock pauses. The pre-shock/post-shock summary 422 shows, for example, the total number of shocks delivered during a case and how long chest compressions were paused immediately before and after the shock.

Figure 15:
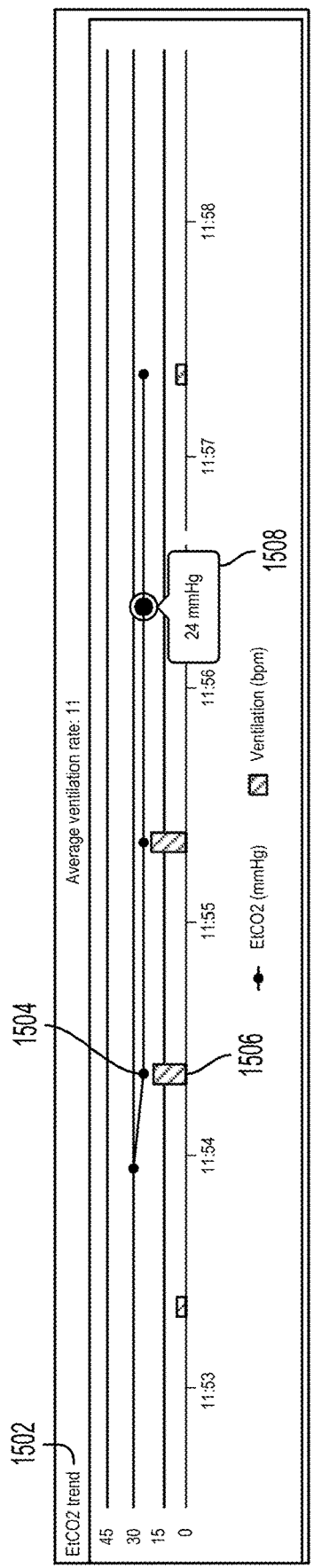
FIG. 15 illustrates an end-tidal carbon dioxide trend summary, according to embodiments of the present disclosure.
Figure 16:
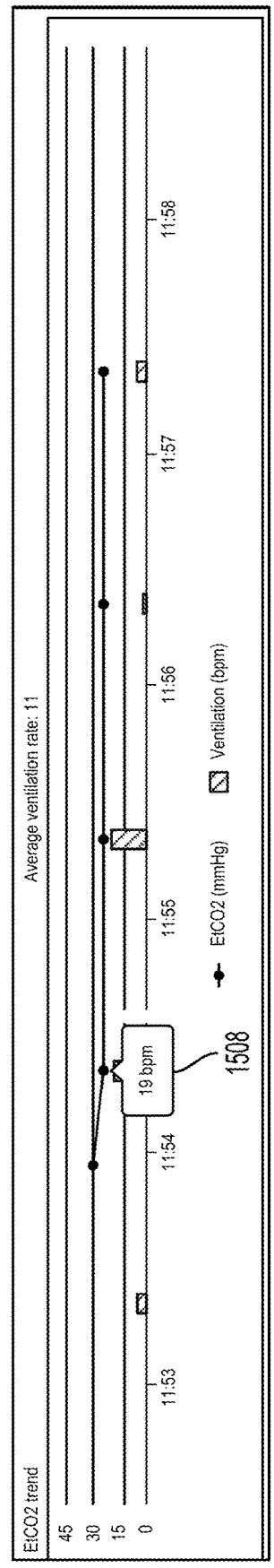
FIG. 16 illustrates an end-tidal carbon dioxide trend summary, according to embodiments of the present disclosure.

The dashboard 400 may include other summaries, including other time-based summaries, according to embodiments of the present disclosure. For example, an end-tidal carbon dioxide summary 1502 as illustrated in FIGS. 15 and 16 may be included, and may be arranged along with and/or in different combinations and/or sub-combinations with summaries 406, 408, 410, and 412, including along a shared and/or common time axis, according to embodiments of the present disclosure. The end-tidal carbon dioxide summary 1502 may include a time-based plot 1504 of end-tidal carbon dioxide values (e.g. in millimeters of mercury as shown), and may also include ventilation plots 1506 of the ventilation rate over the given time period (e.g. breaths per minute average over the one-minute time interval as shown). The time-based plot 1504 may be a line chart. Placing a cursor over one of the plotted end-tidal carbon dioxide values on the time-based plot 1504 or ventilation plots 1506 displays an information tab 1508 that states the value of the observed data point, as shown in FIGS. 15 and 16, according to embodiments of the present disclosure.

The time-based plot 1504 represents EtCO2 measured in mm/hg (this begins once EtCO2 measurement is being detected, for example), and may be the average EtCO2 measurement for the one-second time increment shown, or the EtCO2 measurement at the time indicated in the plot, according to embodiments of the present disclosure. The ventilations may be represented by a bar (e.g. a blue bar) in the middle of each minute. The bar represents, for example, a number of ventilations that were given to the patient in that particular minute (in breaths per minute). Average ventilation rate for the entire case may be displayed at the top of the chart. Alternatively, other time increments may be used for presenting the EtCO2 and/or ventilation data. Also, though FIGS. 15 and 16 illustrate ventilation data and EtCO2 data in the same plot or graph, one of ordinary skill in the art will recognize, based on the present disclosure, that one or the other of ventilation data and EtCO2 may be presented in a graph or plot or chart, instead of both, according to some embodiments. As mentioned above, a user may hover a cursor over any of the blue bars to view the specific number of ventilations given during that minute. Presenting EtCO2 and ventilation data in the manner shown in FIGS. 15 and 16 allows users to have access to data quickly, allows for briefing of caregivers 114 at a time period close to that of the event (which may be referred to as a "hot debrief"). According to some embodiments of the present disclosure, the user may clip or select a particular segment of any of the summaries 406, 408, 410, 412, 414, 1502 and save it for later review.

According to some embodiments of the present disclosure, the patient 116 may be treated by an automated CPR device, for example a ZOLL® AutoPulse® device. In such cases, the CPR compressions and rate are controlled by the device and are not manually applied by a caregiver 114. In such cases, the ZOLL® AutoPulse® device may include a data signature indicating its use in treatment, and/or the user may enter during the case and/or later in post-event case review, an indication that mechanical CPR was performed. In such cases, in one option the dashboard 400 deactivates one or more of the indication(s) relating to CPR performance (e.g. compression rate, depth, compressions in target, and release velocity) because such performance was accomplished by a machine, but shows the remaining potentially relevant summaries and/or data in the dashboard 400. In other cases, the same data may be displayed in the dashboard 400 as shown even for a mechanical CPR performance, in order for the reviewer to observe the physical performance of the mechanical CPR device, according to embodiments of the present disclosure.

Figure 8:
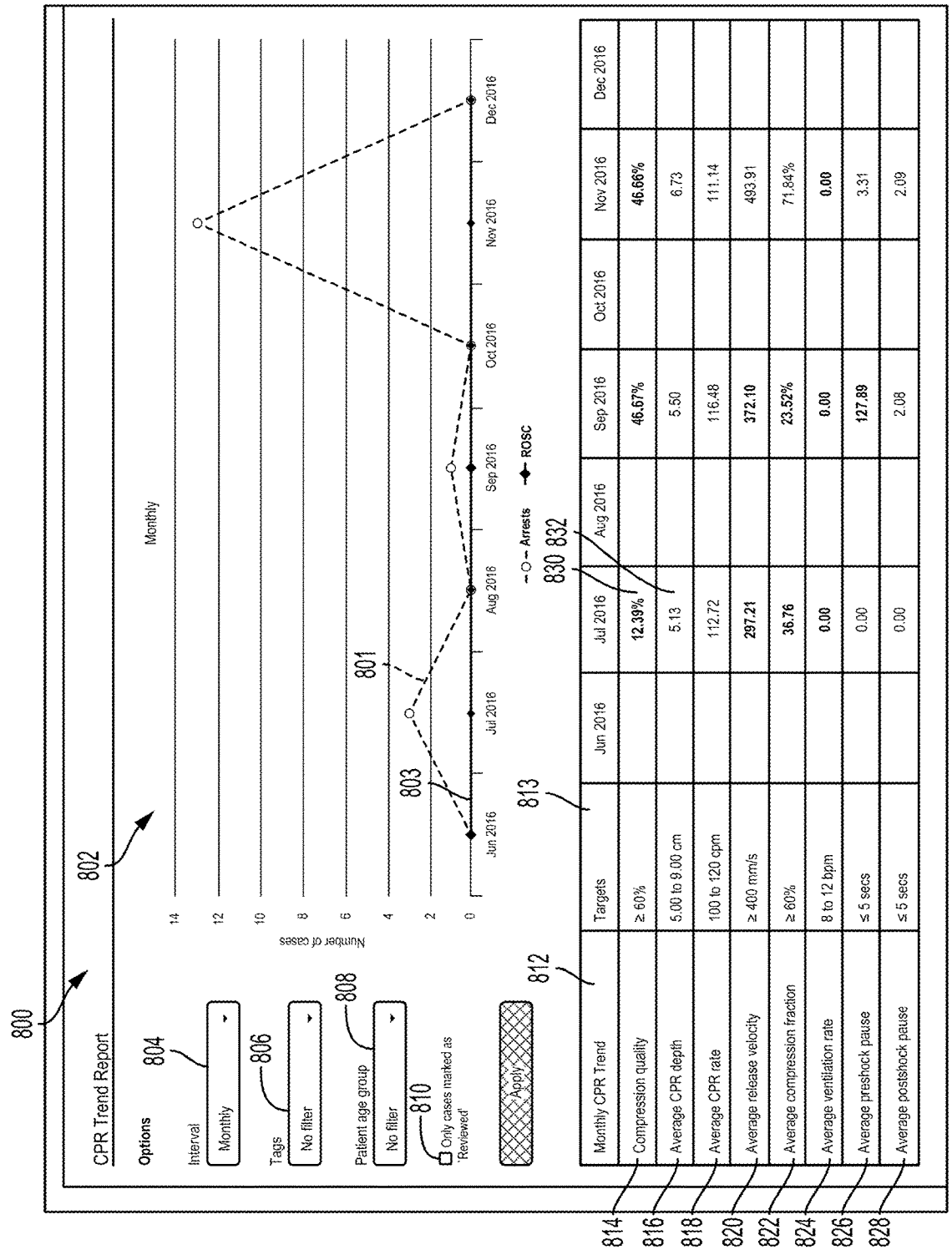
FIG. 8 illustrates a CPR performance trend report organized according to monthly intervals, according to embodiments of the present disclosure.
Figure 9:
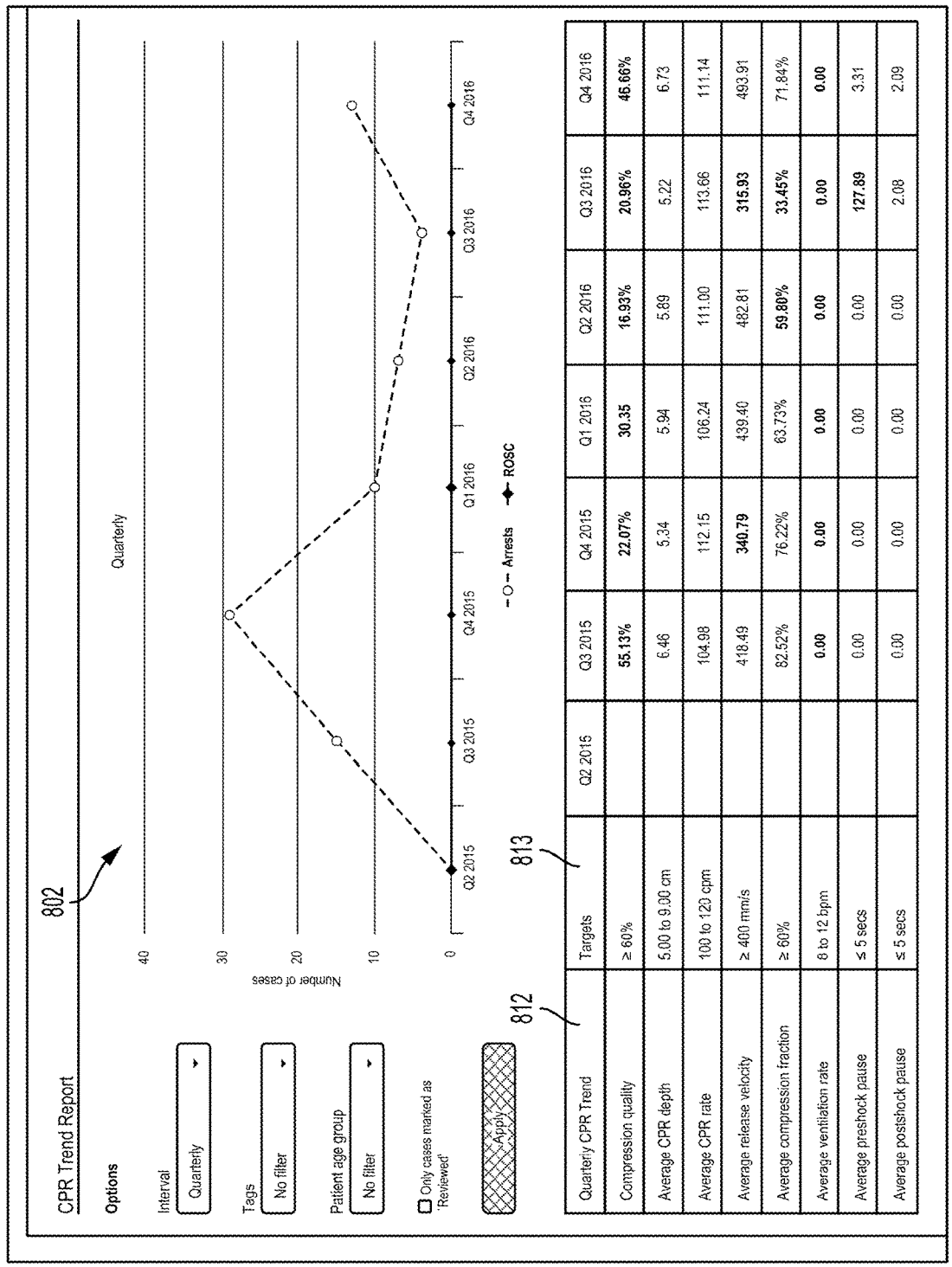
FIG. 9 illustrates the CPR performance trend report of FIG. 8 organized according to quarterly intervals, according to embodiments of the present disclosure.

FIG. 8 illustrates a CPR performance trend report 800 organized according to monthly intervals, according to embodiments of the present disclosure. While FIGS. 4-7 illustrate a manner of presenting case review data for a single case, FIGS. 8 and 9 illustrate a trend report 800 that provides performance analysis statistics across a set of two or more cases, and/or across a range of time. The CPR performance trend report 800 permits a quality assurance person or other user to observe whether certain CPR performance metrics are being met over particular periods of time or across certain sets of cases (e.g. cases filtered by a criteria), and/or to see trends in CPR performance metrics over time. The CPR performance trend report 800 includes one or more filter selections, which in one example may be in the form of a drop-down menu and/or drop-down checkbox selection format. For example, in the interval selection filter 804 (e.g., a time interval selection filter), the user may select a time period, for example daily, weekly, monthly, quarterly, and yearly. The treatment data may be aggregated according to the selected time period. A statistical measure for the treatment data may represent the treatment data for the selected time period. For example, if the selected time period is monthly, as shown in the example in FIG. 8, then the compression depth data from each month is aggregated and an average compression depth for the month is determined and displayed. The interval selection filter 804 may default to a certain value, for example monthly. The graph 802 shows a number of cases (e.g., a number of events of a particular type for which treatment data is available) on the y-axis within a time period on the x-axis. The number of cases per time period may indicate a frequency of the particular type of event. For example, line 801 indicates a number of cases of cardiac arrest events per time period. As another example, the line 803 indicates the number of cases or events in each time period that resulted in the return of spontaneous circulation (ROSC) for patients 116. The line 803 is flat at zero in the example of FIG. 8 and coincides with the x-axis.

The interval selected in the interval selection filter 804 is also the interval used in labeling the columns of the CPR trend table 812. Table 812 includes a row for each metric or statistic, which may be derived from an algorithm or other mathematical operation based on the selected data set. For each row, a targets column 813 identifies the target values and/or ranges for the data set; in other words, the desired performance values and ranges. For each metric, a value is provided for each time interval, which is the outcome of the particular metric for the particular time period. Color coding may be used to indicate whether the displayed value is above or below the desired or target value. For example, the compression quality value 830 for July of 2016 in FIG. 8 may be red because 12.39% is less than the target compression quality of 60%. The average CPR depth value 832 for July of 2016 in FIG. 8 may be green because 5.13 centimeters is within the target range of 5.00-6.00 centimeters for the average CPR depth, according to embodiments of the present disclosure.

Various numbers of rows and/or metrics may be reflected in the CPR performance trend report 800, according to embodiments of the present disclosure. A compression quality row 814 may summarize the percentage of overall chest compressions receiving a "passing" (as opposed to "failing") grade or evaluation, which may be defined subjectively according to a proprietary standard, and/or objectively according to published or industry accepted algorithms and/or definitions. An average CPR depth row 816 may summarize the average chest compression depth for the events within the data set for each interval. An average CPR rate row 818 may summarize an average chest compression rate for the events within the data set for each interval. An average release velocity row 820 may summarize an average release velocity of each chest compression in the data set for each interval. An average compression fraction row 822 may summarize the percentage of time of a chest compression cycle during which the chest is being compressed for each compression in the data set for each interval. An average ventilation rate row 824 may summarize, in breaths per minute, the average ventilation rate for each event in the data set for each interval. Such ventilation data may be gathered for each event with a ventilation metrics device 16, according to some embodiments. An average pre-shock pause row 826 may summarize an average period of time during which CPR is paused preceding a defibrillator shock, for each event in the data set for each interval. An average post-shock pause row 828 may summarize an average period of time during which CPR is paused following a defibrillator shock, for each event in the data set for each interval. Such pre-shock and post-shock pause data may be obtained from a combination of shock data from a medical device 18 and a CPR metrics device 14, according to embodiments of the present disclosure. According to some embodiments of the present disclosure, the report 800 of FIG. 8 may additionally or alternatively show measured and/or collected data, statistics (e.g., the mean, median, etc.) and/or other metrics for various resuscitation parameters across the interval. For example, the metrics rows 814, 816, 818, 820, 822, 824, 826, 828 display statistics and/or metrics for resuscitation parameters including compression quality, average CPR depth, average CPR rate, average release velocity, average compression fraction, average ventilation rate, average pre-shock pause, and average post-shock pause. These parameters are examples only and not limiting of the disclosure as other resuscitation parameters are within the scope of the disclosure.

When a user selects "quarterly" in the interval selection filter 804 and activates the "apply" button, the graph 802 readjusts to plot the same data over quarterly time intervals, and the table 812 readjusts to provide the metric summaries in columns that are labeled with quarterly intervals, as illustrated in FIG. 9, according to some embodiments of the present disclosure.

The CPR performance trend report 800 includes other filters, for example the tags filter 806. Tags may be applied to an event or case in order to identify it by type, for example to identify the case by, for example, but not limited to, a caregiver identification or a crew identification. One tag or multiple tags may be selected from the "Tags" filter 806 to review a set of cases sharing the selected tag(s) across the selected interval, according to embodiments of the present disclosure. The tags may be added during data capture, and/or during post-event case review, according to embodiments of the present disclosure. Tags may be added manually and/or automatically, according to embodiments of the present disclosure. For example, a particular caregiver identification may be selected. In this example, there may be 3 EMS workers associated with a facility, Bob Jones, Jane Doe, and Cathy Carter. The tag may select an identification such as a name or number associated with Cathy Carter. In this case, the data from the database 130 may be filtered so that the dashboard displays the performance trend report for the selected worker, i.e., Cathy Carter. As another example, a particular crew identification tag may be selected. The crew identification tag may indicate a particular shift of EMS workers (e.g., day shift, night shift, holiday shift, etc.). In this case, the data from the database 130 may be filtered so that the dashboard 400 displays the performance trend report for the selected crew identification tag.

According to some embodiments of the present disclosure, a portion of the case or event data may be collected while the CPR metrics device 14 is used with a mannequin, or in another practice, training, and/or CPR simulation situation. In such cases, the data collected may be tagged with one or more tags that signifies that the data was collected as part of training or simulation. Such tagging may occur automatically, for example if the CPR metrics device 14 and/or a subsequent recipient of the data recognizes that the data was acquired from the type of CPR metrics device 14 that would be used with or incorporated into a CPR mannequin. Such CPR metrics devices 14 may include, in the CPR performance data, a piece of information that identifies the CPR metrics device 14 as a practice or training device, for example. In other cases, such a tag may be added in post-event or post-case review, for example by a quality assurance reviewer or supervisor. In other cases, the CPR metrics device 14 may include a switch, setting, or other user selection option to indicate whether the CPR metrics device 14 is being used for a training scenario or not. The CPR performance trend report 800 may in some embodiments include an ability to select one or more tags to be filtered based on training/practice data, and/or one or more filters permitting the user to select a trend report format for a data set that includes only practice/training data, and/or only non-practice/training data, both, and/or neither. The Case review dashboard 400 of FIG. 4 may also indicate, for example visually, that the event or case involved acquisition of CPR performance or other data for a simulation and/or training exercise and/or practice exercise, for example in the dashboard summary 401, according to embodiments of the present disclosure.

The CPR performance trend report 800 may also include a patient age group filter 808, which permits the trend report 800 to be created for a data set involving the selected age group. The age group filter 808 selections may include, for example, adult, pediatric, and infant. The ability to filter by age group provides a particularly helpful filter when it comes to certain metric summaries; for example, the average CPR depth row 816 has targets that depend upon whether the case involved an adult patient, a pediatric patient, or an infant patient (because smaller body sizes involve shorter target CPR depth ranges). When the CPR performance trend report 800 is created, the non-adult records may be ignored in the data set, or alternatively if the non-adult records are included in the average CPR depth row 816 then the displayed averages may be skewed lower due to the pediatric and infant data. Thus, an ability to select a patient age group filter 808 allows the user to observe the trending for certain rows like the average CPR depth row 816 across a set of cases for patients having the same target values and ranges, according to embodiments of the present disclosure.

According to embodiments of the present disclosure, the enterprise system user 124 and/or the enterprise system administrator 134 may set or adjust the settings and/or parameters that define the patient ages for each age group that form the basis for age group filter 808, and unique settings may be created for each patient population. According to other embodiments of the present disclosure, an age group selection made on the CPR metrics device 14, the ventilation metrics device 16, and/or on the medical device 18 is passed along with the data from the CPR metrics device 14, the ventilation metrics device 16, and/or the medical device 18, and stored along with the data for inclusion in the age group filter 808.

The CPR trend report may further include a filter checkbox labeled "only cases marked as 'reviewed'" 810; this checkbox 810 permits the CPR performance trend report 800 to be created only using cases for which the Case review dashboard 400 has been manually reviewed, and the "reviewed" checkbox 432 checked.

In an implementation, the dashboard 400 may include a caregiver filter. The caregiver filter may enable the user of the dashboard to select one or more individual caregivers and/or one or more groups of caregivers. The caregivers may be identified by the information in the dashboard summary 401.

Figure 10:
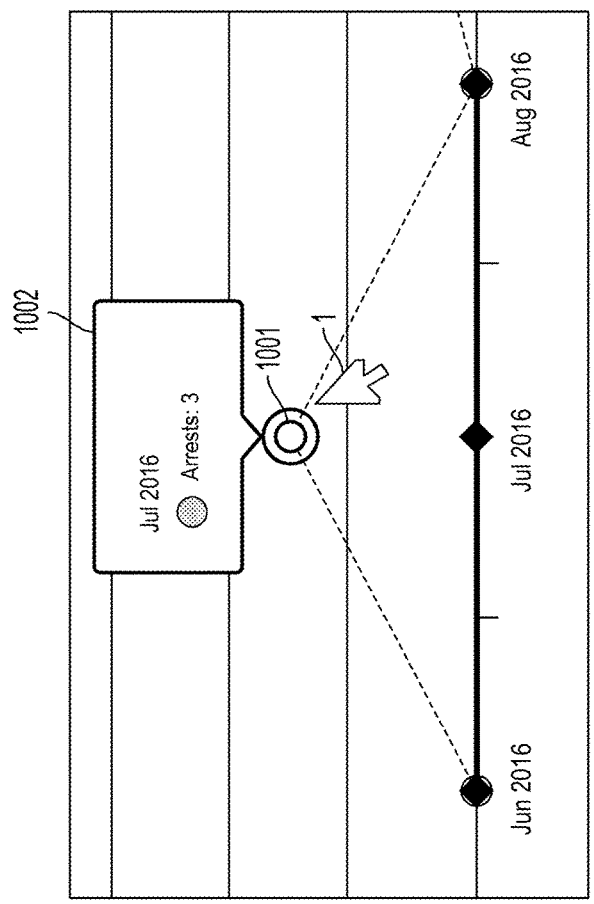
FIG. 10 illustrates an enlarged view of the CPR performance trend report of FIG. 8 when a cursor is placed over a node, according to embodiments of the present disclosure.

FIG. 10 illustrates an enlarged view of the CPR performance trend report 800 of FIG. 8 when a cursor 1 is placed over a node 1001 on the graph 802 of cardiac arrests, according to embodiments of the present disclosure. Each node, including, for example, the node 1001, corresponds to data associated with the node. When the cursor 1 is placed over the node, for example, the node 1001, a summary callout 1002 pops up to summarize the data associated with the node. For example, the summary callout 1002 provides a date, and a summary of the total number of arrests plotted at the node 1001, according to embodiments of the present disclosure. In this manner, the CPR performance trend report 800 may be dynamic and/or interactive. According to some embodiments of the present disclosure, selection of one or more of the metrics rows 814, 816, 818, 820, 822, 824, 826, and 828 plots the values over time of the selected metric or statistic, similar to examples discussed with regard to FIGS. 8 and 9. According to such embodiments, a user may toggle through the displays of the various metrics, and/or export the trend report 800 or the graph 802 for a report that may be shared with other users or presented easily.

Figure 11:
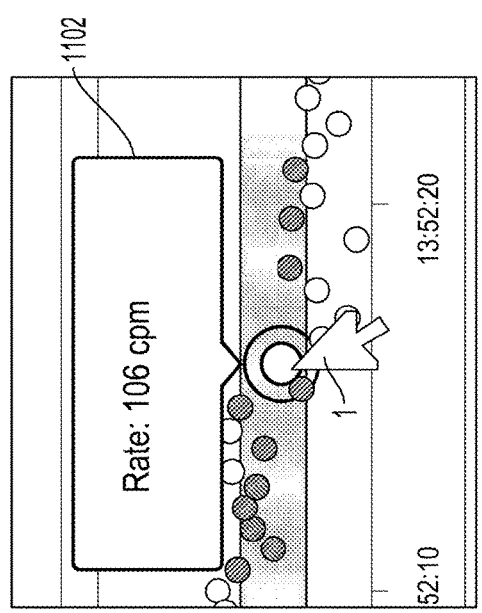
FIG. 11 illustrates an enlarged view of the case review dashboard of FIGS. 4 and 6 when a cursor is placed over a chest compression rate data point, according to embodiments of the present disclosure.

FIG. 11 illustrates an enlarged view of the case review dashboard 400 of FIGS. 4 and 6 when a cursor 1 is placed over a chest compression rate data point, according to embodiments of the present disclosure. Similarly, a summary callout 1102 pops up to display the particular rate recorded for the selected compression.

Figure 12:
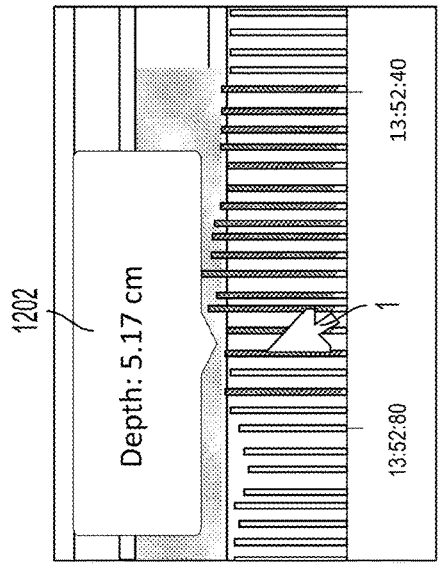
FIG. 12 illustrates an enlarged view of the case review dashboard of FIGS. 4 and 6 when a cursor is placed over a chest compression depth data point, according to embodiments of the present disclosure.

FIG. 12 illustrates an enlarged view of the CPR performance summary dashboard of FIGS. 4 and 6 when a cursor 1 is placed over a chest compression depth data point, according to embodiments of the present disclosure. Similarly, a summary callout 1202 pops up to display the particular compression depth recorded for the selected chest compression.

Figure 13:
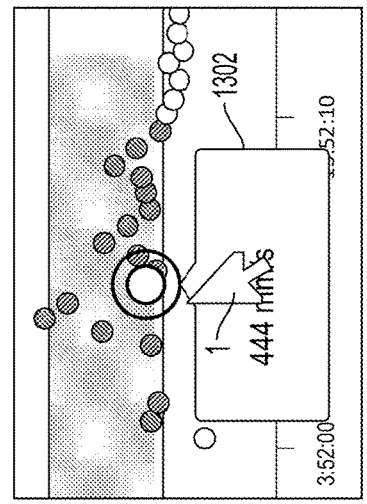
FIG. 13 illustrates an enlarged view of the case review dashboard of FIGS. 4 and 6 when a cursor is placed over a release velocity node, according to embodiments of the present disclosure.

FIG. 13 illustrates an enlarged view of the Case review dashboard 400 of FIGS. 4 and 6 when a cursor 1 is placed over a release velocity data point, according to embodiments of the present disclosure. Similarly, a summary callout 1302 pops up to display the particular release velocity for the selected chest compression.

According to some embodiments of the present disclosure, a user may select a link or button or other selection mechanism to export all or a portion of the data displayed in the dashboard 400 and/or the trend report 800. According to some embodiments, data may be exported in bulk (e.g. downloaded from server 126 and/or 128 via the user interfaces of FIGS. 4-13) based on tags and/or other search tools, filters, or criteria. For example, such export tools may permit a user to download case data based on date or date ranges, patient population criteria including tags, and/or the like.

Various statistical analysis methods may further be used to create reports, and/or to assist the user in improving performance metrics over time, and/or diagnosing which performance metrics are causing an aggregate or composite score to fluctuate out-of-control, and/or which performance metrics have a higher impact than others on certain other performance metrics. These methods, which may be employed for data sets and types of data similar to those described herein, as well as combinations and sub-combinations of such data and data sets, may include change-point analysis, control charts, six-sigma, logistic regression, linear regression, imputation, rescaling, extrapolation, interpolation, normalization, analysis of variance, chi-squared analysis, analysis of correlation, linear modeling, histograms, pareto analysis, regression analysis, root cause analysis, scatter analysis, stratification and/or parametric regression. Other statistical methods, such as those pioneered by George Box, permit statistical control by monitoring and feedback adjustment, including analytical determinations of which variables have the greatest impact on a desired output.

FIGS. 14A-D illustrate examples of statistical process control and improvement (SPCI) dashboard tools along with an example of an SPCI process. SPCI dashboard tools may be used to improve the delivery of medical care, for example, improve CPR delivery quality and/or patient survival rates or percentages. Improving survival of critically ill patients is fundamentally an iterative two-step procedure of first assessing the process control of a medical care system, and then, once a process is determined to be under control, of engaging in process improvement. For example, the medical care system may be a group of caregivers that provide CPR. In such an example, process control may be directed at determining that the delivery of CPR (e.g., compression depth, compression rate, and/or other CPR metrics) is in-control. Process improvement may be directed at adjusting the process of delivering CPR to improve the efficacy of the CPR delivery (e.g., improve patient outcomes).

The case review dashboard 400 may include an SPCI tab 1401. The user of the dashboard 400 may select the SPCI tab 1401 to access the SPCI dashboard tools. The SPCI dashboard tools may include process-behavior charts such as, for example, but not limited to, the control chart 1400. Other examples of process-behavior charts include, but are not limited to, p-chart, np chart, EWMA, CUSUM, regression control, x-R, x-s, Shewhart charts, or three-way charts. Process-behavior charts may provide statistical tools to determine if a process and/or a data set is in a state of control. For example, the process may include delivery of medical treatment and the data set may include medical treatment performance data generated during the delivery of the medical treatment and/or medical treatment patient outcome data generated during and/or after the delivery of the medical treatment.

The control chart 1400 includes a horizontal axis 1402 (e.g., an X-axis) which is in units of time, and a vertical axis 1403 (e.g., a Y-axis), which is a value for the treatment performance parameter and/or patient physiological parameter being monitored and/or controlled. The treatment performance parameter(s) and/or patient physiological parameter(s) may correspond to one or more patients, one or more groups of patients, one or more caregivers, and/or one or more groups of caregivers. Further, these parameters may be selected based on filters discussed above (e.g., patient age filter, time period filter, caregiver filter). For example, the enterprise administration server 128 may retrieve treatment data associated with one or more groups of caregivers from the enterprise storage server 126 based on the caregiver filter. The control chart 1400 may then form the basis for an evaluation of the treatment procedures of the one or more groups of caregivers. Process changes and improvements, as determined based on evaluation of the control chart 1400 and as described in detail below may improve the caregiver procedures and thereby may improve patient medical outcomes in response to these procedures.

The X-axis time scale may be time stamps from the data collected by the treatment monitoring system 10 (e.g., second, minutes, hours, days, months, years, etc.). In this example, the Y-axis is a treatment performance parameter, e.g., chest compression rate, chest compression depth, chest release, etc. as measured and determined by the treatment monitoring system 10 based on signals from the CPR metrics device 14. The data may be aggregated over a time period (e.g., minutes, hours, days, weeks, months, years) based on a statistical measure (e.g., average, deviation, variability, maximum, minimum, etc.). The particular parameter, the time period, and/or the statistical measure may be user-configurable via the dashboard 400 (e.g., the dashboard 400 may be configured to accept user input indicative of the particular parameter, the time period, and/or the statistical measure). For example, the average chest compression rate for a caregiver unit over a period of a day or a week or a month may be represented in the control chart 1400. Chest compression rate is an example only and the Y-axis may be another treatment performance parameter or patient physiological parameter and/or may be a statistical measure for the treatment performance parameter and/or patient physiological parameter (e.g., average, deviation, variability, maximum, minimum, etc.). For example, the Y-axis may be one or more of the metrics discussed with regard to FIGS. 4 and 8, such as, but not limited to, compression quality, average compression depth, average compression rate, average release velocity, average compression fraction, average ventilation rate, average pre-shock pause, average post-shock pause, depth variability, rate variability, longest pause, percent of compression depth in target, percent of compression rate in target, time to first compression, time to first shock, total CPR time, or a ROSC related statistic, etc.

The mean value of the treatment performance parameter over time is indicated by a center line 1404. The chart includes an upper control limit 1408 and a lower control limit 1406. The upper control limit 1408 and the lower control limit 1406 may be selected based on a particular number of standard deviations (e.g., one standard deviation, two standard deviations, three standard deviations, etc.) from the mean value at the center line 1404. The control limits allow for acceptable variations in the treatment parameter beyond the target ranges. In an example, the SPC chart 1400 may include an indication 1420 of the target range for the Y-axis parameter.

Figure 14A:
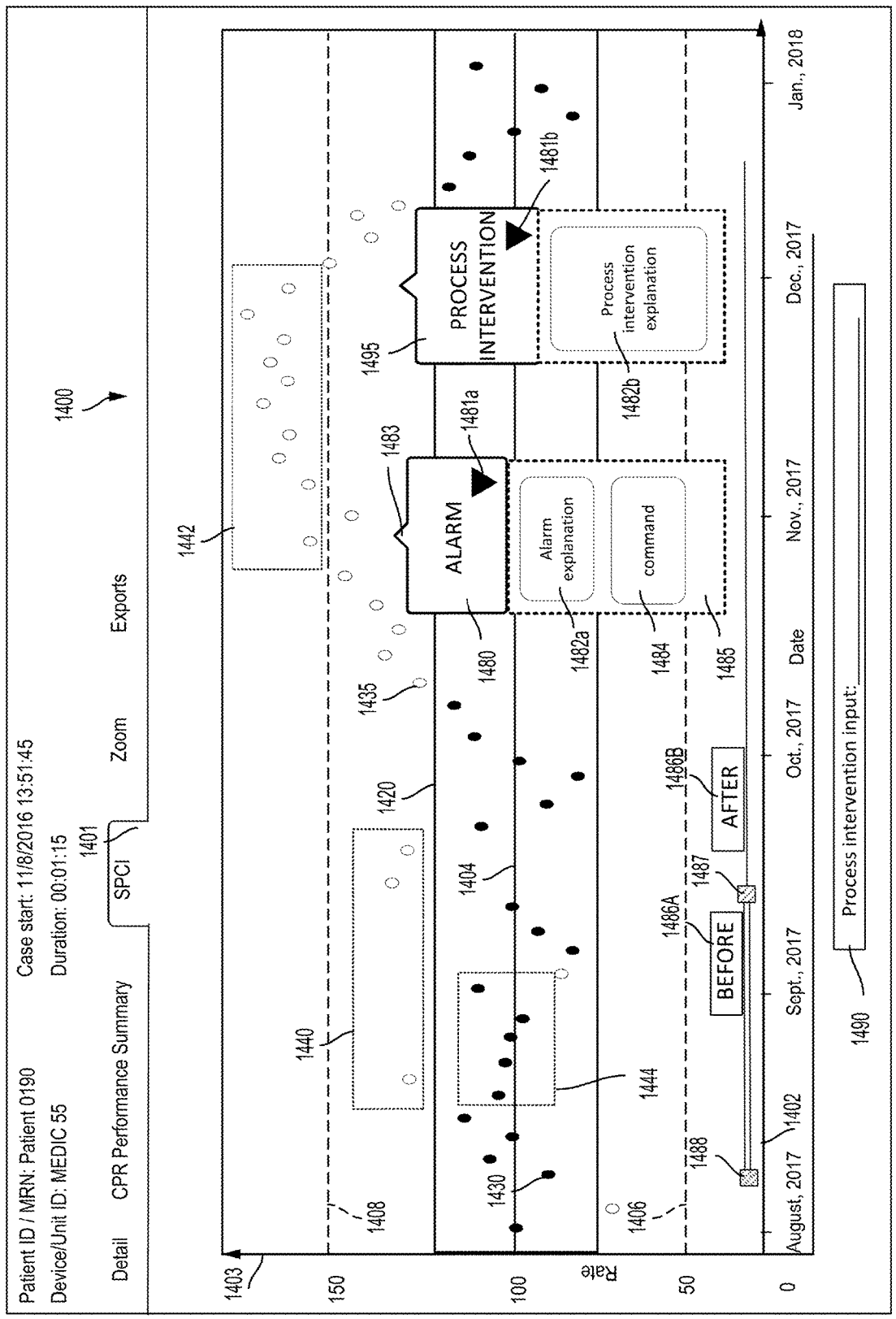
FIG. 14A illustrates a control chart for statistical process control of one or more treatment performance parameters, according to embodiments of the present disclosure.

The treatment performance parameter data points are plotted as shown by the open circles (e.g., the open circle 1435) and filled dots (e.g., the filled dots 1430) in FIG. 14A. In this example, the filled dots are measured compression rates within the target range for the compression rate and the open circles are measured compression rates outside of the target range for the compression rate. These indicators of data points are examples only and other shapes and/or indicators are within the scope of the disclosure.

Process control may allow for quality control of a process over time based on statistical analyses of process data. For example, the process may be the delivery of chest compressions. With process control, a value of a treatment parameter may be monitored over time to determine if the values of the treatment parameter are within control limits determined based on historical data. The control limits represent boundaries of acceptable and expected statistical variation for the treatment parameter. These values are due to chance (i.e., random) causes and are considered to be expected and acceptable statistical variations. For example, average and standard deviation for a set of historical data for compression depth for properly performed manual compressions may be determined. The control limits may be set at a certain number of standard deviations from the average. For example, the upper and lower control limits may be set at ±1σ, ±2σ, ±3σ, etc. Values of the treatment parameter that are within the control limits correspond to a process that is "in-control." The process-behavior chart (e.g., the control chart 1400) may be designed such that values of the treatment parameter that exceed the control limits are most likely due to assignable causes (as opposed to expected statistical variation). Therefore, if values of the treatment parameter exceed the control limits, then the process may be flagged as "out-of-control."

In some cases, the assignable cause(s) of the "out-of-control" process may be unknown prior to the detection of the "out-of-control" process by the process-behavior chart. In this case, the process may be further evaluated to determine and correct the assignable cause. For example, the process-behavior chart may evaluate average compression depth over time for a group of EMS workers associated with a particular dispatch center. If the average compression depth for the group of EMS workers is "in-control" (i.e., the measured compression depths are within the control limits) then the variations in compression depth are likely due to expected variations in chest compression technique from person to person and for a manual process (i.e., a human being likely does not compress to exactly the same depth for each compression). These variations may include variations within the target ranges and variations beyond the target ranges. The control limits may allow for compression depths within or beyond the target range that are considered to be attributable to these expected variations. However, if the average compression depth for the group of EMS workers is "out-of-control" (i.e., the measured compression depths are beyond the control limits) then the variations in compression depth may be due to the assignable causes of a deterioration in compression technique for the group of EMS workers and/or improper training.

In an implementation, the memory 308 of the enterprise server 128 may include processor-executable instructions configured to cause the processor 302 of the enterprise server 128 to generate the control chart 1400, and/or other statistical analysis, and provide the control chart 1400 and/or other statistical analysis as display information to one or more of the computing devices 122 and/or 132. Data may be added to the control chart 1400 as when it is uploaded to the enterprise server 128 and/or the control chart 1400 may be generated from historical data that has been previously uploaded to and stored by the enterprise server 128.

Figure 14B:
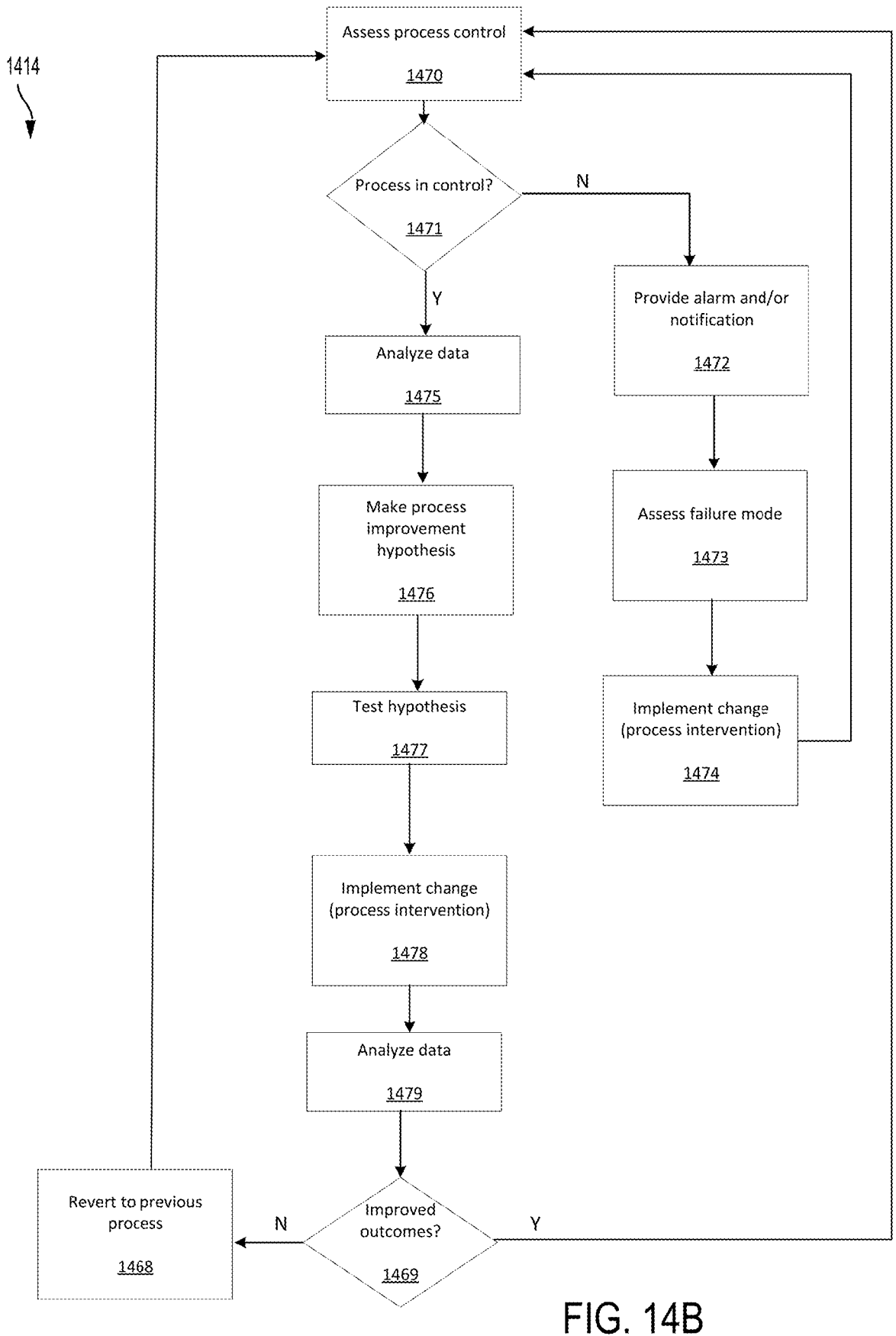
FIG. 14B illustrates a process for statistical process control and improvement.

Referring to FIG. 14B, with further reference to FIGS. 14A, C, and D, an example of a process 1414 for improving delivery of medical care is shown. The first steps of assessing (e.g., evaluating) whether or not a process is in-control or out-of-control and subsequently bringing the out-of-control process into control, if necessary, are depicted in blocks 1470-1474. The control chart 1400 may indicate whether or not a process is in-control or out-of-control by showing the performance data relative to control limit thresholds. For example, in the control chart 1400, the group of points 1440 are examples of data points outside of the target range but within the control limits 1406 and 1408. The group of points 1442 are examples of data points outside of the target range and outside of the control limit 1408. The group of points 1444 are examples of data points inside the target range and inside of the control limits 1406 and 1408. A user may view the control chart 1400 and/or the dashboard 400 may determine that one or more data points are beyond a control limit and provide an out-of-control indication, for example an alarm marker 1480, that one or more data points are exceeding a control limit. The number of data points exceeding the control limit (e.g., the upper control limit 1408 and/or the lower control limit 1406) that are required in order to generate the out-of-control indication may be a default value in the processor-executable instructions of the enterprise application server 128 and/or may be a user-configurable value.

If the process is found to be out-of-control (process block 1471), then the alarm marker 1480 is generated at the process block 1472. The dashboard 400 may provide a notification, for example, a user notification, with or in lieu of the alarm. For example, the dashboard 400 may display the alarm marker 1480 superimposed on the control chart 1400, with some indicator 1483 aligned to indicate where in the data set the process went out-of-control. Alternatively, the dashboard 400 and/or the enterprise application server 128 may generate a notification such as an email, text, audio, and/or other form of visual or audio, or verbal communication to a pre-specified recipient, e.g. a text prompt to a medical director's cellular telephone or an email to the medical director's computing device.

At process block 1473, the process 1414 may determine the assignable cause for the process to go out-of-control. For example, the enterprise application server 128 may perform a data analysis process to assess the source of the control failure (i.e., the assignable cause of the out-of-control process), for example by providing a menu pulldown arrow 1481a on the alarm marker 1480. The menu pulldown arrow 1481a may open a pulldown area 1485 that contains more detailed information 1482a about the control failure as well as one or more commands 1484. The user may select a command or the enterprise application server 128 may automatically implement a command. The command may, for example, initiate a statistical analysis, for example, a multi-variate statistical analysis, to determine the assignable cause of the out-of-control process. As an example, the statistical analysis may include a multivariate logistic regression. In this example, the multivariate logistic regression is performed on two groups of data—the data occurring within some specified time period adjacent to the time of alarm, and a second set for a range of time prior to the first set of data. For instance, in the case of an out-of-control process such as in FIG. 14A, the logistic regression may show that changes in compression rate are inversely correlated to compression depth and that the compression depth has also decreased over the same time period as the increase in compression rate, thereby more clearly indicating the source of the failure, and also what areas of training is required for the medical personnel. For each case, data may be collected as to: identity of particular individuals performing CPR during the resuscitation or other medical treatment; identity of particular crews (e.g. "Ambulance Station 52"); time since last training for a particular individual or crew; time on the job for a particular individual; or other potential systemic causes of improper or ineffective treatment. Based on the results of the analysis, a process intervention, for example a process change, may be implemented in the medical system, as depicted in process block 1474. Following the process change, the process 1414 may return to the process block 1470 to evaluate (e.g., assess) a process-behavior chart for the changed process.

For example, at the block 1470 the process 1414 may evaluate a first treatment process using a first control chart 1400 (e.g., the dashboard 400 may generate the control chart 1400 based on data from the treatment monitoring system 10 during one or more implementations of the first treatment process for patient care). If this first treatment process is found to be out-of-control, the process 1414 may generate an alarm and/or notification and determine the assignable cause(s) for the out-of-control state of the first treatment process. The user of the dashboard 400 may implement a treatment process change relative to the first treatment process (e.g., change a treatment parameter target, change treatment training, change a patient evaluation procedure, change personnel, change equipment, etc.) based on the assignable cause(s). The treatment monitoring system 10 may then provide data during one or more implementations of a second treatment process which includes the implemented process change. The dashboard 400 may generate a second control chart 1400 to evaluate whether or not the second process is in-control or out-of-control. In this manner, the dashboard 400 may determine whether or not the process change is a remedy for the assignable cause determined to have brought the first process out-of-control.

The command 1484, e.g. "Perform Logistic Regression" may also contain visual interaction features BEFORE/AFTER slider 1486A and 1486B which provides for a movable slider 1488 that demarcates the first set of data from the second set. There may also be a second slider 1487 to indicate the start of the second data set.

The first part of SPCI, namely, process control (PC), may assess whether the process is in-control, and then bring it into control if necessary, as depicted in blocks 1470-1474 of FIG. 14B. The second part of SPCI, process improvement (PI), is depicted in process blocks 1468, 1469 and 1475-1479 of process 1414. The dashboard 400 may statistically analyze data in one or more process-behavior charts to determine a predicted change in a patient outcome based on a selected patient outcome. Once the process has been shown to be in-control at process block 1471, the enterprise application server 128 may analyze the data at process block 1475 using statistical and analytic methods. These methods may include, for example, but not limiting of the disclosure, logistic regression, linear and non-linear regression, multiple regression, the General Linear Model (GLM), and analysis of variance (ANOVA). The analysis will typically select a patient outcome variable to be optimized such as patient survival, patient return of spontaneous circulation (ROSC) or another nearer term physiologic variable such as $EtCO_2$, volumetric $CO_2$, brain oxygenation, tissue oxygenation, blood flow during chest compression, such as invasive blood pressure, one or more ROSC parameters (e.g., time to ROSC, percent of patients achieving ROSC). In an implementation, the patient outcome variable may be a user-selected patient outcome variable.

For example, ROSC may be chosen as the outcome measure for the logistic regression. In one example, on a particular set of data, and based on the logistic regression analysis, the result of process block 1475, Analyze Data, might be that the dashboard software executing on the server 128 may predict that 10% more patients would achieve ROSC if the mean compression rate was increased to 118 compressions per minute (CPM). Based on this, in process block 1476, the dashboard software may generate an outcome optimization hypothesis. For example, the hypothesis may be "if compression rate is increased to 118 CPM, then ROSC rate will increase 10%." At process blocks 1477 and 1478, users of the dashboard software and/or recipients of dashboard information may test the hypothesis and implement the change as a process intervention. For example, the users may train the relevant medical personnel to use the changed compression rate. Further, the user may enter change implementation information, for example the start date and/or relevant information of the process intervention 1497, as shown on FIG. 14C, into the SPCI dashboard tool database, e.g. via a visual interface "drag-and-drop".

Figure 14C:
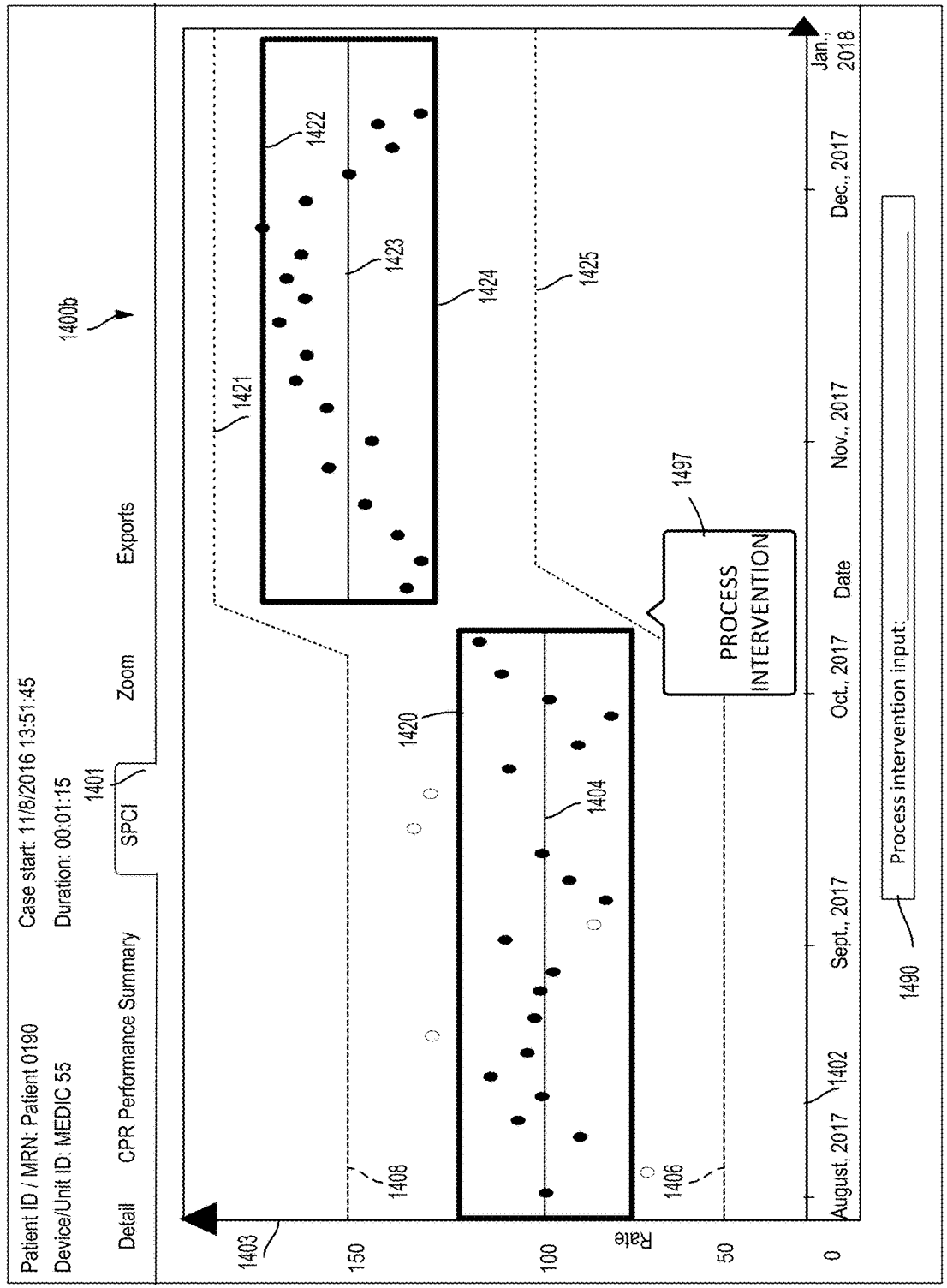
FIG. 14C illustrates adjusted control chart limits.

In some versions, additional testing may be performed after process block 1478 to verify that the process is still in-control. Referring to FIG. 14C, in this case, the control chart limits are adjusted to show the new desired compression rate limits 1421-1425. Similar control charts may also be maintained for any combination or all of the CPR performance or medical intervention performance parameters to verify process control after process block 1478.

Figure 14D:
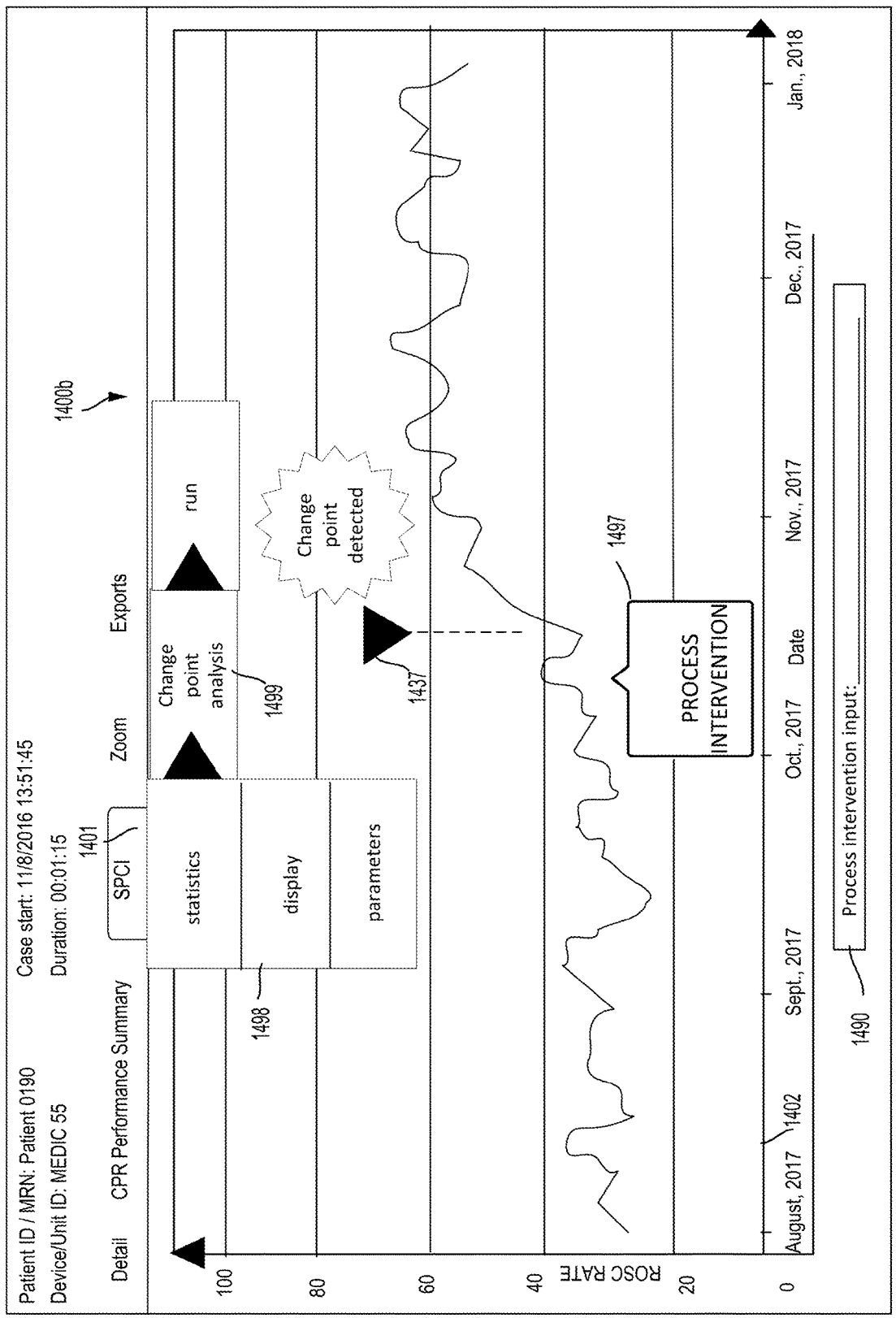
FIG. 14D illustrates a statistical process control and improvement pulldown menu.

The results of the changes are then analyzed in process block 1479, "Analyze Data". Referring to FIG. 14D, the SPCI pulldown menu 1498 in second control chart 1400b contains action buttons for various statistical analysis (STATISTICS), adjusting the scale, color and other visual chart and screen adjustments (DISPLAY), and a selection list of what parameters to display and analyze (PARAMETERS). Under the STATISTICS action button, the action button to initiate a change point analysis 1499 is found.

Fault detection and diagnosis may be similar, from a mathematical and statistical point of view, to changes in survival rates in a clinical study, where survival rate may be similar to fault rate in the fault detection problem.

The process block 1469, "Improved Outcomes?", verifies whether or not the process intervention had an impact on the outcome variable of interest, e.g. ROSC. In one embodiment, the result of the change point analysis is displayed and marked on the dashboard 400 at the time point at which detection occurred, e.g. "Change Point Detected" 1437 along with an arrow. If the time at which the change point was detected is in temporal vicinity to the time at which the process intervention 1497 occurred, then a statistical test may be run to compare the data before and after the time point at which the change point was detected. If the results after the change point are found to be statistically improved using a test such as a Chi-square test, then improvement in outcomes is verified.

As another example, the Process Improvement step in the SPCI dashboard tool (process blocks 1468, 1469, 1475-1479) may be used to evaluate the effect of a change in the target compression depth on ROSC. In this case, the change in target compression depth may be the known assignable cause. In such an example, the SPCI dashboard tool may show whether a ROSC parameter for multiple patients over a period of time with a first compression depth target (e.g., 2.1 inches or 5.3 cm) shows a statistically significant change with a second compression depth target (e.g., 2.5 inches or 6.4 cm). One or more ROSC parameters, for example, time to ROSC, percent of patients achieving ROSC, etc. may be evaluated on the SPCI dashboard tool at each compression depth. The periods of time for each compression depth may be the same periods of time (e.g., duration, dates, etc.) or may be different periods of time. The SPC chart may show whether the ROSC parameter was "in-control" (i.e., the variations in the ROSC parameter were within the control limits of the control chart) over the evaluated period of time for the respective compression depths. Further, the SPC chart may indicate whether the ROSC parameter was "in-control" or "out-of-control" at each compression depth and as a result of the change in compression depth. For example, if the ROSC parameter is within the control limits for the first compression depth and then outside of the control limits after the change in compression depth to the second compression depth, then the second compression depth target may be considered deleterious to the efficacy of the CPR treatment. In this case, a change in the compression depth target may not be recommended. Conversely, if the ROSC parameter is outside of the control limits for the first compression depth and then inside the control limits after the change in compression depth target to the second compression depth target, then the first compression depth target may be considered deleterious to the efficacy of the CPR treatment. In this case, a change in the compression depth target may be recommended.

Such statistical analysis methods may further be used to automatically resize and/or rescale any of the CPR performance metric summaries and/or the target upper and lower limits thereof. Thus the dashboard 400 may provide and implement statistical analysis tools to determine targets and/or target ranges for parameters displayed in the dashboard 400. Further, these tools may determine default values for these targets and/or target ranges and/or may determine changes to the default values.

For example, current guidelines from a resuscitative authority (e.g., the AHA) may include a target and/or target range that is a considered to be a standard of resuscitative care. For example, the target range for chest compression depth may be 5.0-6.0 centimeters. The statistical analysis provided by the dashboard 400 may determine that a narrower, wider, and/or different depth range may improve clinical outcomes compared to the 5.0-6.0 centimeter range. The target range shown by the dashboard 400 may be updated to this newly determined range. Furthermore, the newly determined range may be used in other devices (e.g., defibrillators, CPR metrics devices, etc.) so that the resuscitative care provided while using these other devices is improved. Thus the dashboard tools may enable overall improvements to the field of resuscitative care that are not limited to the specific patients and/or the specific caregivers that correspond to the treatment data evaluated with the dashboard 400. These improvements include adjustments to future care guidelines and procedures.

As another example, instead of setting an adult target chest compression depth range at 5.0 to 6.0 centimeters for a case involving an adult patient, the system (e.g. server 128) could be configured to adjust the upper 602 and lower 604 target limits as two or three standard deviations about a mean or average depth value that results in an ROSC of at least 20% over time, using statistical process control and other statistical analysis methods to set the parameters for, and monitor, the chest compression depth, according to embodiments of the present disclosure. For example, the dashboard 400 may be configured to generate the alarm marker 1480 for a user when a statistical process control chart indicates a monitored statistic moving out-of-control, or exceeding a threshold, or remaining on one side of the mean centerline for a certain number of data points, according to embodiments of the present disclosure. Further, the dashboard 400 may be configured to accept user input regarding a process intervention. The process intervention may include information regarding a change and/or adjustment in treatment performance effecting a change in the monitored parameter. For example, the dashboard 400 may provide a user-fillable field 1490 for details regarding the process intervention and/or may provide a time stamp indicator 1495 for the process intervention. The time stamp indicator 1495 may provide a menu pulldown arrow 1481*b*. The menu pulldown arrow 1481*b* may open a pulldown area 1482*b* that contains more detailed information about the process intervention.

In an implementation, the enterprise application server 128 may implement a change-point analysis on treatment performance data and/or on patient outcome data. Change-point analysis may enable a determination (e.g., by the dashboard 400) of the effect of process changes on clinical outcomes for patients and/or the effect of process changes treatment performance of care-givers. The patient outcome data may include, for example, physiological parameters for one or more patients and/or one or more groups of patients, survival rates and/or outcomes for one or more patients or one or more groups of patients, and ROSC outcomes for one or more patients and/or one or more groups of patients. Further, this patient outcome data may correspond to one or more caregivers and/or one or more groups of caregivers. A process change may include a change in treatment procedures and/or responses. For example, a medical director, caregiver, or other personnel may implement a change in a target for a parameter, such as a change in the target rate for chest compressions, the target depth, the target release velocity, etc. Other changes may include changes to an order of resuscitative operations, changes to drug delivery, changes in arrival times, changes in training procedures, changes in training information, equipment changes, software changes and/or updates, etc.

For a change-point analysis, the processor-executable instructions stored at the enterprise application server 128 may analyze a set of time-ordered data during a time period after which the data is collected (e.g., for case data, the analysis occurs post-case). In a change-point analysis, a quantity derived from the time-order data (for example, a cumulative sum) may be determined as a function of time for the set of data and changes in slope for the derived quantity plotted as a function of time may be analyzed to find change points. This analysis may include analyzing additional derived quantities, reordering data, determining statistical measures, etc. When changes are detected, data segments on either side of the change may be further analyzed to verify the detected changes and to determine if additional changes occur within these data segments. The change point analysis may generate an indication of a confidence level in the detected change. For example, the change point analysis may indicate a particular percent of confidence that a detected change actually occurred. The change point analysis may be applied to collected data points and/or to statistical measures of the data points (e.g., averages, standard deviations, ranges, etc.).

Change-point analysis may be used in conjunction with SPC. For example, the SPC may verify that a process or procedure is "in-control" and the change point analysis may enable process improvement by verifying that a change in a process or procedure, is affecting a process outcome in a desired way and that the change is in fact actually affecting the outcome (i.e., that there is some correlation between the implementation of the procedure change and a change in procedure outcome).

Embodiments of the present disclosure may incorporate, use, and/or present display data to a user according to a number of statistical and/or analysis methods or methodologies. For example, the computing device 122 and/or the enterprise application server 128 may execute one or more scoring system algorithms configured to pull selected treatment data from the database 130, or pull all treatment data from the database 130, and calculate various objective scores that reflect the quality of performance of various caregivers. This may be done by calculating scores for specific performance factors, and then aggregating such specific scores into a composite score that reflects broader and/or overall performance. Such specific performance scores may be clinical or operational, and may relate to times involved in the treatment response and/or procedures followed in the treatment services. The scores may be based on objective data in the same calculations from a variety of treatment environments to provide treatment performance scores which can be compared as between organizations, individuals, patients, response crews, geographic areas, and/or times. For example, specific CPR performance scores may be determined for a single caregiver for each of a group of performance factors including compression depth, compression rate, and release velocity. These scores may then be aggregated to determine an overall CPR performance score for the caregiver. Similarly, the specific CPR performance scores may be determined for a group of caregivers (e.g., an EMS organization) and then aggregated to determine an overall CPR performance score for the group of caregivers. The overall CPR performance score may be compared between groups of caregivers, for example, as an indication of CPR performance variations between groups of caregivers. Further, the overall CPR performance score may be monitored over time for a group of caregivers and changes may be indicative of training needs for the group of caregivers.

The scoring system algorithm may be configured to calculate a wide range of various performance scores based on a wide range of factors. One example herein is the calculation of an ST segment elevation myocardial infarction ("STEMI") score, which looks at data from the database 130 across numerous EMS responses and transports for patients with STEMI conditions, and calculates an objective STEMI score which takes into account at least one clinical score and at least one operational score. A clinical score relates to the quality of performance of clinical care given to the patient, for example whether and how rapidly medications were administered, vital signs monitored, ECG signals acquired, and/or treatment and diagnosis protocols followed. Clinical scores include all aspects of healthcare provided, including all structural and resource capabilities associated with such healthcare. An operational score relates to the quality of performance of business, logistical, or other operations not directly related to patient clinical care, for example relating to responding to emergency calls, and transporting the patient. Operational scores may include all or a portion of operational activities, including business practices such as billing.

The STEMI score may be aggregated with other scores in order to arrive at an overall "EMS Score," to permit the evaluation and comparison of entire EMS platforms, for example. Other scores that may be objectively calculated include, without limitation: EMS Safety, EMS Service Delivery, EMS Response Time, EMS Airway Management, EMS Trauma Care, EMS Stroke Care, EMS Pediatric Care, EMS Cardiac Arrest Care, and/or EMS Customer Satisfaction. If ten scores are calculated, each of which is further calculated from ten sub-scores, then an overall EMS Score may be displayed as a score out of one hundred possible points. Other topics or factors which may be scored include, but are not limited to, stroke, trauma, airway, cardiac arrest, general medical, general pediatric, shock, billing, safety, and other emergency medical service activities or systems.

The performance scores may be combined by various methods. For example, the scores may be added. As another example, the scores may be regression weighted in order to emphasize or de-emphasize certain performance measures. If some of the performance measure data is not available for a particular platform, then the enterprise application server 128 may fill in such data based on known statistical methods using average or other data from the database 130, using for example imputation, rescaling, extrapolation, interpolation, normalization, or other methods.

These evaluations and scoring systems and methods along with treatment data analysis on the dashboard 400 may be used internally within an EMS organization, as well as externally across different organizations. Internal use may include the observation of trending, as well as the learning from historical data, involving observing the impact on one parameter when another parameter or variable is changed. Further, the evaluation and scoring systems may be used for employee benchmarking, as well as benchmarking across various geographic units, or business units, for example. The EMS score and/or the treatment data used for the dashboard 400 may represent treatment performance by multiple organizations, for example by consumers or hospitals, in order to compare and evaluate the EMS organization. Such scoring and evaluation may also be used by reimbursement agencies (e.g. insurance agencies) or governmental agencies (e.g. Medicare/Medicaid), for example to verify the performance of a participating EMS organization by requiring a certain minimum aggregate score, or sub-score, in order to reimburse or approve expenses. The dashboard 400 graphs and reports provide analysis tools to evaluate and/or verify this performance. Further, such scoring and evaluation can be used in a request for proposal, or bidding process, for example for a community to ensure that a given EMS organization's performance meets certain expectations before contracting with the EMS organization. The reports and/or graphs associated with the dashboard 400 and/or the EMS score(s) may further be used in order to determine an audit risk score, such as a Medicare audit risk score.

The scores (e.g., an EMS Score or a STEMI score) may be calculated using at least 50%, or at least 60%, or at least 70%, or at least 80%, or at least 90% of the overall data as standardized data, such as National EMS Information System (NEMSIS) data elements. This maintains objectivity, and also permits practical, objective comparisons to be made across agencies (e.g. a STEMI score of 6.6 will roughly carry the same significance for Agency A as it does for unrelated Agency B).

The scores and/or evaluative information may be obtained in varying increments. For example, for a given EMS system, such as a city or county EMS system, scores may be generated at the agency level, with subset scores at the station or even the EMS response vehicle level. Scores may be created at the crew level, the individual (e.g. paramedic) level, as well as the individual patient level (e.g. individual patient, group of patient types, every patient in the agency).

The database 130 may be further configured to store patient survival data, and/or to correlate it with the patient's other records or fields. For example, the reports and/or graphs of the dashboard 400 and/or the scoring system algorithm may be configured to recognize patterns and associations between variables, and may further be configured to provide recommendations about how to improve scores or performance based on the historical data. Logical regression analysis may be used to determine which of the performance metrics actually impact patient survival, or some other patient benefit. The scoring system algorithm may also be configured to rebalance and/or re-weight the sub scores based on such historical data and analysis.

The reports and/or graphs of the dashboard 400 and/or the scoring system algorithm may be configured to generate an alarm or other message to a user based on such recommendations and/or correlations and/or predictions. For example, if the scoring system algorithm determines that female acute cardiac patients over the age of 30 respond much more favorably to aspirin administration within two minutes and fifteen seconds, rather than the industry target of three minutes, the scoring system algorithm may generate a user alert, for example via a message or sound on an output device for the computing device 122 and/or for the treatment monitoring system 10, that aspirin should be administered sooner when a female acute cardiac patient over age 30 is recognized by the scoring system algorithm. As such, the scoring system algorithm may play a part in a clinical decision support process. As another example, the dashboard 400 may provide a visible and/or audible alarm for recommended treatments.

The scoring system algorithm may implement nonlinear scoring systems, for example weighted scoring systems. Such weighting may further be configured to change or be customized, for example automatically, over time and as additional data sets are gathered. For instance, the effects of each parameter on an actual outcome of the patient may be measured, and the relative effects of such parameters may be placed into score weights that become part of scoring system algorithm. For example, the "door-to-balloon time" or the time it takes the patient to be transported from the location of the patient's heart attack to the time at which a catheter intervention is performed (e.g. a balloon catheter intervention), is known to affect patient survival rates. Each of the components, both clinical and operational, that form part of the door-to-balloon time are known, for example are known using NEMSIS dataset elements. The relative weights of the door-to-balloon time elements may simply be percentages of the total door-to-balloon time, and/or may be measured and estimated from data generated from prior studies, retrospective data from an EMS system, and/or prospectively collected data, of which a statistical analysis provides a logistic regression which may be used to generate a formula correlating the relative linear effects of each of the component variables. A non-linear regression may also be employed, which may for example involve polynomial or exponential terms. The weighting of the different components in the score permits a system to actually focus on changing the elements (e.g. inputs or variables) of the system that will most affect the desired outcomes (e.g. patient survival), so as to promote cost efficiency and other outcomes.

Statistical process control tools may be used to track performance levels of each of the score components, or system components, along with an overall or composite score. Such tools may include, but are not limited to, standard statistical methods such as analysis of variance, chi-squared analysis, control charts, analysis of correlation, linear modeling, histograms, pareto analysis, regression analysis, root cause analysis, scatter analysis, and stratification.

As described above, the data set for which scoring is performed by the scoring system algorithm may be filtered and/or grouped so as to determine a score for a particular aspect of a larger EMS process. For example, the data elements that have an impact on door-to-balloon score may be isolated, as well as elements relating to dispatch time. Such aggregated, group scores provide information about functional performance that may not be possible with an aggregated, overall score for an entire emergency medical service system, for example. Such data elements may further be grouped and/or subdivided into different time spans and/or different personnel or geographic areas, to evaluate and/or compare such groups or subdivisions with respect to each other, with respect to other organizations, and/or with respect to past performance. Such customized scoring may also facilitate the pinpointing of weaker aspects of the emergency medical services system, thereby making it easier to improve the system and thus improve the score. In other words, customized or group scoring permits scoring system algorithm to identify the portions of the emergency medical services system that are weak and need additional process improvements and/or resources.

Figure 17:
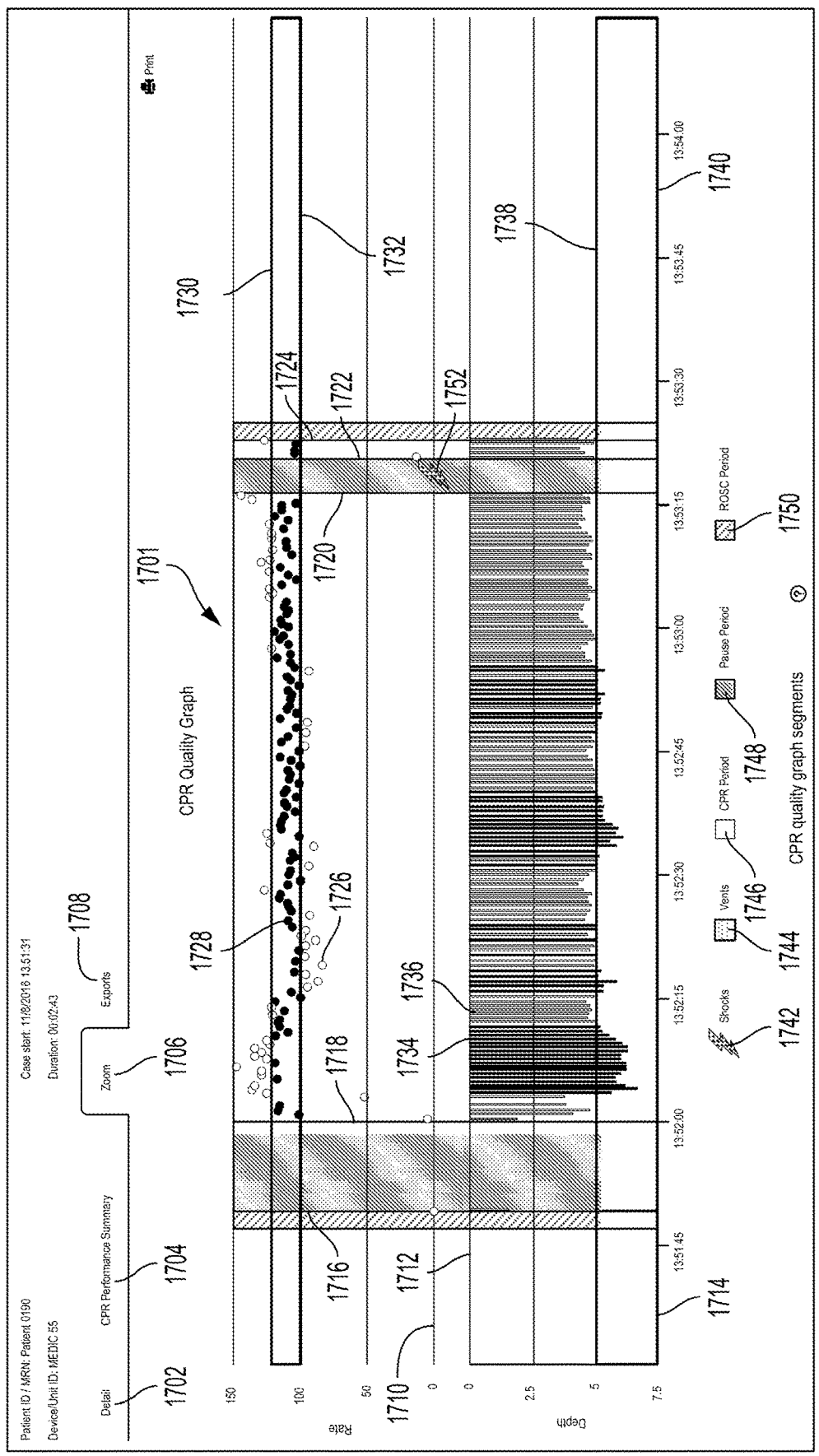
FIG. 17 illustrates a CPR quality graph, according to embodiments of the present disclosure.

FIG. 17 illustrates a CPR quality graph 1701, according to embodiments of the present disclosure. CPR quality graph 1701 includes several summaries presented separately in the time-based summaries of FIG. 4 and presents them in a single plot or chart, as shown in FIG. 17 and described below. The CPR quality graph 1701 may be part of an event or case review tool that permits the user to select different tabs for navigation. Selecting the "Detail" tab 1702 takes a user to a page that displays detailed information about the case, for example the name of the case stored on the server(s) 126 and/or 128, an indication of whether audio is present, a serial number and device type for one or more of the CPR metrics device 14, the ventilation metrics device 16, and the medical device 18, the patient name, gender, and age group, as well as a summary of the various types of data captured, for example types of vital signs data (e.g. heart rate), types of waveforms collected (e.g. ECG, ventilation), types of events that occurred in the case (e.g. whether CPR was performed, the number of shocks delivered, the number of shocks advised, the numbers of "no shock advise" situations, and the numbers of 12-lead ECG snapshots captured), and whether alarms were activated, as well as any tags that had been applied to the case information. Selecting the "CPR Performance Summary" tab 1704 navigates the user to the display of FIG. 4, according to some embodiments of the present disclosure. Selecting the "Zoom" tab 1706 navigates the user to the CPR quality graph 1701 of FIG. 17.

Selecting the "Exports" tab 1708 takes the user to an exports screen, for example, an export user interface page 1800 as shown in FIG. 18. A download case button permits the user to download all or part of the data set and/or information for the particular case being reviewed, for example in one or more proprietary or nonproprietary formats. A CPR Data export window permits the user to request a data report or summary for the particular interval, start time, and/or type of included compressions as selected in the drop-down menus. The Interval drop-down menu permits a user to select from 60 seconds, 30 seconds, and 15 seconds, although other options may be used. The start time selection permits a user to select from "power on time" and "pads on time;" other options may be used, for example a manually-entered start time may be used to permit a user to enter a start time. If the "power on time" is selected the exported data and/or report will begin at the time that the CPR metrics device 14, the ventilation metrics device 16 and/or the medical device 18 was powered on, while if the "pads on" time is selected the exported data and/or report will begin at the time that the sensors for the CPR metrics device 14, the sensors for the ventilation metrics device 16 and/or the sensors and/or electrode pads for the medical device 18 were applied to the patient 116. The "Included Compressions" selection permits the user to select between "only compressions in drawn CPR periods" or "all compressions;" other options may be used. Selecting "only compressions in drawn CPR periods" will provide in the export only the compressions applied during a period that is identified as a period during which CPR was being applied. Selecting "all compressions" will include compressions applied both during and outside of the time during which CPR was being performed. Selecting the "Request CPR data report" button or option will allow the user to save locally the data and/or report which includes the data as filtered by the "Interval" and "Start time" and "Included compressions" selections, according to embodiments of the present disclosure. The "Request Case Summary Report" option permits the user to download a full disclosure report in portable document format, for example.

Referring again to FIG. 17, the CPR quality graph 1701 includes a common time x-axis 1714, in this instance shown as horizontal, which reflects time. With respect to the common time x-axis 1714, the graph 1701 includes several pieces of information in the same graph. The graph 1701 includes a plot of compression rate with rate values beginning at a zero axis 1710 and plotted upwardly from the zero axis 1710, as well as a plot of compression depth with values beginning at a zero axis 1712 and plotted downwardly from the zero axis 1712 as shown, according to some embodiments. For the compression rate plot, upper 1730 and lower 1732 values for the target rate range are indicated by lines, with the space between lines 1730, 1732 optionally filled by a color or pattern different from the surrounding color or pattern to indicate the target range for the values. Each of the chest compressions applied during the event may be plotted, and the compressions applied at a rate within the target rate may be plotted in one color (e.g. green) as shown at 1728, and the compressions applied at a rate outside of the target rate may be plotted in another color (e.g. red) as shown at 1726.

Similarly, the chest compression depth plot may include a display of lower 1738 and upper 1740 limits indicating a target range, and may optionally be filled by a color or pattern different from the surrounding color or pattern to indicate the target range for the values. Each of the chest compressions applied during the event may be plotted, and the compressions applied within the target compression depth may be displayed in one color (e.g. in green) as shown at 1734, and the compressions applied outside of the target compression depth may be displayed in another color (e.g. red) as shown at 1736.

The graph 1701 further includes event information similar to the event information of the event summary 406 in FIGS. 4 and 5. The CPR Quality graph 1701 begins at time 1716, and ends at an end time 1724. From time 1716 to time 1718, the graph is colored the color 1748 indicating a "pause period" or time during which CPR was not being performed. From time 1718 to time 1720 the graph is colored the color 1746 indicating "CPR period" or time during which CPR was being performed. From time 1720 to 1722 the graph indicates the pause period with the color 1748, and from time 1722 to the end time 1724 the graph indicates a CPR period. At time 1752 a shock symbol 1742 appears on the graph 1701, indicating that a defibrillator shock was applied to the patient 116 at that time. Other visual information may be applied and/or displayed, including ventilations administered (which, if present, would be shown by color 1744 in legend), and ROSC period (which, if present, would be shown by color 1750 in legend), according to embodiments of the present disclosure. The CPR quality graph 1701 displays the data from the same data set as that displayed in the dashboard 400 of FIGS. 4-7, according to some embodiments of the present disclosure. According to embodiments of the present disclosure, the graph 1701 of FIG. 17 may display a fewer or greater set of metrics, statistics, and/or features, for example, the graph 1701 could display a release velocity summary, for example similar to that of summary 414 of FIGS. 4 and 6 and/or other metrics and summaries as well.

Figure 19:
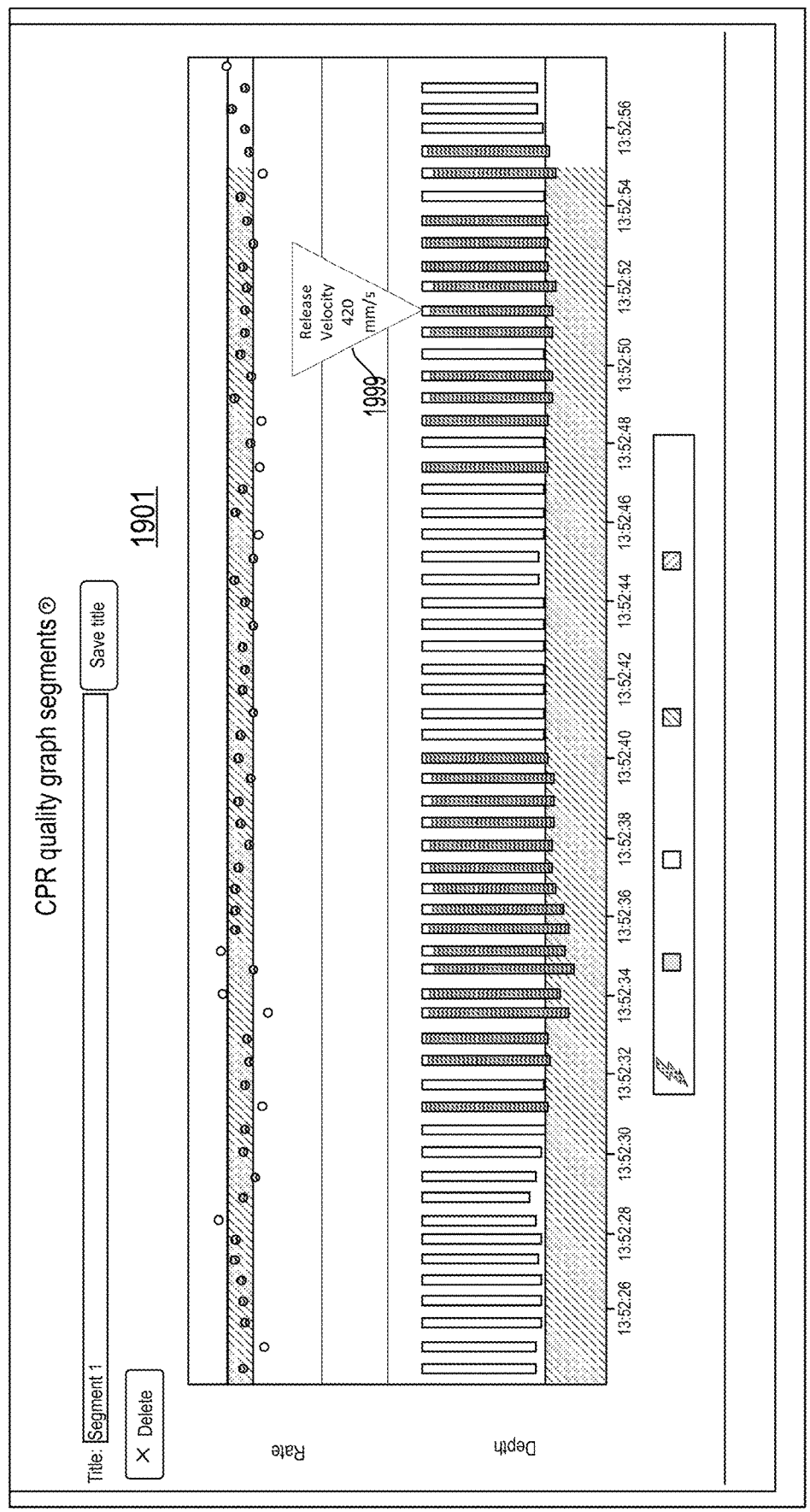
FIG. 19 illustrates a clip segment from a CPR quality graph according to embodiments of the present disclosure.

FIG. 19 illustrates a clip segment 1901 of the CPR quality graph 1701, according to embodiments of the present disclosure. The clip segment 1901 is a segment of the CPR quality graph. According to some embodiments, a user may use a selection mechanism, for example a mouse and pointer or other user input device, to "drag" a selection window across the graph 1701 to select a beginning and an ending time. When the user finishes the selection (e.g. releases the button or ends the dragging action across the graph 1701), the display within the graph 1701 enlarges, or zooms, to include as beginning and end time points the beginning and end time points that were selected during the user selection (i.e. the dragging of the pointer across the graph). A button appears, for example on or in proximity to the graph 1701, that allows the user to save the clip or user selected time window for later use. For example, the button may say "Clip Segment" and selection of the button reproduces the zoomed or selected portion or clip of the graph 1701 to a portion below the graph 1701, into the clip segment 1901. In some embodiments, the "clip segment" button may be present on the graph 1701 continuously, and/or even before the user time selection or dragging. The clip segment 1901 includes a title box to allow the user to name the segment, and a "save title" to link the user-entered title with the particular clip segment 1901, which permits the clip segment 1901 to be saved and/or referred to for later use. Such segments of the CPR quality graph may also be exported or saved locally, for example according to the methods described above with respect to the export user interface of FIG. 18. The graph 1701 may further include a "reset" button or the like, which upon user selection causes the display to revert to the original time window (e.g. covering the full event or case as shown in FIG. 17, for example). According to some embodiments of the present disclosure, this "zooming" or "clipping" or enlargement as described herein with respect to FIG. 19, and subsequent saving for later use, may be performed on any of the visual depictions shown and described herein, including without limitation any of the charts, graphs, and/or summaries shown and described with respect to FIGS. 4, 8, and 17.

Figure 20A:
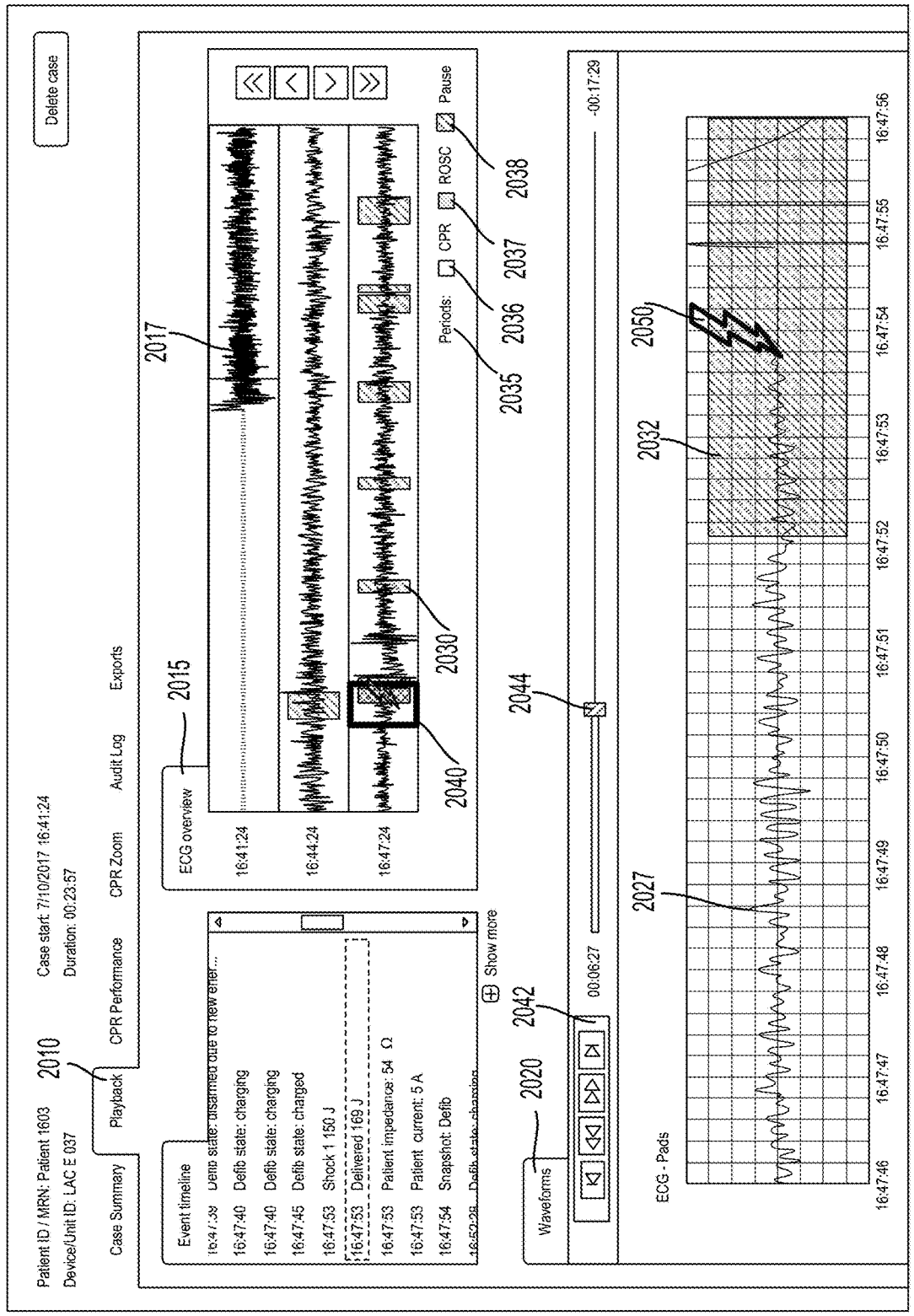
FIGS. 20A and 20B illustrate ECG overview data and magnified data.
Figure 20B:
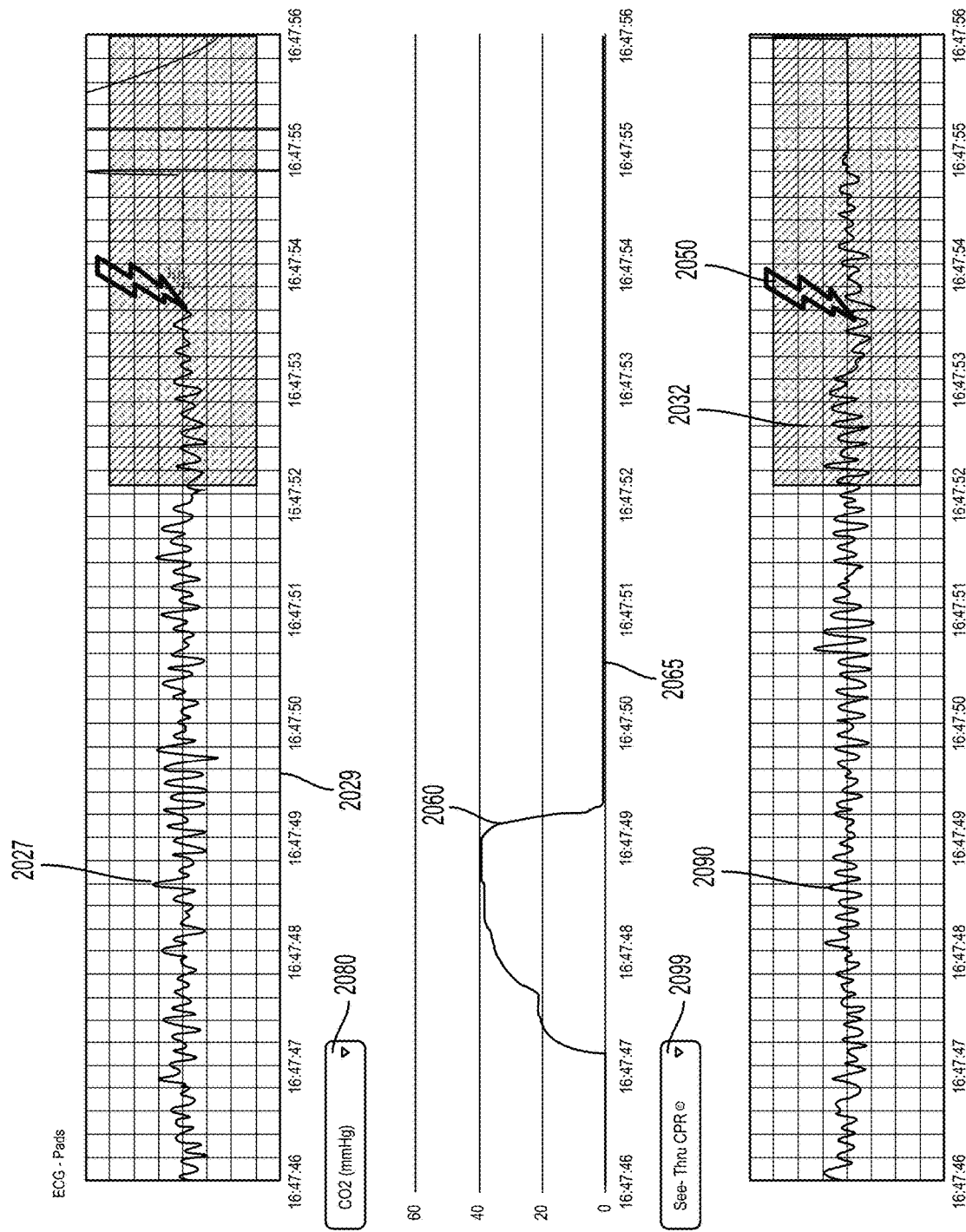

Referring to FIGS. 20A and 20B, ECG overview and magnification charts are shown. To display data from the treatment monitoring system 10 (e.g., ECG data, CPR performance data, physiological data, etc.) along a common timeline, the enterprise application server 128 may implement an algorithm that provides processor-executable instructions that enable the dashboard 400 to display data, collected from separate sources (e.g., the CPR metrics device 14, ECG electrodes, etc.) within the treatment monitoring system, along the common time scale. The dashboard 400 may provide a "playback" tab 2010. Within the "playback" tab, the dashboard 400 may provide an "ECG overview" tab 2015 that may show the ECG data 2017 over the entire duration of the case. Further the dashboard 400 may provide a "waveforms" tab 2020. Within the "waveforms" tab 2020, the dashboard may provide a magnified view of the ECG waveform. The magnified view of the ECG waveform may show magnified ECG data 2027 for a portion of the duration of the case. Thus, for example, if the duration of the case is 23:57 minutes, the ECG overview may display the ECG data for the entire 23:57 time period (i.e., as shown in the example of FIG. 20A, both the case and the ECG data overview start at the same time stamp, e.g., 16:41:24, and cover the same subsequent time interval, e.g., 23:57 minutes, and the case and the ECG data overview may conclude at the same time, e.g., 17:05:21). In contrast, the magnified ECG data covers a portion of the case duration. For example, the magnified ECG 2027 as shown in the example of FIG. 20A covers a time period from 16:47:46 to 16:47:56 which is a one-minute interval within the 23:57 minute duration of the case. The portion of the ECG overview 2017 displayed in the magnified ECG data 2027 is user-selectable. For example, the dashboard 400 may provide a selection tool with which an enterprise system user 124 may select the portion of the ECG overview 2017 for display in the magnified ECG data 2027. For example, the selection tool may include a slider icon 2044 and/or playback buttons 2042. The magnified portion of ECG waveform may be indicated by, for example, a box 2040 or other feature that identifies the portion of time in the ECG overview 2017 that is shown in the magnified waveform 2027.

All of the ECG data displayed by the dashboard 400 (e.g., ECG overview 2015 and the various waveforms 2020 such as "ECG pads" and "See-Thru CPR") may be downsampled when provided to the computing device 122 by the enterprise application server 128 via the network 12. For example, the ECG waveform is a continuous time-series waveform received at the treatment monitoring system 10 as an analog signal from a medical device 18. The medical device 18 may be a defibrillator or patient monitor/defibrillator that includes electrodes configured to collect an ECG waveform from a patient when the electrodes are attached to that patient. The treatment monitoring system 10 may digitize this analog signal and provide the digitized signal in a lossless format to the enterprise storage server 126. The digitized signal may include N data points. The treatment monitoring system 10 may provide the complete time series in the lossless format including the N data points of the digitized signal to the enterprise storage server 126 via the network 12 and the enterprise storage server 126 may store the N data points of the complete time series in the lossless format and identify the set of N data points as the ECG waveform corresponding to a patient and/or a case. The enterprise storage server 126 may store the ECG in the received lossless format. In the lossless format, the treatment monitoring system may compress the ECG data for transmission to the enterprise application server using algorithms that preserve all of the original ECG data from the medical device 18. In contrast to a lossless format, a lossy format may compress data using algorithms that discard data. Subsequently, the enterprise application server 128 may provide a downsampled ECG waveform to the dashboard 400, e.g., as displayed on the computing device 122. The downsampled ECG waveform may not include N data points but rather may include a portion of the N data points. This downsampled ECG waveform may include a sample of the N data points. Therefore, the number of data points M in the downsampled ECG waveform would be less than N (M<N).

In order to provide the ECG information (e.g., the overview and/or the magnified view) via the web page format, the ECG data may be downsampled and provided to the display of the dashboard 400 via a communications channel of the network 12. The display properties of the dashboard 400 and/or the properties of the communications channel, such as bandwidth, may require downsampling of the ECG information. However, as the ECG information includes visual features (e.g., QRS complexes or lack thereof) that are critical to the interpretation of the ECG information with regard to patient care, the downsampling of the ECG information should be done in a manner that preserves these features without providing the ECG information in a lossless format and satisfying the display and/or communication channel limitations that may limit the amount of data that can be provided via the channel. For example, without the downsampling, the digitized ECG information may include on the order of 100,000 data points (for example, 3 sets of 3 minutes of 250 Hz sampled ECG information). Thus the enterprise server 128 may implement a downsampling algorithm that that preserves these features and still satisfies the display and/or communication channel requirements. The downsampling algorithm may enable downsampling of the ECG data for use in a web page format while retaining visual features of the ECG data including, for example, the QRS complexes. In contrast, an algorithm such as, for example, regression analysis, may remove or obscure fluctuation details in the data which, in the case of ECG data, may be critical to the interpretation of the data. The downsampling algorithm reduces the number of downloaded data points in order to sample data obtained on a continuous time scale and retain salient features of this data. Such an algorithm may reduce the number of downloaded data points by an order of magnitude (for example, the ECG may be downsampled accurately with 1000-5000 downloaded data points). Examples of algorithms include, but are not limited to, mode median bucket algorithm, minimum standard error bucket algorithm, longest line bucket algorithm, largest triangle one bucket algorithm, largest triangle three bucket algorithm, and largest triangle dynamic algorithm. These algorithms are examples only and not limiting of the disclosure of the disclosure. Such algorithms are ranking algorithms that apply ranking criteria to the original data to determine sample sizes for the data and to determine which data points to include in each sample. The ranking criteria may be statistical, for example based on a mode, median or standard error and/or may be geometric, for example, based on a line length or area.

The processor-executable instructions stored at and executed by the enterprise application server 128 may include instructions that enable an overlay of periodic or discrete events during a case on the ECG waveform (e.g., the overview 2017 and/or the magnified view 2027). The instructions may enable display of event information (e.g., periods of time corresponding to chest compressions, ROSC, chest compression pauses, etc.) concurrently with the ECG waveform. The dashboard 400 may display the periodic and/or the discrete events during a case on the ECG waveform as a shaded overlay and/or as icons. For example, the legend 2035 includes a CPR shading 2036 corresponding to a chest compression period, a ROSC shading 2037 corresponding to a ROSC period, a pause shading 2038 corresponding to a pause period. The dashboard 400 may overlay one or more of these shadings on the ECG overview (e.g., the shaded area 2030 may correspond to the pause shading 2038) and/or on the ECG magnified view (e.g., the shaded area 2032 may correspond to the pause shading 2038). For example, the event information may include periodic events and/or discrete events. The display may indicate a time synchronization of the periodic and/or the discrete events. The time synchronization of the event information with the ECG waveform may be, for example, to a nearest millisecond time stamp. The periodic events may include, for example, the CPR period(s) and pause period(s) that are continuous over a sub-region of the ECG waveform time line. The dashboard 400 may display these periodic events as shading behind or over the ECG waveform. The discrete events may include, for example, shock events. The shock event may be a discrete point in time, to, for example, the nearest millisecond (or other time increment), on the ECG timeline at which a shock is administered to the patient. The dashboard 400 may display the shock event as a shock icon (e.g., the icon 2050) at point along the ECG waveform that indicates the time at which the shock was applied. The algorithm may further provide indications of synchronized cardioversion and external pacing as icons on the ECG waveform. For example, the dashboard 400 may include an "S" or other indicator at the nearest millisecond for which the synchronized cardioversion was recorded in a case. As another example, the dashboard 400 may include a "P" or other indicator at the nearest millisecond at which a pacing pulse was detected.

The dashboard 400 may concurrently display the magnified portion 2027 of the ECG waveform and a physiological parameter and/or treatment parameter, for example, the end-tidal carbon dioxide graph 2060. The selection tool 2080 may provide a drop-down menu enabling the selection of the physiological and/or treatment parameter for concurrent display with the magnified ECG 2027. The time scale 2065 of the physiological parameter and/or treatment parameter may match the time scale 2029 of the magnified portion of the ECG waveform.

In an implementation, the medical device 18 may provide a filtered ECG waveform 2090 based on a filter selection tool 2099. The filtered ECG may be, for example, an ECG waveform that has been processed to filter out noise in the signal due to CPR artifacts. The processing (e.g., See-Thru CPR® from ZOLL® Medical Corp.) may extract the CPR artifact signals from the ECG waveform. In this manner, the care provider may monitor the filtered ECG waveform 2090 and may not have to pause CPR chest compressions to view an ECG free of CPR artifacts. The filtered ECG waveform may also include event shading 2032 and event icons 2050.

According to some embodiments of the present disclosure, a user may print or export the dashboard 400 and/or the trend report 800 and/or the CPR quality graph 1701 onto a single page or other concise report to permit easy review of the summary information and/or data. In some embodiments, the user may print the report in a number of different languages, for example in a user-selected language.

Embodiments of the present disclosure, including dashboards, trend reports and/or graphs (e.g., the dashboard 400, the trend report 800, and the graph 1701), permit the caregiver, quality assurance personnel, and/or supervisors, to review the data from a case and/or an event and/or set of events within the case, either just after the event and/or the case, as close as possible to the event and/or the case (e.g. as a "hot debrief"), or at a later time. This may provide the advantages of improved patient care, more rapid attention to the patient, quality assurance and improvements, performance improvement, and/or facilitated reporting of important information about the event(s) and/or the case. In some embodiments of the present disclosure, the dashboards, graphs, and/or trend reports permit the caregiver to review the data from an event and/or set of events, during a portion of the event (e.g. to improve performance or patient care during the remainder of the event), resulting in improved patient care, more rapid attention to the patient, quality assurance and improvements, performance improvement, and/or facilitated reporting of important information about the event or events.

Various modifications and additions may be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. A system for post-case analysis of cardiopulmonary resuscitation (CPR) performance trends, the system comprising:
    a treatment monitoring system comprising:
        a ventilation metrics device comprising one or more sensors configured to generate signals indicative of ventilation treatment data during a medical treatment of a patient, and
        a patient monitor/defibrillator configured to:
            receive the signals indicative of the ventilation treatment data from the ventilation metrics device during the medical treatment of the patient,
            calculate the ventilation treatment data based on the received signals, and
            transmit the ventilation treatment data; and
    a remote computing server device that is configured to communicatively couple with the treatment monitoring system and that is also configured to communicatively couple, via a network communications channel, with an output device comprising a display, wherein the remote computing server device comprises:
        at least one memory, and
        at least one processor communicatively coupled to the at least one memory, the at least one processor configured to:
            receive post-case treatment data from the treatment monitoring system, the post-case treatment data comprising the ventilation treatment data,
            store the post-case treatment data in the at least one memory with one or more case identifiers,
            responsive to a request received after the medical treatment of the patient concludes, and that includes the one or more case identifiers, provide a case review dashboard at the output device, and
            further responsive to the request received after the medical treatment of the patient concludes, provide case review information at the case review dashboard, the case review information comprising a first time trend plot that displays a ventilation rate for the patient at each of a plurality of time points during the medical treatment, and a second time trend plot that displays at least one respiratory gas parameter for the patient at one or more of the plurality of time points, wherein the first time trend plot and the second time trend plot are concurrently displayed in the case review dashboard.

2. The system of claim 1, wherein the first time trend plot displaying the ventilation rate and the second time trend plot displaying the at least one respiratory gas parameter are provided along a common time axis.

3. The system of claim 2, wherein the at least one respiratory gas parameter is end-tidal CO2.

4. The system of claim 1, wherein the first time trend plot and the second time trend plot span a time range and comprise a plurality of discrete graphic indicators, wherein a particular discrete graphic indicator represents a data point within the time range.

5. The system of claim 4, wherein the at least one processor is configured to provide an information tab at a selected discrete graphic indicator of the plurality of discrete graphic indicators, wherein the information tab indicates a numerical value of a data point represented by the selected discrete graphic indicator.

6. The system of claim 5, wherein the at least one processor is configured to provide the information tab at the selected discrete graphic indicator in response to a cursor placement at the selected discrete graphic indicator.

7. The system of claim 1, comprising an alphanumeric representation of the ventilation rate provided with the first time trend plot and the at least one respiratory gas parameter provided with the second time trend plot.

8. The system of claim 7, wherein the alphanumeric representation of the ventilation rate comprises an average ventilation rate.

9. The system of claim 1, wherein the at least one processor is configured to provide the first time trend plot and the second time trend plot with a graphical indication of a target range for the post-case treatment data.

10. The system of claim 1, wherein the patient monitor/defibrillator is coupled to the ventilation metrics device wirelessly.

11. The system of claim 1, wherein the ventilation metrics device comprises one or more of: a pulse oximeter, a blood oxygen monitor, an air flow sensor, a spirometer, a lung function monitor, and a capnography device.

12. The system of claim 1,
    wherein the post-case treatment data comprises chest compression performance data from a chest compression metrics device coupled to the patient monitor/defibrillator and electrocardiogram (ECG) data from electrodes coupled to the patient monitor/defibrillator, and
    wherein the at least one processor is configured to provide a third time trend plot of the chest compression performance data and a fourth time trend plot of the ECG data along a same time axis interval as the first time trend plot and the second time trend plot at the case review dashboard.

13. The system of claim 1, wherein the at least one processor is further configured to:
    generate a performance trend report comprising a performance analysis statistic for the ventilation treatment data for a plurality of treatment cases.

14. The system of claim 13, wherein the plurality of treatment cases are selected according to one or more user-selected filters comprising one or more of: a patient age group filter indicative of a selected patient age group, a caregiver filter indicative of one or more individual caregivers or one or more groups of caregivers, and a time interval selection filter.

15. The system of claim 1 wherein the at least one processor is configured to:
    retrieve the post-case treatment data corresponding to the one or more case identifiers; and
    provide the post-case treatment data corresponding to the one or more case identifiers at the case review dashboard.

16. The system of claim 1, wherein the output device is remote from the remote computing server device.

17. A system for post-case analysis of cardiopulmonary resuscitation (CPR) performance trends, the system comprising:
- a treatment monitoring system comprising:
  - a ventilation metrics device comprising one or more sensors configured to generate signals indicative of ventilation treatment data during a medical treatment of a patient, and
  - a patient monitor/defibrillator configured to:
    - receive the signals indicative of the ventilation treatment data from the ventilation metrics device during the medical treatment of the patient,
    - calculate the ventilation treatment data based on the received signals, and
    - transmit the ventilation treatment data; and
- a non-transitory, processor readable storage medium remote from the treatment monitoring system and having stored thereon processor-readable instructions configured to cause at least one processor to:
  - communicatively couple with the treatment monitoring system and with an output device comprising a display,
  - receive post-case treatment data from the treatment monitoring system,
- the post-case treatment data comprising the ventilation treatment data,
  - store the post-case treatment data in at least one memory with one or more case identifiers,
  - responsive to a request received after the medical treatment of the patient concludes, and that includes the one or more case identifiers, provide a case review dashboard at the output device, and
  - further responsive to the request received after the medical treatment of the patient concludes, provide case review information at the case review dashboard, the case review information comprising a first time trend plot that displays a ventilation rate for the patient at each of a plurality of time points during the medical treatment, and a second time trend plot that displays at least one respiratory gas parameter for the patient at one or more of the plurality of time points, wherein the first time trend plot and the second time trend plot are concurrently displayed in the case review dashboard.

18. The system of claim 17, wherein the first time trend plot displaying the ventilation rate and the second time trend plot displaying the at least one respiratory gas parameter are provided along a common time axis.

19. The system of claim 17, wherein the processor-readable instructions are configured to cause the at least one processor to:

provide the first time trend plot and the second time trend plot at the case review dashboard with a plurality of discrete graphic indicators, wherein a particular discrete graphic indicator represents a data point within a time range represented by the first time trend plot and the second time trend plot, and
provide an information tab at a cursor selected discrete graphic indicator, wherein the information tab indicates a numerical value of a data point represented by the cursor selected discrete graphic indicator.

20. The system of claim 17, wherein the processor-readable instructions are configured to cause the at least one processor to provide an alphanumeric representation of the ventilation rate with the first time trend plot at the case review dashboard, the alphanumeric representation comprising an average ventilation rate.

21. The system of claim 17, wherein the processor-readable instructions are configured to cause the at least one processor to provide the first time trend plot and the second time trend plot with a graphical indication of a target range for the post-case treatment data at the case review dashboard.

22. The system of claim 17,
wherein the post-case treatment data comprises chest compression performance data from a chest compression metrics device coupled to the patient monitor/defibrillator and electrocardiogram (ECG) data from electrodes coupled to the patient monitor/defibrillator, and
wherein the processor-readable instructions are configured to cause the at least one processor to provide a third time trend plot of the chest compression performance data and a fourth time trend plot of the ECG data along a same time axis interval as the first time trend plot and the second time trend plot at the case review dashboard.

23. The system of claim 17, wherein the processor-readable instructions are configured to cause the at least one processor to:
generate a performance trend report comprising a performance analysis statistic for the ventilation treatment data for a plurality of treatment cases, and
provide the performance trend report at the case review dashboard.

24. The system of claim 17, wherein the output device is remote from the at least one processor and communicatively coupled to the at least one processor via a network communications channel.

* * * * *